US009902943B2

(12) United States Patent
Tang et al.

(10) Patent No.: US 9,902,943 B2
(45) Date of Patent: Feb. 27, 2018

(54) ENGINEERED BIOCATALYSTS AND METHODS FOR SYNTHESIZING CHIRAL AMINES

(71) Applicant: Codexis, Inc., Redwood City, CA (US)

(72) Inventors: Weng Lin Tang, Singapore (SG); Helen Hsieh, Singapore (SG); Son Pham, Singapore (SG); Derek Smith, Singapore (SG); Steven J. Collier, Concord, MA (US)

(73) Assignee: Codexis, Inc., Redwood City, CA (US)

(*) Notice: Subject to any disclaimer, the term of this patent is extended or adjusted under 35 U.S.C. 154(b) by 0 days.

(21) Appl. No.: 14/652,887

(22) PCT Filed: Dec. 16, 2013

(86) PCT No.: PCT/US2013/075294
§ 371 (c)(1),
(2) Date: Jun. 17, 2015

(87) PCT Pub. No.: WO2014/099730
PCT Pub. Date: Jun. 26, 2014

(65) Prior Publication Data

US 2015/0329837 A1 Nov. 19, 2015

Related U.S. Application Data

(60) Provisional application No. 61/745,219, filed on Dec. 21, 2012.

(51) Int. Cl.

| | |
|---|---|
| ***C12N 9/10*** | (2006.01) |
| ***C12P 13/00*** | (2006.01) |
| ***C12P 17/18*** | (2006.01) |
| ***C12P 33/00*** | (2006.01) |
| ***C12P 15/00*** | (2006.01) |
| ***C12P 17/12*** | (2006.01) |

(52) U.S. Cl.
CPC .......... *C12N 9/1096* (2013.01); *C12P 13/001* (2013.01); *C12P 15/00* (2013.01); *C12P 17/12* (2013.01); *C12P 17/188* (2013.01); *C12P 33/00* (2013.01); *C12Y 206/01* (2013.01)

(58) Field of Classification Search
None
See application file for complete search history.

(56) References Cited

U.S. PATENT DOCUMENTS

| | | | |
|---|---|---|---|
| 4,518,692 | A | 5/1985 | Rozzell |
| 4,600,692 | A | 7/1986 | Wood et al. |
| 4,826,766 | A | 5/1989 | Rozzell |
| 4,950,606 | A | 8/1990 | Stirling et al. |
| 5,169,780 | A | 12/1992 | Stirling et al. |
| 5,300,437 | A | 4/1994 | Stirling et al. |
| 5,316,943 | A | 5/1994 | Kidman et al. |
| 6,117,679 | A | 9/2000 | Stemmer |
| 6,197,558 | B1 | 3/2001 | Fotheringham |
| 6,376,246 | B1 | 4/2002 | Crameri et al. |
| 6,537,746 | B2 | 3/2003 | Arnold et al. |
| 6,586,182 | B1 | 7/2003 | Patten et al. |
| 2006/0195947 | A1 | 8/2006 | Davis et al. |
| 2008/0213845 | A1 | 9/2008 | Fotheringham et al. |
| 2008/0220990 | A1 | 9/2008 | Fox |
| 2009/0312196 | A1 | 12/2009 | Colbeck et al. |
| 2010/0209981 | A1 | 8/2010 | Dhawan et al. |
| 2012/0041216 | A1 | 2/2012 | Sieber et al. |

FOREIGN PATENT DOCUMENTS

| | | | |
|---|---|---|---|
| WO | 95/22625 | A1 | 8/1995 |
| WO | 95/33836 | A1 | 12/1995 |
| WO | 96/00787 | A1 | 1/1996 |
| WO | 97/0078 | A1 | 1/1997 |
| WO | 97/35966 | A1 | 10/1997 |
| WO | 98/27230 | A1 | 6/1998 |
| WO | 2000/42651 | A1 | 7/2000 |
| WO | 2001/75767 | A2 | 10/2001 |
| WO | 2005/005633 | A2 | 1/2005 |
| WO | 2008/127646 | A2 | 10/2008 |
| WO | 2009/008908 | A2 | 1/2009 |
| WO | 2010/081053 | A2 | 7/2010 |
| WO | 2011/017551 | A1 | 2/2011 |
| WO | 2011/159910 | A2 | 12/2011 |
| WO | 2013/142770 | A1 | 9/2013 |

OTHER PUBLICATIONS

Georgescu R et al. Saturation Mutagenesis. 2003. Methods in Molecular Biology, vol. 231: Directed Evolution Library Creation: Methods and Protocols. Humana Press, Inc. p. 75-81.*

Midelfort, K.S., et al., "Redesigning and characterizing the substrate specificity and activity of Vibrio fluvialis aminotransferase for the synthesis of imagabalin," Protein Engineering Design and Selection, 26(1):25-33 [Sep. 25, 2012].

"Enzymatic synthesis of chiral amines with omega-transaminase," IP.com Journal, IP.com Inc., West Henrietta, NY, US [Feb. 17, 2010].

Shin, J.S., et al., "Purification, characterization, and molecular cloning of a novel amine:pyruvate transaminase from Vibrio fluvialis JS17," Appl. Microbiol. Biotechnol., 61(5-6):463-471 [2003].

Simonen, M., et al., "Protein Secretion in *Bacillus* Species," Microbiological Reviews, 57:109-137 (1993).

Smith, M., "In vitro mutagenesis," Ann. Rev. Genet., 19:423-462 (1985).

Smith, T., et al., "Comparison of Biosequences," Adv. Appl. Math, 2:482-489 (1981).

Stemmer, W., "DNA Shuffling by Random Fragmentation and Reassembly: In vitro Recombination for Molecular Evolution," Proc. Natl. Acad. Sci. USA, 91:10747-10751 (1994).

Stemmer, W.P.C., "Rapid evolution of a protein in vitro by DNA shuffling", Nature, 370:389-391 (1994).

(Continued)

*Primary Examiner* — Paul J Holland

(74) *Attorney, Agent, or Firm* — Codexis, Inc.

(57) ABSTRACT

The present disclosure provides engineered transaminase polypeptides for the production of amines, polynucleotides encoding the engineered transaminases, host cells capable of expressing the engineered transaminases, and methods of using the engineered transaminases to prepare compounds useful in the production of active pharmaceutical agents.

38 Claims, No Drawings

(56) References Cited

OTHER PUBLICATIONS

Stenico, M., et al., "Codon usage in Caenorhabditis elegans: delineation of translational selection and mutational biases," Nucl. Acids Res. 22(13):2437-46 [1994].
Streitwieser, Jr., A., et al., Introduction to Organic Chemistry, 2nd ed., pp. 169-171 (1981).
Suggs, S.V., et al., "Use of synthetic oligodeoxyribonucleotides for the isolation of specific cloned DNA sequenes," In Developmental Biology Using Purified Genes (Brown et al., eds.), pp. 683-693, Academic Press (1981).
Tiwari, S., et al., "Prediction of probable genes by Fourier analysis of genomic sequences," Comput. Appl. Biosci. 13(3):263-270 [1997].
Truppo, M.D., et al., "Development of an Improved Immobilized CAL-B for the Enzymatic Resolution of a Key Intermediate to Odanacatib," Organic Process Research & Development, 15:1033-1035 (2011).
Uberbacher, E.C., et al., "Discovering and Understanding Genes in Human DNA Sequence Using GRAIL," Methods Enzymol., 266:259-281 [1996].
Van Ophem, P.W., et al., "Substrate inhibition of D-amino acid transaminase and protection by salts and by reduced nicotinamide adenine dinucleotide: isolation and initial characterization of a pyridoxo intermediate related to inactivation.," Biochemistry 37(9):2879-88 (1998).
Villa-Komaroff, L., et al., "A bacterial clone synthesizing proinsulin," Proc. Natl Acad. Sci. USA, 75:3727-3731 (1978).
Wada, K., et al., "Codon usage tabulated from the GenBank genetic sequence data," Nucl. Acids Res., 20:2111-2118 [1992].
Wells, J.A., et al., "Cassette mutagenesis: an efficient method for generation of multiple mutations at defined sites," Gene, 34:315-323 (1985).
Wetmur, J. G., "DNA Probes: Applications of the Principles of Nucleic Acid Hybridization," Crit Rev Biochem Mol Biol, 26(3/4):227-259 (1991).
Wright, F., "The 'effective number of codons' used in a gene," Gene 87:23-29 [1990].
Yi, S., et al., "Covalent immobilization of omega-transaminase from Vibrio fluvialis JS17 on chitosan beads," Process Biochemistry 42(5): 895-898 (2007).
Yonaha, K., et al., "Distribution of ω--Amino Acid : Pyruvate Transaminase and Aminobutyrate : α-Ketoglutarate Transaminase in Microorganisms," Agric. Biol. Chem., 47 (10):2257-2265 [1983].
Yun, H., et al., "Asymmetric synthesis of (S)-alpha-methylbenzylamine by recombinant *Escherichia coli* co-expressing omega-transaminase and acetolactate synthase," Biosci. Biotechnol. Biochem., 72(11):3030-3033 [2008].
Yun, H., et al., "Kinetic resolution of (R,S)-sec-butylamine using omega-transaminase from Vibrio fluvialis JS17 under reduced pressure," Biotechnol. Bioeng., 87:772-778 [2004].
Yun, H., et al., "Use of Enrichment Culture for Directed Evolution of the Vibrio fluvialis JS17 omega-Transaminase, Which Is Resistant to Product Inhibition by Aliphatic Ketones," Appl Environ Micriobiol., 71(8):4220-4224 [2005].
Yun, H., et al., "ω--Amino Acid:Pyruvate Transaminase from Alcaligenes denitrificans Y2k-2: a New Catalyst for Kinetic Resolution of β-Amino Acids and Amines ," Appl. Environ. Microbiol., 70:2529-2534 [2004].
Zhang, J-H., et al., "Directed evolution of a fucosidase from a galactosidase by DNA shuffling and screening ,"Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
Zhong, S., et al., "5-Chloro-7-iodo-8-quinolinolatomanganese(III) with the Feature of pH-Regulated Molecular Switches as a Highly Efficient Catalyst for Epoxidation of Olefins with Hydrogen Peroxide," Adv. Synth. Catal., 350:802-807 [2008].
Zhu, D., et al., "Biocatalytic asymmetric amination of carbonyl functional groups—a synthetic biology approach to organic chemistry," Biotechnol J., 4(10):1420-31 (2009).
Genbank Accession No. ABA47738.1 dated Jan. 31, 2014.
Genbank Accession No. AEA39183.1 dated Apr. 4, 2011.
Genbank Accession No. AM902716.1 dated Feb. 27, 2015.
Ncbi Accession No. YP_002257813 dated Aug. 27, 2013.
Altschul, S., et al., "Basic local alignment search tool," J. Mol. Biol., 215: 403-410 (1990).
Altschul, S.F., et al., "Gapped Blast and PSI-Blast: a new generation of protein database search programs," Nucleic Acids Res., 25(17):3389-3402 (1997).
Baldino, Jr., F., et al., "High-Resolution in Situ Hybridization Histochemistry," Methods Enzymology, 168:761-777 (1989).
Batzer, M.A., "Erratum: Structure and variability of recently inserted Alu family members", Nucleic Acids Res 19:698-699 [1991].
Beaucage, S.L., et al., "Deoxynucleoside phosphoamidites—A new class of key intermediates for deoxypolynucleotide synthesis," Tetrahedron Letters, 22(20):1859-62 (1981).
Black, M.E., et al., "Creation of drug-specific herpes simplex virus type 1 thymidine kinase mutants for gene therapy," Proc Natl Acad Sci USA, 93:3525-3529 (1996).
Bolton, E.T., et al., "A General Method for the Iisolation of RNA Complementary to DNA," Proc. Natl. Acad. Sci. USA 48:1390 (1962).
Botstein, D., et al., "Strategies and applications of in vitro mutagenesis," Science, 229(4719):1193-1201 [1985].
Bray, P., et al., "Human cDNA clones for four species of G., signal transduction protein," Proc. Natl. Acad. Sci USA, 83:8893-8897 [1986].
Caldwell, R.C., et al., "Mutagenic PCR," PCR Methods Appl., 3:S136-S140 (1994).
Carey, F., Organic Chemistry, 2nd ed., pp. 328-331 [1992].
Carter, P., "Site-directed mutagenesis," Biochem. J., 237:1-7 (1986).
Cho, B.K., et al., "Redesigning the substrate specificity of omega-aminotransferase for the kinetic resolution of aliphatic chiral amines," Biotechnol Bioeng. 99(2):275-84 [2008].
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling,"Nat. Biotechnol., 14(3):315-319 (1996).
Crameri, A., et al., "Molecular evolution of an arsenate detoxification pathway by DNA shuffling," Nat. Biotechnol., 15(5):436-438 (1997).
Dale, S.J., et al "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Fasman, G.D.,CRC Practical Handbook of Biochemistry and Molecular Biology, CRC Press, Boca Raton, FL, pp. 3-70 [1989].
Freier, S.M., et al., "Improved free-energy parameters for predictions of RNA duplex stability," Proc. Natl. Acad. Sci USA, 83:9373-9377 (1986).
Guo, Z., et al., "3'-End-Forming Signals of Yeast mRNA," Mol. Cell. Biol., 15(11):5983-5990 [1995].
Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.
Henikoff, S.,et al., "Amino acid substitution matrices from protein blocks," Proc. Natl. Acad. Sci., 89:10915-10919 (1992).
Höhne, M., et al., "Biocatalytic Routes to Optically Active Amines," Chem. Cat. Chem., 1(1):42-51 [2009].

(56) References Cited

OTHER PUBLICATIONS

Höhne, M., et al., "Efficient Asymmetric Synthesis of Chiral Amines by Combining Transaminase and Pyruvate Decarboxylase", ChemBioChem, 9:363-365 (2008).
Hwang, B.-Y., et al., "High-throughput screening method for the identification of active and enantioselective ω--transaminases", Enzyme and Microbial Technology, 34:429-436, 2004.
Iwasaki, A., et al., "Microbial synthesis of (R)- and (S)-3,4-dimethoxyamphetamines through stereoselective transamination," Biotech. Lett., 25:1843-1846 [2003].
Iwasaki, A., et al., "Microbial synthesis of chiral amines by (R)-specific transamination with *Arthrobacter* sp. KNK168," Appl. Microbiol. Biotechnol., 69: 499-505 (2006).
Kierzek, R., et al., "Polymer-Supported RNA Synthesis and Its Application to Test the Nearest-Neighbor Model for Duplex Stability," Biochemistry, 25:7840-7846 (1986).
Koszelewski, D., et al., "Asymmetric Synthesis of Optically Pure Pharmacologically Relevant Amines Employing ω--Transaminases", Adv. Synth. Catal., 350:2761-2766 (2008).
Koszelewski, D., et al., "Deracemization of mexiletine biocatalyzed by omega-transaminases," Org. Lett., 11(21):4810-2 (2009).
Koszelewski, D., et al., "Immobilization of omega-transaminases by encapsulation in a sol-gel/celite matrix," Journal of Molecular Catalysis B: Enzymatic, 63: 39-44 (2010).
Kramer, B., et al., "Different base/base mismatches are corrected with different efficiencies by the methyl-directed DNA mismatch-repair system of *E. coli*," Cell, 38(3):879-887, 1984.
Ling, M., et al., "Approaches to DNA Mutagenesis:An Overview," Anal. Biochem., 254:157-78 (1997).
Martin, A.R., et al., "Characterization of free and immobilized (S)-aminotransferase for acetophenone production," Applied Microbiology and Biotechnology, 76(4): 843-851 (2007).
Mateo, C., et al., "Epoxy sepabeads: a novel epoxy support for stabilization of industrial enzymes via very intense multipoint covalent attachment," Biotechnology Progress 18(3):629-34 (2002).
Matthes, H.W.D., et al., "Simultaneous rapid chemical synthesis of over one hundred oligonucleotides on a microscale," EMBO J., 3(4):801-05 (1984).
McInerney, J.O., "GCUA: general codon usage analysis," Bioinformatics, 14(4):372-73 [1998].
Minshull, J., et al., "Protein evolution by molecular breeding," Curr. Op. Chem. Biol., 3(3):284-290 (1999).
Nakamura, Y., et al., "Codon usage tabulated from international DNA sequence databases: status for the year 2000," Nucl. Acids Res., 28:292 [2000].
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Romanos, M.A., et al., "Foreign gene expression in yeast: a review," Yeast 8:423-488 [1992].
Rychlik, W., et al., "Optimization of the annealing temperature for DNA amplification in vitro," Nucleic Acids Res, 18(21):6409-6412 (1990).
Shin, J.S., et al., "Asymmetric synthesis of chiral amines with omega-transaminase," Biotechnol. Bioeng. 65(2): 206-211 [1999].
Shin, J.S., et al., "Comparison of the omega-transaminases from different microorganisms and application to production of chiral amines," Biosci. Biotechnol. Biochem. 65:1782-1788 (2001).
Shin, J.S., et al., "Exploring the active site of amine:pyruvate aminotransferase on the basis of the substrate structure-reactivity relationship: how the enzyme controls substrate specificity and stereoselectivity," J. Org. Chem., 67(9):2848-2853 [2002].
Shin, J.S., et al., "Kinetic resolution of alpha-methylbenzylamine with omicron-transaminase screened from soil microorganisms: application of a biphasic system to overcome product inhibition," Biotechnol. Bioeng. 55(2):348-358 [1997].
Shin, J.S., et al., "Kinetic resolution of chiral amines with omega-transaminase using an enzyme-membrane reactor," Biotechnol Bioeng, 73(3):179-187 [2001].

* cited by examiner

SEQUENCE LISTING

```
<160> NUMBER OF SEQ ID NOS: 204

<210> SEQ ID NO 1
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 1

atgaacaaac cgcagagctg ggaaacgcgt gcggaaacct atagcctgta tggttttacc      60

gatatgccga gcctgcatca gcgtggcacc gtggtggtga cccatggcga aggcccgtat     120

atcgtggatg tgcatggccg tcgttatctg gatgcgaaca gcggcctgtt gaacatggtg     180

gcgggctttg atcataaagg cctgattgat gcggcgaaag cgcagtatga acgttttccg     240

ggctatcatg cgttttccgg ccgtatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggcgcga ccgcggtgag cgcgagcatg     480

accggcaaac cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcgaagaatt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080
```

-continued

```
aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgct gggccagagc   1260

gtggttctgt gcccgccgtt tattctgacc gaagcgcaga tggatgaaat gttcgataaa   1320

ctggaaaaag cgctggataa agtgtttgcg gaagtggcgt aa                       1362


<210> SEQ ID NO 2
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 2

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320
```

```
Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 3
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 3

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcgaatt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagcgg tgaaagataa agcgagcaaa gccccgtttg atggcaacct gagcgtgagc    1200

gaacgtattg cgaacacctg caccgatctg ggcctgattt gccgtccgac aggccagagc    1260
```

gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 4
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 4

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu

```
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 5
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 5

atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgatga gcggcgcttt gaacatggtg    180

gcgggctttg atcataaagg cctgattgat gcggcgaaag cgcagtatga acgttttccg    240

ggctatcatg cgttttgcgg ctatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgaccctgtg gaacgcgtat catggctgca ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt cattctgacc gaagcgcaga tggatgaaat gttcgataaa   1320

ctggaaaaag cgctggataa agtgtttgcg gaagtggcg                          1359
```

<210> SEQ ID NO 6
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 6

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365
```

```
Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 7
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 7

atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgatga gcggcgcttt gaacatggtg    180

gcgggctttg atcataaagg cctgattgat gcggcgaaag cgcagtatga acgttttccg    240

ggctatcatg cgttttgcgg ctatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgaccctgtg gaacgcgtat catggctgca ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tggcggcggt gttattccgc cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt cattctgacc gaagcgcaga tggatgaaat gttcgataaa   1320

ctggaaaaag cgctggataa agtgtttgcg gaagtggcg                          1359


<210> SEQ ID NO 8
<211> LENGTH: 453
<212> TYPE: PRT
<213> ORGANISM: Artificial Sequence
```

<220> FEATURE:
<223> OTHER INFORMATION: Engineered variant of V. fluvialis transaminase

<400> SEQUENCE: 8

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400
```

Glu Arg Ile Ala Asn Thr Cys Thr Asp Leu Gly Leu Ile Cys Arg Pro
405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 9
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 9
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgatga gcggcgcttt gaacatggtg 180
gcgggctttg atcataaagg cctgattgat gcggcgaaag cgcagtatga acgttttccg 240
ggctatcatg cgttttgcgg ctatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgaccctgtg gaacgcgtat catggctgca ccgtagtgag cgcgagcatg 480
accggctttc cgttcaacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccggg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtggtgtgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacatcc gaacattggc gaatatcgtg gcattggctt tatgtgggcg 1140
ctggaagttg tgaaagataa agcgagcaaa gccccgtttg atggcaacct gagcgtgagc 1200
gaacgtattg cgaacacctg caccgatctg ggcctgattt gcgctccgac aggccagagc 1260
gtggttctgt gcccgccgtt cattctgacc gaagcgcaga tggatgaaat gttcgataaa 1320
ctggaaaaag cgctggataa agtgtttgcg gaagtggcg 1359

<210> SEQ ID NO 10
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 10

-continued

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Ala Pro
                405                 410                 415

Thr Gly Gln Ser Val Val Leu Cys Pro Pro Phe Ile Leu Thr Glu Ala
```

-continued

```
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 11
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 11

```
atgaacaaac cgcagagctg ggaaacgcgt gcggaaacct atagcctgta tggttttacc      60
gatatgccga gcctgcatca gcgtggcacc gtggtggtgg cccatggcga aggcccgtat     120
atcgtggatg tgcatggccg tcgttatctg gatgcgatga gcggcgcttt gaacatggtg     180
gcgggctttg atcataaagg cctgattgat gcggcgaaag cgcagtatga acgttttccg     240
ggctatcatg cgttttgcgg ctatatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgaccctgtg gaacgcgtat catggctgca ccgtagtgag cgcgagcatg     480
accggctttc cgttcaacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgctggcggt gttattccgc cggcgaaagg ctattttcag     720
gcgattctgc cgatcctgcg caaatatgat attccggtga tcagcgatga agtggtgtgc     780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcggcgaatt tccgcatggt     960
tttaccgcgg gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt tatgtgggcg    1140
ctggaagttg tgaaagataa agcgagcaaa gccccgtttg atggcaacct gagcgtgagc    1200
gaacgtattg cgaacacctg caccgatctg ggcctgattt gcgctccgac aggccagagc    1260
gtggttctgt gcccgccgtt cattctgacc gaagcgcaga tggatgaaat gttcgataaa    1320
ctggaaaaag cgctggataa agtgtttgcg gaagtggcg                           1359
```

<210> SEQ ID NO 12
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 12

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30
```

-continued

```
Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Ala Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445
```

Phe Ala Glu Val Ala
450

<210> SEQ ID NO 13
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 13
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgatga gcggcgcttt gaacatggtg 180
gcgggctttg atcataaagg cctgattgat gcggcgaaag cgcagtatga acgttttccg 240
ggctatcatg cgttttgcgg ctatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgaccctgtg gaacgcgtat catggctgca ccgtagtgag cgcgagcatg 480
accggctttc cgttcaacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tggcggcggt gttattccgc cggcgaaagg ctattttcag 720
gcgattctgc cgatcctgcg caaatatgat attccggtga tcagcgatga agtggtgtgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacatcc gaacattggc gaatatcgtg gcattggctt tatgtgggcg 1140
ctggaagttg tgaaagataa agcgagcaaa gccccgtttg atggcaacct gagcgtgagc 1200
gaacgtattg cgaacacctg caccgatctg ggcctgattt gcgttccgac aggccagagc 1260
gtggttctgt gcccgccgtt cattctgacc gaagcgcaga tggatgaaat gttcgataaa 1320
ctggaaaaag cgctggataa agtgtttgcg gaagtggcg 1359

<210> SEQ ID NO 14
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 14

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Met Ser Gly Ala Leu Asn Met Val Ala Gly Phe Asp

-continued

```
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Val Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 15

-continued

<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 15

```
atgaacaaac cgcagagctg ggaaacgcgt gcggaaacct atagcctgta tggttttacc      60
gatatgccga gcctgcatca gcgtggcacc gtggtggtgg cccatggcga aggcccgtat     120
atcgtggatg tgcatggccg tcgttatctg gatgcgatga gcggcgcttt gaacatggtg     180
gcgggctttg atcataaagg cctgattgat gcggcgaaag cgcagtatga acgttttccg     240
ggctatcatg cgttttgcgg ctatatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgaccctgtg gaacgcgtat catggctgca ccgtagtgag cgcgagcatg     480
accggctttc cgttcaacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tggcggcggt gttattccgc cggcgaaagg ctattttcag     720
gcgattctgc cgatcctgcg caaatatgat attccggtga tcagcgatga agtggtgtgc     780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcggcgaatt tccgcatggt     960
tttaccgcgg gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacatcc gaacattggc gaatatcgtg gcattggctt tatgtgggcg    1140
ctggaagttg tgaaagataa agcgagcaaa gccccgtttg atggcaacct gagcgtgagc    1200
gaacgtattg cgaacacctg caccgatctg ggcctgattt gcgctccgac aggccagagc    1260
gtggttctgt gcccgccgtt cattctgacc gaagcgcaga tggatgaaat gttcgataaa    1320
ctggaaaaag cgctggataa agtgtttgcg gaagtggcg                            1359
```

<210> SEQ ID NO 16
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 16

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80
```

-continued

```
Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Ala Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 17
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 17

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgatga gcggcgcttt gaacatggtg    180

gcgggctttg atcataaagg cctgattgat gcggcgaaag cgcagtatga acgttttccg    240

ggctatcatg cgttttgcgg ctatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgaccctgtg gaacgcgtat catggctgca ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gcggtccgac aggccagagc   1260

gtggttctgt gcccgccgtt cattctgacc gaagcgcaga tggatgaaat gttcgataaa   1320

ctggaaaaag cgctggataa agtgtttgcg gaagtggcg                           1359
```

<210> SEQ ID NO 18
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 18

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110
```

```
Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Gly Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 19
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 19

```
atgaacaaac cgcagagctg ggaaacgcgt gcggaaacct atagcctgta tggttttacc      60
```

-continued

```
gatatgccga gcctgcatca gcgtggcacc gtggtggtgg cccatggcga aggcccgtat    120

atcgtggatg tgcatggccg tcgttatctg gatgcgatga gcggcgcttt gaacatggtg    180

gcgggctttg atcataaagg cctgattgat gcggcgaaag cgcagtatga acgttttccg    240

ggctatcatg cgttttgcgg ctatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgaccctgtg gaacgcgtat catggctgca ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tggcggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt cattctgacc gaagcgcaga tggatgaaat gttcgataaa   1320

ctggaaaaag cgctggataa agtgtttgcg gaagtggcg                          1359
```

```
<210> SEQ ID NO 20
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 20

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
```

130 135 140

Thr Leu Trp Asn Ala Tyr His Gly Cys Thr Val Val Ser Ala Ser Met
145 150 155 160

Thr Gly Phe Pro Phe Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Gly Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu His Pro Asn
355 360 365

Ile Gly Glu Tyr Arg Gly Ile Gly Phe Met Trp Ala Leu Glu Val Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 21
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 21
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgatga gcggcgcttt gaacatggtg 180
gcgggctttg atcataaagg cctgattgat gcggcgaaag cgcagtatga acgttttccg 240

```
ggctatcatg cgttttgcgg ctatatgagc gatcagaccg tgatgctgtc tgaaaaactg    300

gtggaagtga gcccgtttga tagcggccgt gtgttttaca ccaacagcgg cagcgaagcg    360

aacgatacca tggtgaaaat gctgtggttt ctgcatgcgg cggaaggcaa accgcagaag    420

cgtaaaattc tgaccctgtg gaacgcgtat catggctgca ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gcgttccgac aggccagagc   1260

gtggtactgt gcccgccgtt cattctgacc gaagcgcaga tggatgaaat gttcgataaa   1320

ctggaaaaag cgctggataa agtgtttgcg gaagtggcg                          1359
```

<210> SEQ ID NO 22
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 22

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160
```

-continued

Thr Gly Phe Pro Phe Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Val Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu His Pro Asn
355 360 365

Ile Gly Glu Tyr Arg Gly Ile Gly Phe Met Trp Ala Leu Glu Val Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Val Pro
405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 23
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 23
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgatga gcggcgcttt gaacatggtg 180
gcgggctttg atcataaagg cctgattgat gcggcgaaag cgcagtatga acgttttccg 240
ggctatcatg cgttttgcgg ctatatgagc gatcagaccg tgatgctgtc tgaaaaactg 300
gtggaagtga gcccgtttga tagcggccgt gtgttttata ccaacagcgg cagcgaagcg 360

```
aacgatacca tggtgaaaat gctgtggttt ctgcatgcgg cggaaggcaa accgcagaaa    420

cgtaaaattc tgaccctgtg gaacgcgtat catggctgca ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tggcggcggt gttattccgc cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttgc cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gcggtccgac aggccagagc   1260

gtggttctgt gcccgccgtt cattctgacc gaagcgcaga tggatgaaat gttcgataaa   1320

ctggaaaaag cgctggataa agtgtttgcg gaagtggcg                           1359


<210> SEQ ID NO 24
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 24

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190
```

```
Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Ala Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Gly Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 25
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 25

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgatga gcggcgcttt gaacatggtg     180

gcgggctttg atcataaagg cctgattgat gcggcgaaag cgcagtatga acgttttccg     240

ggctatcatg cgttttgcgg ctatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgaccctgtg gaacgcgtat catggctgca ccgtagtgag cgcgagcatg     480

accggctttc cgttcaacag cgtgtttggc ctgccgctgc cgggctttct gcatctgacc     540
```

```
tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt cattctgacc gaagcgcaga tggatgaaat gttcgataaa   1320

ctggaaaaag cgctggataa agtgtttgcg gaagtggcg                          1359


<210> SEQ ID NO 26
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 26

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
```

```
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 27
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 27

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgatga gcggcgcttt gaacatggtg     180

gcgggctttg atcataaagg cctgattgat gcggcgaaag cgcagtatga acgttttccg     240

ggctatcatg cgttttgcgg ctatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgaccctgtg gaacgcgtat catggctgca ccgtagtgag cgcgagcatg     480

accggctttc cgttcaacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660
```

```
tttgcggaac cggtgatggg tggcggcggt gttattccgc cggcgaaagg ctattttcag    720

gcgattctgc cgatcctgcg caaatatgat gttccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgcgagc   1200

gaacgtattg cgaacacctg caccgatctg ggcctgattt gccgtccgac aggccagagc   1260

gtggttctgt gcccgccgtt cattctgacc gaagcgcaga tggatgaaat gttcgataaa   1320

ctggaaaaag cgctggataa agtgtttgcg gaagtggcg                          1359
```

```
<210> SEQ ID NO 28
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 28

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Gly Val Ile Pro Pro Ala Lys Gly Tyr Phe Gln
225                 230                 235                 240
```

-continued

```
Ala Ile Leu Pro Ile Leu Arg Lys Tyr Asp Val Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Ala Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 29
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 29

```
atgaacaaac cgcagagctg ggaaacgcgt gcggaaacct atagcctgta tgcgtttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgctg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattacac cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840
```

```
attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 30
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 30

```
Met Asn Lys Pro Gln Ser Trp Glu Thr Arg Ala Glu Thr Tyr Ser Leu
1               5                   10                  15

Tyr Ala Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

```
Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 31
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 31

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgctg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattacac cggcgaaagg ctattttcag    720

gcgattctga ctatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960
```

```
tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

```
<210> SEQ ID NO 32
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 32

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
```

```
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 33
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 33

atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgctg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140
```

-continued

```
ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgg caccgccgtt tattctgacc gaagcgcaga tggatgaaat gttcgataaa   1320

ctggaaaaag cgctggataa agtgtttgcg gaagtggcg                        1359


<210> SEQ ID NO 34
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 34

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320
```

```
Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 35
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 35

atgaacaaac cgcagagctg ggaaacgcgt gcggaaacct atagcctgta tgggtttacc     60

catatgccga gcctgcatca gcgtggcacc atggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctga ctatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260
```

-continued

```
gtggttctgt gcccgccgtt tattctgacc gaagcgcaga tggatgaaat gttcgataaa   1320

ctggaaaaag cgctggataa agtgtttgcg gaagtggcg                          1359


<210> SEQ ID NO 36
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 36

Met Asn Lys Pro Gln Ser Trp Glu Thr Arg Ala Glu Thr Tyr Ser Leu
1               5                   10                  15

Tyr Gly Phe Thr His Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350
```

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 37
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 37
atgaacaaac cgcagagctg ggaaacgcgt gcggaaacct atagcctgta tgggtttacc 60
gatatgccga gcctgcatca gcgtggcacc atggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagtcg tgaaagataa agcgagcaaa gcccccgtttg atggcaacct gagcgtgagc 1200
gaacgtattg cgaacacctg caccgatctg ggcctgattt gccgtccgac aggccagagc 1260
gtggttctgt gcccgccgta tattctgacc gaagcgcaga tggatgaaat gttcgataaa 1320
ctggaaaaag cgctggataa agtgtttgcg gaagtggcg 1359

-continued

<210> SEQ ID NO 38
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 38

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
```

-continued

```
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 39
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 39

```
atgaacaaac cgcagagctg ggaaacgcgt gcggaaacct atagcctgta tgggtttacc     60
gatatgccga gcctgcatca gcgtggcacc atggtggtgg cccatggcga aggcccgtat    120
atcgtggatg tgcatggccg tcgttatctg gatgcgaaca gcggcgcttt gaacatggtg    180
gcgggctttg atcataaagg cctgattgat gcggcgaaag cgcagtatga acgttttccg    240
ggctatcatg cgttttcagg ccatatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggctgta ccgtagtgag cgcgagcatg    480
accggctttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgctggcggt gttattacac cggcgaaagg ctattttcag    720
gcgattctgc cgatcctgcg caaatatgat attccggtga tcagcgatga agtgatttgc    780
ggctttggcc gtaccggtaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcggcgaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaagtcg tgaaagataa agcgagcaaa gccccgtttg atggcaacct gagcgtgagc   1200
gaacgtattg cgaacacctg caccgatctg ggcctgattt gccgtccgac aggccagagc   1260
gtggttctgg caccgccgtt tattctgacc gaagcgcaga tggatgaaat gttcgataaa   1320
ctggaaaaag cgctggataa agtgtttgcg gaagtggcg                           1359
```

<210> SEQ ID NO 40
<211> LENGTH: 453
<212> TYPE: PRT
<213> ORGANISM: Artificial Sequence
<220> FEATURE:

-continued

<223> OTHER INFORMATION: Engineered variant of V. fluvialis transaminase

<400> SEQUENCE: 40

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Val Val
370 375 380

Lys Asp Lys Ala Ser Lys Ala Pro Phe Asp Gly Asn Leu Ser Val Ser
385 390 395 400

```
Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 41
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 41

```
atgaacaaac cgcagagctg ggaaacgcgt gcggaaacct atagcctgta tgggtttacc     60

catatgccga gcctgcatca gcgtggcacc atggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgaccctgtg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattacac cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 42
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 42

```
Met Asn Lys Pro Gln Ser Trp Glu Thr Arg Ala Glu Thr Tyr Ser Leu
```

-continued

```
1               5                   10                  15

Tyr Gly Phe Thr His Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430
```

Gln Met Asp Glu Met Phe Asp Lys Leu Glu Lys Ala Leu Asp Lys Val
435 440 445

Phe Ala Glu Val Ala
450

<210> SEQ ID NO 43
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 43
atgaacaaac cgcagagctg ggaaacgcgt gcggaaacct atagcctgta tggttttacc 60
gatatgccga gcctgcatca gcgtggcacc atggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgctg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagtcg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 44
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 44

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

-continued

```
Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
```

450

<210> SEQ ID NO 45
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 45
atgaacaaac cgcagagctg ggaaacgcgt gcggaaacct atagcctgta tgggtttacc 60
gatatgccga gcctgcatca gcgtggcacc atggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgctg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctga ctatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagtcg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 46
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 46

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Thr Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Val Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 47
<211> LENGTH: 1359

-continued

<212> TYPE: DNA
<213> ORGANISM: Artificial Sequence
<220> FEATURE:
<223> OTHER INFORMATION: Engineered variant of V. fluvialis transaminase

<400> SEQUENCE: 47
atgaacaaac cgcagagctg ggaaacgcgt gcggaaacct atagcctgta tgggtttacc 60
gatatgccga gcctgcatca gcgtggcacc atggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgaccctgtg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattacac cgccgaaagg ctattttcag 720
gcgattctga ctatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagtcg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgg caccgccgta tattctgacc gaagcgcaga tggatgaaat gttcgataaa 1320
ctggaaaaag cgctggataa agtgtttgcg gaagtggcg 1359

<210> SEQ ID NO 48
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 48

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu

```
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 49
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 49
atgaacaaac cgcagagctg ggaaacgcgt gcggaaacct atagcctgta tggttttacc 60
gatatgccga gcctgcatca gcgtggcacc atggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagtcg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgg caccgccgta tattctgacc gaagcgcaga tggatgaaat gttcgataaa 1320
ctggaaaaag cgctggataa agtgtttgcg gaagtggcg 1359

<210> SEQ ID NO 50
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 50

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

```
Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 51
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 51

```
atgaacaaac cgcagagctg ggaaacgcgt gcggaaacct atagcctgta tggttttacc      60

gatatgccga gcctgcatca gcgtggcacc atggtggtgg cccatggcga aggcccgtat     120
```

```
atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgctg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattacac cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgta tattctgacc gaagcgcaga tggatgaaat gttcgataaa   1320

ctggaaaaag cgctggataa agtgtttgcg gaagtggcg                          1359


<210> SEQ ID NO 52
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 52

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140
```

```
Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 53
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 53

```
atgaacaaac cgcagagctg ggaaacgcgt gcggaaacct atagcctgta tgggtttacc      60

gatatgccga gcctgcatca gcgtggcacc atggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240
```

-continued

```
ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgctg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattacac cggcgaaagg ctattttcag    720

gcgattctga ctatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgta tattctgacc gaagcgcaga tggatgaaat gttcgataaa   1320

ctggaaaaag cgctggataa agtgtttgcg gaagtggcg                          1359
```

<210> SEQ ID NO 54
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 54

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
```

```
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 55
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 55

```
atgaacaaac cgcagagctg ggaaacgcgt gcggaaacct atagcctgta tgggtttacc      60

gatatgccga gcctgcatca gcgtggcacc atggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420
```

```
cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattacac cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gcccccgtttg atggcaacct gagcgtgagc   1200

gaacgtattg cgaacacctg caccgatctg ggcctgattt gccgtccgac aggccagagc   1260

gtggttctgg caccgccgtt tattctgacc gaagcgcaga tggatgaaat gttcgataaa   1320

ctggaaaaag cgctggataa agtgtttgcg gaagtggcg                         1359
```

<210> SEQ ID NO 56
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 56

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190
```

-continued

```
Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 57
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 57

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcaaaaa    420

cgtaaaattc tgacccgctg gaacgcgtat catggctgta ccgtagtgag cgcgagcatg    480

accggctttc cgtataacag cgtgtttggc ctgccgctgc cgggctttct gcatctgacc    540
```

-continued

```
tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcgaatt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagtcg tgaaagataa agcgagcaaa gccccgtttg atggcaacct gagcgtgagc    1200

gaacgtattg cgaacacctg caccgatctg ggcctgattt gccgtccgac aggccagagc    1260

gtggttctgt gcccgccgtt tattctgacc gaagcgcaga tggatgaaat gttcgataaa    1320

ctggaaaaag cgctggataa agtgtttgcg gaagtggcg                           1359
```

```
<210> SEQ ID NO 58
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 58

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220
```

```
Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 59
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 59

```
atgaacaaac cgcagagctg ggaaacgcgt gcggaaacct atagcctgta tggttttacc      60

gatatgccga gcctgcatca gcgtggcacc atggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgcaa aaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattacac cggcgaaagg ctattttcag     720
```

gcgattctga ctatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagtcg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 60
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 60

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Lys Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Ala Lys Gly Tyr Phe Gln
225 230 235 240

Ala Ile Leu Thr Ile Leu Arg Lys Tyr Asp Ile Pro Val Ile Ser Asp 245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Val Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 61
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 61
atgaacaaac cgcagagctg ggaaacgcgt gcggaaacct atagcctgta tgggtttacc 60
gatatgccga gcctgcatca gcgtggcacc atggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840

-continued attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgg caccgccgtt tattctgacc gaagcgcaga tggatgaaat gttcgataaa 1320
ctggaaaaag cgctggataa agtgtttgcg gaagtggcg 1359

<210> SEQ ID NO 62
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 62

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

```
Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

```
<210> SEQ ID NO 63
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 63

atgaacaaac cgcagagctg ggaaacgcgt gcggaaacct atagcctgta tgggtttacc      60

catatgccga gcctgcatca gcgtggcacc atggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcgaatt tccgcatggt     960

tttaccgcgg gcggccatcc ggtgggttgt gcgattgcgc tgaaagcgat tgatgtggtg    1020
```

atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 64
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 64

Met Asn Lys Pro Gln Ser Trp Glu Thr Arg Ala Glu Thr Tyr Ser Leu
1 5 10 15

Tyr Gly Phe Thr His Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Ala Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 65
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 65
atgaacaaac cgcagagctg ggaaacgcgt gcggaaacct atagcctgta tgggtttacc 60
gatatgccga gcctgcatca gcgtggcacc atggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgaccctgtg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140

-continued

```
ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgta tattctgacc gaagcgcaga tggatgaaat gttcgataaa   1320

ctggaaaaag cgctggataa agtgtttgcg gaagtggcg                          1359
```

<210> SEQ ID NO 66
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 66

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
```

```
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 67
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 67

atgaacaaac cgcagagctg ggaaacgcgt gcggaaacct atagcctgta tgcgtttacc     60

gatatgccga gcctgcatca gcgtggcacc atggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgctg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattacac cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgg caccgccgtt tattctgacc gaagcgcaga tggatgaaat gttcgataaa   1320
```

ctggaaaaag cgctggataa agtgtttgcg gaagtggcg 1359

<210> SEQ ID NO 68
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 68

```
Met Asn Lys Pro Gln Ser Trp Glu Thr Arg Ala Glu Thr Tyr Ser Leu
1               5                   10                  15

Tyr Ala Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350
```

```
Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 69
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 69

atgaacaaac cgcagagctg ggaaacgcgt gcggaaacct atagcctgta tgggtttacc     60

catatgccga gcctgcatca gcgtggcacc atggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgctg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgta tattctgacc gaagcgcaga tggatgaaat gttcgataaa   1320

ctggaaaaag cgctggataa agtgtttgcg gaagtggcg                           1359


<210> SEQ ID NO 70
```

<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 70

```
Met Asn Lys Pro Gln Ser Trp Glu Thr Arg Ala Glu Thr Tyr Ser Leu
1               5                   10                  15

Tyr Gly Phe Thr His Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380
```

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Thr Gly Gln Ser Val Val Leu Cys Pro Pro Tyr Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 71
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 71
atgaacaaac cgcagagctg ggaaacgcgt gcggaaacct atagcctgta tggttggacc 60
gatatgccga gcctgcatca gcgtggcacc gtggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga aaaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 72
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 72

Met Asn Lys Pro Gln Ser Trp Glu Thr Arg Ala Glu Thr Tyr Ser Leu
1               5                   10                  15

Tyr Gly Trp Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Lys Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro

-continued 405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 73
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 73
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggctgttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 74
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 74

Met Asn Lys Pro Gln Ser Trp Glu Thr Arg Ala Glu Thr Tyr Ser Leu
1 5 10 15

```
Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Cys Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430
```

-continued

Gln Met Asp Glu Met Phe Asp Lys Leu Glu Lys Ala Leu Asp Lys Val
        435                 440                 445

Phe Ala Glu Val Ala
    450

<210> SEQ ID NO 75
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 75
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttt taacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 76
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 76

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg

-continued

```
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 77
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 77
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttg taacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 78
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 78

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Asn Ser Gly Ala Cys Asn Met Val Ala Gly Phe Asp
50 55 60

```
His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 79
<211> LENGTH: 1359
<212> TYPE: DNA

<213> ORGANISM: Artificial Sequence
<220> FEATURE:
<223> OTHER INFORMATION: Engineered variant of V. fluvialis transaminase

<400> SEQUENCE: 79

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgtttaatgg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 80
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 80

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asn Gly His Met Ser Asp Gln Thr Val Met Leu
                85                  90                  95
```

```
Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 81
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 81

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggccttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcgaatt tccgcatggt     960

tttaccacgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagcgg tgaaagataa agcgagcaaa gccccgtttg atggcaacct gagcgtgagc    1200

gaacgtattg cgaacacctg caccgatctg ggcctgattt gccgtccgac aggccagagc    1260

gtggttctgt gcccgccgtt tattctgacc gaagcgcaga cggatgaaat gttcgataaa    1320

ctggaaaaag cgctggataa agtgtttgcg gaagtggcg                           1359
```

<210> SEQ ID NO 82
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 82

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
```

```
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Thr Asp Glu Met Phe Asp Lys Leu Glu Lys Ala Leu Asp Lys Val
        435                 440                 445

Phe Ala Glu Val Ala
    450


<210> SEQ ID NO 83
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 83

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120
```

-continued

```
atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gcttgccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 84
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 84

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140
```

```
Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Leu Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 85
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 85

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300
```

gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccatccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 86
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 86

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

```
Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 87
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 87

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420
```

-continued

```
cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cgcctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaatttg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 88
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 88

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
```

-continued

```
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Ala Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Phe Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 89
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 89

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600
```

-continued

```
ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaacatct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 90
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 90

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220
```

-continued

```
Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys His Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 91
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 91

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720
```

-continued gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcagttt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 92
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 92

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

```
Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Ser Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 93
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 93

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900
```

-continued

```
ccggaactga gcaaacgtct ggaaaccgcg attgaagcga tcggctgttt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

```
<210> SEQ ID NO 94
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 94

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
```

-continued

```
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Cys Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 95
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 95

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020
```

```
atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atccgaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359


<210> SEQ ID NO 96
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 96

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300
```

-continued

```
Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Pro Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 97
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 97

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcacttt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200
```

```
gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359


<210> SEQ ID NO 98
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 98

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Thr Phe Pro His Gly
305                 310                 315                 320

Phe Thr Ala Gly Gly His Pro Val Gly Cys Ala Ile Ala Leu Lys Ala
                325                 330                 335
```

```
Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 99
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 99

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcaattt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagcgg tgaaagataa agcgagcaaa gccccgtttg atggcaacct gagcgtgagc    1200

gaacgtattg cgaacacctg caccgatctg ggcctgattt gccgtccgac aggccagagc    1260

gtggttctgt gcccgccgtt tattctgacc gaagcgcaga tggatgaaat gttcgataaa    1320
```

ctggaaaaag cgctggataa agtgtttgcg gaagtggcg 1359

<210> SEQ ID NO 100
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 100

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
```

```
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 101
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 101

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcttttt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagcgg tgaaagataa agcgagcaaa gccccgtttg atggcaacct gagcgtgagc    1200

gaacgtattg cgaacacctg caccgatctg ggcctgattt gccgtccgac aggccagagc    1260

gtggttctgt gcccgccgtt tattctgacc gaagcgcaga tggatgaaat gttcgataaa    1320

ctggaaaaag cgctggataa agtgtttgcg gaagtggcg                           1359


<210> SEQ ID NO 102
<211> LENGTH: 453
```

<212> TYPE: PRT
<213> ORGANISM: Artificial Sequence
<220> FEATURE:
<223> OTHER INFORMATION: Engineered variant of V. fluvialis transaminase

<400> SEQUENCE: 102

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Phe Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380
```

-continued

```
Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 103
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 103

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaatgtct aaccgcgggt ttttttccgg taggcgcggt gattctgggt     900

ccggaactga gcaaacgtct ggaaaccgcg attgaagcga tcggcgaatt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagcgg tgaaagataa agcgagcaaa gccccgtttg atggcaacct gagcgtgagc    1200

gaacgtattg cgaacacctg caccgatctg ggcctgattt gccgtccgac aggccagagc    1260

gtggttctgt gcccgccgtt tattctgacc gaagcgcaga tggatgaaat gttcgataaa    1320

ctggaaaaag cgctggataa agtgtttgcg gaagtggcg                           1359


<210> SEQ ID NO 104
<211> LENGTH: 453
<212> TYPE: PRT
<213> ORGANISM: Artificial Sequence
<220> FEATURE:
<223> OTHER INFORMATION: Engineered variant of V. fluvialis transaminase
```

<400> SEQUENCE: 104

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Cys Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Ala Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

```
Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 105
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 105

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttgg tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcgaatt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagcgg tgaaagataa agcgagcaaa gccccgtttg atggcaacct gagcgtgagc    1200

gaacgtattg cgaacacctg caccgatctg ggcctgattt gccgtccgac aggccagagc    1260

gtggttctgt gcccgccgtt tattctgacc gaagcgcaga tggatgaaat gttcgataaa    1320

ctggaaaaag cgctggataa agtgtttgcg gaagtggcg                          1359


<210> SEQ ID NO 106
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 106

Met Asn Lys Pro Gln Ser Trp Glu Thr Arg Ala Glu Thr Tyr Ser Leu
1               5                   10                  15
```

-continued

```
Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Gly Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
```

-continued

```
        435                 440                 445

Phe Ala Glu Val Ala
    450


<210> SEQ ID NO 107
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 107

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgtttccta ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcgaatt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagcgg tgaaagataa agcgagcaaa gccccgtttg atggcaacct gagcgtgagc    1200

gaacgtattg cgaacacctg caccgatctg ggcctgattt gccgtccgac aggccagagc    1260

gtggttctgt gcccgccgtt tattctgacc gaagcgcaga tggatgaaat gttcgataaa    1320

ctggaaaaag cgctggataa agtgtttgcg gaagtggcg                            1359


<210> SEQ ID NO 108
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 108

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45
```

-continued

```
Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Pro Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 109
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 109
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgtttctta ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 110
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 110

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro

```
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 111
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 111
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttgta ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagcgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 112
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 112

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

-continued

```
Ser Glu Lys Leu Val Glu Val Ser Pro Phe Asp Ser Gly Arg Val Phe
            100                 105                 110

Cys Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 113
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 113

```
atgaacaaac cgcagagctg ggaaacgcgt gcggaaacct atagcctgta tggttttacc     60
gatatgccga gcctgcatca gcgtggcacc gtggtggtgg cccatggcga aggcccgtat    120
atcgtggatg tgcatggccg tcgttatctg gatgcgaaca gcggcgcttt gaacatggtg    180
gcgggctttg atcataaagg cctgattgat gcggcgaaag cgcagtatga acgttttccg    240
ggctatcatg cgttttcagg ccatatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgtgt taacgcgtat catggctgta ccgtagtgag cgcgagcatg    480
accggctttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgctggcggt gttattccgc cggcgaaagg ctattttcag    720
gcgattctgc cgatcctgcg caaatatgat attccggtga tcagcgatga agtgatttgc    780
ggctttggcc gtaccggtaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcggcgaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgac aggccagagc   1260
gtggttctgt gcccgccgtt tattctgacc gaagcgcaga tggatgaaat gttcgataaa   1320
ctggaaaaag cgctggataa agtgtttgcg gaagtggcg                          1359
```

<210> SEQ ID NO 114
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 114

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125
```

```
Trp Phe Leu His Ala Ala Glu Gly Lys Pro Gln Lys Arg Lys Ile Leu
    130                 135                 140

Thr Arg Val Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 115
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 115

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180
```

```
gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgtca taacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

```
<210> SEQ ID NO 116
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 116

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg His Asn Ala Tyr His Gly Cys Thr Val Val Ser Ala Ser Met
```

```
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 117
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 117

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300
```

```
gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gtggctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359


<210> SEQ ID NO 118
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 118

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175
```

```
Leu Trp Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 119
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 119

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480
```

```
accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattgttc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 120
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 120

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205
```

-continued

```
Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 121
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 121

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600
```

-continued

```
ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccactg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 122
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 122

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
```

225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Thr Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Ala Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 123
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 123
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780

-continued

```
ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaactg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 124
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 124

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255
```

```
Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Thr Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 125
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 125

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900
```

-continued

```
ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgatta ttcgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 126
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 126

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285
```

```
Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Ile Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 127
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 127

atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgctggcggt gttattacgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcgaatt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080
```

```
aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359


<210> SEQ ID NO 128
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 128

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
```

-continued 305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Ala Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 129
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 129
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaatgtg tgaaagataa agcgagcaaa gccccgtttg atggcaacct gagcgtgagc 1200

```
gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359


<210> SEQ ID NO 130
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 130

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335
```

```
Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Cys Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 131
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 131

atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaattg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 132
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 132

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

```
Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 133
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 133

atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgaaca gcggcgcttt gaacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgcagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttagt gaagtggcg                          1359


<210> SEQ ID NO 134
<211> LENGTH: 453
<212> TYPE: PRT
```

<213> ORGANISM: Artificial Sequence
<220> FEATURE:
<223> OTHER INFORMATION: Engineered variant of V. fluvialis transaminase

<400> SEQUENCE: 134

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
```

-continued

```
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 135
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 135

```
atgaacaaac cgcagagctg ggaaacgcgt gcggaaacct atagcctgta tggttttacc      60

gatatgccga gcctgcatca gcgtggcacc gtggtggtgg cccatggcga aggcccgtat     120

atcgtggatg tgcatggccg tcgttatctg gatgcgaaca gcggcgcttt gaacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactgaagga aaccattcag aaggaaggcg cggataccat tgcgggcttt     660

tttgcggaac cggtgatggg tgctggcggt gttattccgc cggcgaaagg ctattttcag     720

gcgattctgc cgatcctgcg caaatatgat attccggtga tcagcgatga agtgatttgc     780

ggctttggcc gtaccggtaa cacctggggc tgcgtgacct atgattttac cccggatgcg     840

attattagca gtaaaaacct aaccgcgggt ttttttccgg taggcgcggt gattctgggt     900

ccggaactga gcaaacgtct ggaaaccgcg attgaagcga tcggcgcatt tccgcatggt     960

tttaccgcgg gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gcattggctt tatgtgggcg    1140

ctggaagcgg tgaaagataa agcgagcaaa gccccgtttg atggcaacct gagcgtgagc    1200

gaacgtattg cgaacacctg caccgatctg ggcctgattt gccgtccgac aggccagagc    1260

gtggttctgt gcccgccgtt tattctgacc gaagcgcaga tggatgaaat gttcgataaa    1320

ctggaaaaag cgctggataa agtgtttgcg gaagtggcg                           1359
```

<210> SEQ ID NO 136
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 136

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Lys Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Ala Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415
```

Thr Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 137
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 137
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaatttg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 138
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 138

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val

-continued

```
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Phe Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445
```

Phe Ala Glu Val Ala
450

<210> SEQ ID NO 139
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 139
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaaatgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 140
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 140

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

```
Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Met Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 141
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 141

```
atgaacaaac cgcagagctg ggaaacgcgt gcggaaacct atagcctgta tggttttacc     60
gatatgccga gcctgcatca gcgtggcacc gtggtggtgg cccatggcga aggcccgtat    120
atcgtggatg tgcatggccg tcgttatctg gatgcgaaca gcggcgcttt gaacatggtg    180
gcgggctttg atcataaagg cctgattgat gcggcgaaag cgcagtatga acgttttccg    240
ggctatcatg cgttttcagg ccatatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggctgta ccgtagtgag cgcgagcatg    480
accggctttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgctggcggt gttattccgc cggcgaaagg ctattttcag    720
gcgattctgc cgatcctgcg caaatatgat attccggtga tcagcgatga agtgatttgc    780
ggctttggcc gtaccggtaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcggcgaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccggt tggccagagc   1260
gtggttctgt gcccgccgtt tattctgacc gaagcgcaga tggatgaaat gttcgataaa   1320
ctggaaaaag cgctggataa agtgtttgcg gaagtggcg                          1359
```

<210> SEQ ID NO 142
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 142

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80
```

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Ala Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Val Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 143
<211> LENGTH: 1359
<212> TYPE: DNA
<213> ORGANISM: Artificial Sequence
<220> FEATURE:

-continued

<223> OTHER INFORMATION: Engineered variant of V. fluvialis transaminase

<400> SEQUENCE: 143
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgaaca gcggcgcttt gaacatggtg 180
gcgggctttg atcataaagg cctgattgat gcggcgagag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaactgg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 144
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 144

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Asn Ser Gly Ala Leu Asn Met Val Ala Gly Phe Asp
50 55 60

His Lys Gly Leu Ile Asp Ala Ala Arg Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe

-continued

```
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Leu Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 145
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 145

```
atgaacaaac cgcagagctg ggaaacgcgt gcggaaacct atagcctgta tggttttacc     60
```

```
gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaatgcct aaccgcgggt ttttttccgg taggcgcggt gattctgggt    900

ccggaactga gcaaacgtct ggaaaccgcg attgaagcga tcggcaattt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

```
<210> SEQ ID NO 146
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 146

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125
```

```
Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Cys Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 147
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 147

```
atgaacaaac cgcagagctg ggaaacgcgt gcggaaacct atagcctgta tggttttacc      60

gatatgccga gcctgcatca gcgtggcacc atggtggtgg cccatggcga aggcccgtat     120

atcgtggatg tgcatggccg tcgttatctg gatgcgaaca gcggcgcttt caacatggtg     180
```

-continued

```
gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcaaaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaattt tccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagtcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 148
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 148

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160
```

-continued

```
Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 149
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 149

```
atgaacaaac cgcagagctg ggaaacgcgt gcggaaacct atagcctgta tggttttacc      60

gatatgccga gcctgcatca gcgtggcacc atggtggtgg cccatggcga aggcccgtat     120

atcgtggatg tgcatggccg tcgttatctg gatgcgaaca gcggcgcttt caacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttgta ccaacagcgg cagcgaagcg     360
```

aacgatacca tggtgaaaat gctgtggttt ctgcatgcgg cggaaggcaa accgcagaaa 420
cgtaaaattc tgacccgtgt taacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaatgcct aaccgcgggt ttttttccgg taggcgcggt gattctgggt 900
ccggaactga gcaaacgtct ggaaaccgcg attgaagcga tcggcagctt tccgcatggt 960
tttaccacgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaaatgg tgaaagataa agcgagcaaa gccccgtttg atggcaacct gagcgtgagc 1200
gaacgtattg cgaacacctg caccgatctg ggcctgattt gccatccgac aggccagagc 1260
gtggttctgt gcccgccgtt tattctgacc gaagcgcaga tggatgaaat gttcgataaa 1320
ctggaaaaag cgctggataa agtgtttagc gaagtggcg 1359

<210> SEQ ID NO 150
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 150

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Phe Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Cys Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Val Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu

```
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Cys Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Ser Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Met Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450


<210> SEQ ID NO 151
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 151

atgaacaaac cgcagagctg ggaaacgcgt gcggaaacct atagcctgta tggttttacc      60

gatatgccga gcctgcatca gcgtggcacc atggtggtgg cccatggcga aggcccgtat     120

atcgtggatg tgcatggccg tcgttatctg gatgcgaaca gcggcgcttt caacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgtttctga ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggctgta ccgtagtgag cgcgagcatg     480
```

```
accggctttc cgtataacag cgtgtttggc ctgccgctgc cgggctttct gcatctgacc    540

tgcccgcatt attggcgtta tggcgaaaaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattgtcc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaattt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaatgg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttagc gaagtggcg                          1359
```

```
<210> SEQ ID NO 152
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 152

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Lys Gly Glu
            180                 185                 190

Thr Glu Glu Gln Phe Val Ala Arg Leu Ala Arg Glu Leu Glu Glu Thr
        195                 200                 205
```

```
Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Met Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 153
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 153

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttgg tagcggccgt gtgtttctga ccaacagcgg cagcgaagcg    360

aacgatacca tggtgaaaat gctgtggttt ctgcatgcgg cggaaggcaa accgcagaaa    420

cgtaaaattc tgacccgtgt taacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660
```

```
tttgcggaac cggtgatggg tgctggcggt gttattgtcc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaactt tccgcatggt    960

ttcaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaacgg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttagc gaagtggcg                          1359
```

<210> SEQ ID NO 154
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 154

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Gly Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Val Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240
```

```
Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Thr Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 155
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 155

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttgg tagcggccgt gtgtttctga ccaacagcgg cagcgaagcg    360

aacgatacca tggtgaaaat gctgtggttt ctgcatgcgg cggaaggcaa accgcaaaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattaccc cggcgaaagg ctattttcag    720

gcgattctgc cgatcctgcg caaatatgat attccggtga tcagcgatga agtgatttgc    780
```

```
ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaattt tccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 156
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 156

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Gly Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
```

```
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 157
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 157

atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caatatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttgg tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgtgt taacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaattt tccgcatggt    960
```

```
tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 158
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 158

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Gly Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Val Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285
```

-continued

```
Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 159
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 159

atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcaaaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattgttc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaactt tccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080
```

```
aaacatattg cggaacgtcc gaacattggc gaatatcgtg gcattggctt tatgtgggcg   1140

ctggaaatcg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttagc gaagtggcg                          1359


<210> SEQ ID NO 160
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 160

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320
```

```
Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 161
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 161

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgtgt taacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaatgcct aaccgcgggt ttttttccgg taggcgcggt gattctgggt    900

ccggaactga gcaaacgtct ggaaaccgcg attgaagcga tcggcaactt tccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaatcg tgaaagataa agcgagcaaa gccccgtttg atggcaacct gagcgtgagc   1200

gaacgtattg cgaacacctg caccgatctg ggcctgatta tccgtccgac aggccagagc   1260
```

gtggttctgt gcccgccgtt tattctgacc gaagcgcaga tggatgaaat gttcgataaa 1320
ctggaaaaag cgctggataa agtgtttagc gaagtggcg 1359

<210> SEQ ID NO 162
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 162

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Phe Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Val Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Cys Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Asn Phe Pro His Gly
305 310 315 320

Phe Thr Thr Gly Gly His Pro Val Gly Cys Ala Ile Ala Leu Lys Ala
325 330 335

Ile Asp Val Val Met Asn Glu Gly Leu Ala Glu Asn Val Arg Arg Leu 340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Ile Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450

<210> SEQ ID NO 163
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 163
atgaacaaac cgcagagctg ggaaacgcgt gcggaaacct atagcctgta tggttttacc 60
gatatgccga gcctgcatca gcgtggcacc atggtggtgg cccatggcga aggcccgtat 120
atcgtggatg tgcatggccg tcgttatctg gatgcgaaca gcggcgcttt caacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcaaaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattaccc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaatgcct aaccgcgggt ttttttccgg taggcgcggt gattctgggt 900
ccggaactga gcaaacgtct ggaaaccgcg attgaagcga tcggcaactt tccgcatggt 960
tttaccacgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaaatcg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttagc gaagtggcg 1359

<210> SEQ ID NO 164
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 164

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Phe Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Ser Gly His Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Arg Trp Asn Ala Tyr His Gly Cys Thr Val Val Ser Ala Ser Met
145 150 155 160

Thr Gly Phe Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Cys Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Asn Phe Pro His Gly
305 310 315 320

Phe Thr Thr Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

-continued

```
Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450


<210> SEQ ID NO 165
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 165

atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgtgt taacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattgtcc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaactt tccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaacgg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttagc gaagtggcg                          1359


<210> SEQ ID NO 166
<211> LENGTH: 453
<212> TYPE: PRT
<213> ORGANISM: Artificial Sequence
```

<220> FEATURE:
<223> OTHER INFORMATION: Engineered variant of V. fluvialis transaminase

<400> SEQUENCE: 166

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Val Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Thr Val
    370                 375                 380

Lys Asp Lys Ala Ser Lys Ala Pro Phe Asp Gly Asn Leu Ser Val Ser
385                 390                 395                 400
```

```
Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 167
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 167

```
atgaacaaac cgcagagctg ggaaacgcgt gcggaaacct atagcctgta tggttttacc     60
gatatgccga gcctgcatca gcgtggcacc atggtggtgg cccatggcga aggcccgtat    120
atcgtggatg tgcatggccg tcgttatctg gatgcgaaca gcggcgcttt caacatggtg    180
gcgggctttg atcataaagg cctgattgat gcggcgaaag cgcagtatga acgttttccg    240
ggctatcatg cgttttcagg ccatatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggctgta ccgtagtgag cgcgagcatg    480
accggctttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgctggcggt gttattccgc cggcgaaagg ctattttcag    720
gcgattctgc cgatcctgcg caaatatgat attccggtga tcagcgatga agtgatttgc    780
ggctttggcc gtaccggtaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcggcaattt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaaatcg tgaaagataa agcgagcaaa gccccgtttg atggcaacct gagcgtgagc   1200
gaacgtattg cgaacacctg caccgatctg ggcctgattt gccatccgac aggccagagc   1260
gtggttctgt gcccgccgtt tattctgacc gaagcgcaga tggatgaaat gttcgataaa   1320
ctggaaaaag cgctggataa agtgtttgcg gaagtggcg                           1359
```

<210> SEQ ID NO 168
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 168

-continued

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
```

-continued 420 425 430

Gln Met Asp Glu Met Phe Asp Lys Leu Glu Lys Ala Leu Asp Lys Val
435 440 445

Phe Ala Glu Val Ala
450

<210> SEQ ID NO 169
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 169
atgaacaaac cgcagagctg ggaaacgcgt gcggaaacct atagcctgta tggttttacc 60
gatatgccga gcctgcatca gcgtggcacc atggtggtgg cccatggcga aggcccgtat 120
atcgtggatg tgcatggccg tcgttatctg gatgcgaaca gcggcgcttt caacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaatgcct aaccgcgggt ttttttccgg taggcgcggt gattctgggt 900
ccggaactga gcaaacgtct ggaaaccgcg attgaagcga tcggcagctt tccgcatggt 960
tttaccacgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaaatcg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 170
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 170

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

```
Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Cys Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Ser Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445
```

Phe Ala Glu Val Ala
450

<210> SEQ ID NO 171
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 171
atgaacaaac cgcagagctg ggaaacgcgt gcggaaacct atagcctgta tggttttacc 60
gatatgccga gcctgcatca gcgtggcacc atggtggtgg cccatggcga aggcccgtat 120
atcgtggatg tgcatggccg tcgttatctg gatgcgaaca gcggcgcttt caacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcaaaaa 420
cgtaaaattc tgacccgttg gaacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattgtcc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attgaagcga tcggcagctt tccgcatggt 960
tttaccacgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gcattggctt tatgtgggcg 1140
ctggaagtcg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgt gcccgccgtt tattctgacc gaagcgcaga tggatgaaat gttcgataaa 1320
ctggaaaaag cgctggataa agtgtttgcg gaagtggcg 1359

<210> SEQ ID NO 172
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 172

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Asn Ser Gly Ala Phe Asn Met Val Ala Gly Phe Asp

-continued

```
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Ser Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 173

<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 173

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttgta ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattgtcc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac ccccggatgcg   840

attattagca gtaaaaacct aaccgcgggt ttttttccgg taggcgcggt gattctgggt    900

ccggaactga gcaaacgtct ggaaaccgcg attgaagcga tcggcaactt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaatcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttagc gaagtggcg                           1359
```

<210> SEQ ID NO 174
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 174

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80
```

```
Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Cys Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 175
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 175

```
atgaacaaac cgcagagctg ggaaacgcgt gcggaaacct atagcctgta tggttttacc     60
gatatgccga gcctgcatca gcgtggcacc gtggtggtgg cccatggcga aggcccgtat    120
atcgtggatg tgcatggccg tcgttatctg gatgcgaaca gcggcgcttt caacatggtg    180
gcgggctttg atcataaagg cctgattgat gcggcgaaag cgcagtatga acgttttccg    240
ggctatcatg cgttttcagg ccatatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcaaaaa    420
cgtaaaattc tgacccgtca caacgcgtat catggctgta ccgtagtgag cgcgagcatg    480
accggctttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgctggcggt gttattccgc cggcgaaagg ctattttcag    720
gcgattctgc cgatcctgcg caaatatgat attccggtga tcagcgatga agtgatttgc    780
ggctttggcc gtaccggtaa cacctggggc tgcgtgacct atgattttac cccggatgcg    840
attattagca gtaaatgcct aaccgcgggt ttttttccgg taggcgcggt gattctgggt    900
ccggaactga gcaaacgtct ggaaaccgcg attgaagcga tcggcagctt tccgcatggt    960
tttaccacgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccatccgac aggccagagc   1260
gtggttctgt gcccgccgtt tattctgacc gaagcgcaga tggatgaaat gttcgataaa   1320
ctggaaaaag cgctggataa agtgtttgcg gaagtggcg                          1359
```

<210> SEQ ID NO 176
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 176

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110
```

```
Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg His Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Cys Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Ser Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 177
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 177

```
atgaacaaac cgcagagctg ggaaacgcgt gcggaaacct atagcctgta tggttttacc     60
```

```
gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaatgcct aaccgcgggt ttttttccgg taggcgcggt gattctgggt    900

ccggaactga gcaaacgtct ggaaaccgcg attgaagcga tcggcaactt tccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttagc gaagtggcg                           1359
```

<210> SEQ ID NO 178
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 178

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
```

```
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Cys Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 179
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 179

```
atgaacaaac cgcagagctg ggaaacgcgt gcggaaacct atagcctgta tggttttacc      60

gatatgccga gcctgcatca gcgtggcacc atggtggtgg cccatggcga aggcccgtat     120

atcgtggatg tgcatggccg tcgttatctg gatgcgaaca gcggcgcttt caacatggtg     180

gcgggctttg atcataaagg cctgattgat gcggcgaaag cgcagtatga acgttttccg     240
```

```
ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgtca caacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaattt tccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaatcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttagc gaagtggcg                          1359
```

```
<210> SEQ ID NO 180
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 180

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg His Asn Ala Tyr His Gly Cys Thr Val Val Ser Ala Ser Met
145                 150                 155                 160
```

-continued

```
Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 181
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 181

```
atgaacaaac cgcagagctg ggaaacgcgt gcggaaacct atagcctgta tggttttacc      60

gatatgccga gcctgcatca gcgtggcacc atggtggtgg cccatggcga aggcccgtat     120

atcgtggatg tgcatggccg tcgttatctg gatgcgaaca gcggcgcttt caacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttata ccaacagcgg cagcgaagcg     360
```

```
aacgatacca tggtgaaaat gctgtggttt ctgcatgcgg cggaaggcaa accgcagaaa    420

cgtaaaattc tgacccgtca caacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattgtcc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcagctt tccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaatcg tgaaagataa agcgagcaaa gccccgtttg atggcaacct gagcgtgagc   1200

gaacgtattg cgaacacctg caccgatctg ggctgattt gccgtccgac aggccagagc   1260

gtggttctgt gcccgccgtt tattctgacc gaagcgcaga tggatgaaat gttcgataaa   1320

ctggaaaaag cgctggataa agtgtttagc gaagtggcg                          1359
```

```
<210> SEQ ID NO 182
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 182

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg His Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190
```

-continued

```
Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Ser Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 183
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 183

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcaaaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540
```

```
tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattgtcc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaatgcct aaccgcgggt tttttccgg taggcgcggt gattctgggt     900

ccggaactga gcaaacgtct ggaaaccgcg attgaagcga tcggcaactt tccgaatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaacgg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

<210> SEQ ID NO 184
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 184

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
```

```
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Cys Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro Asn Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Thr Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 185
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 185

```
atgaacaaac cgcagagctg ggaaacgcgt gcggaaacct atagcctgta tggttttacc      60

gatatgccga gcctgcatca gcgtggcacc atggtggtgg cccatggcga aggcccgtat     120

atcgtggatg tgcatggccg tcgttatctg gatgcgaaca gcggcgcttt caacatggtg     180

gcgggctttg atcataaagg cctgattgat gcggcgaaag cgcagtatga acgttttccg     240

ggctatcatg cgttttcagg ccatatgagc gatcagaccg tgatgctgtc tgaaaaactg     300

gtggaagtga gcccgtttga tagcggccgt gtgttttgta ccaacagcgg cagcgaagcg     360

aacgatacca tggtgaaaat gctgtggttt ctgcatgcgg cggaaggcaa accgcaaaaa     420

cgtaaaattc tgacccgttg gaacgcgtat catggctgta ccgtagtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660
```

```
tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaattt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                           1359


<210> SEQ ID NO 186
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 186

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Cys Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240
```

```
Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
            405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 187
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 187

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcaaaaa    420

cgtaaaattc tgacccgtca caacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840
```

```
attattagca gtaaaaacct aaccgcgggt ttttttccgg taggcgcggt gattctgggt    900

ccggaactga gcaaacgtct ggaaaccgcg attgaagcga tcggcaattt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaatcg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359
```

```
<210> SEQ ID NO 188
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 188

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg His Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ile Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 189
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 189
atgaacaaac cgcagagctg ggaaacgcgt gcggaaacct atagcctgta tggttttacc 60
gatatgccga gcctgcatca gcgtggcacc atggtggtgg cccatggcga aggcccgtat 120
atcgtggatg tgcatggccg tcgttatctg gatgcgaaca gcggcgcttt caacatggtg 180
gcgggctttg atcataaagg cctgattgat gcggcgaaag cgcagtatga acgttttccg 240
ggctatcatg cgttttcagg ccatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgacccgtgt taacgcgtat catggctgta ccgtagtgag cgcgagcatg 480
accggctttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattgtcc cggcgaaagg ctattttcag 720
gcgattctgc cgatcctgcg caaatatgat attccggtga tcagcgatga agtgatttgc 780
ggctttggcc gtaccggtaa cacctggggc tgcgtgacct atgattttac cccggatgcg 840
attattagca gtaaatgcct aaccgcgggt ttttttccgg taggcgcggt gattctgggt 900
ccggaactga gcaaacgtct ggaaaccgcg attgaagcga tcggcaactt tccgcatggt 960

-continued

```
tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaaatgg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgt gcccgccgtt tattctgacc gaagcgcaga tggatgaaat gttcgataaa   1320

ctggaaaaag cgctggataa agtgtttagc gaagtggcg                          1359
```

<210> SEQ ID NO 190
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 190

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Val Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Cys Leu Thr
        275                 280                 285

Ala Gly Phe Phe Pro Val Gly Ala Val Ile Leu Gly Pro Glu Leu Ser
```

```
    290                 295                 300

Lys Arg Leu Glu Thr Ala Ile Glu Ala Ile Gly Asn Phe Pro His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Met Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ser Glu Val Ala
    450
```

<210> SEQ ID NO 191
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 191

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgaaca gcggcgcttt caacatggtg    180

gcgggctttg atcataaagg cctgattgat gcggcgaaag cgcagtatga acgttttccg    240

ggctatcatg cgttttcagg ccatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgacccgttg gaacgcgtat catggctgta ccgtagtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattgtcc cggcgaaagg ctattttcag    720

gcgattctgc cgatcctgcg caaatatgat attccggtga tcagcgatga agtgatttgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcaactt gccgcatggt    960

tttaccacgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140
```

```
ctggaagtcg tgaaagataa agcgagcaaa gccccgtttg atggcaacct gagcgtgagc   1200

gaacgtattg cgaacacctg caccgatctg ggcctgattt gccatccgac aggccagagc   1260

gtggttctgt gcccgccgtt tattctgacc gaagcgcaga tggatgaaat gttcgataaa   1320

ctggaaaaag cgctggataa agtgtttgcg gaagtggcg                          1359


<210> SEQ ID NO 192
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 192

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Asn Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly His Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Val Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Val Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Asn Leu Pro His Gly
305                 310                 315                 320
```

```
Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys His Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 193
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 193

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgatga gcggcgcttt caacatggtg    180

gcgggctttg atcataaagg cctgattgat gcggcgaaag cgcagtatga acgttttccg    240

ggctatcatg cgttttgcgg ctatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgaccctgtg gaacgcgtat catggctgca ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattccac cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gccgtccgac aggccagagc   1260
```

gtggttctgg ctccgccgtt cattctgacc gaagcgcaga tggatgaaat gttcgataaa 1320
ctggaaaaag cgctggataa agtgtttgcg gaagtggcg 1359

<210> SEQ ID NO 194
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 194

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Met Ser Gly Ala Phe Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Cys Gly Tyr Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Leu Trp Asn Ala Tyr His Gly Cys Thr Val Val Ser Ala Ser Met
145 150 155 160

Thr Gly Phe Pro Phe Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Val Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

```
Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 195
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 195

atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgatga gcggcgcttt caacatggtg    180

gcgggctttg atcataaagg cctgattgat gcggcgaaag cgcagtatga acgttttccg    240

ggctatcatg cgttttgcgg ctatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgaccctgtg gaacgcgtat catggcgtga ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attaatgcga acggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgg ctccgccgtt cattctgacc gaagcgcaga tggatgaaat gttcgataaa   1320

ctggaaaaag cgctggataa agtgtttgcg gaagtggcg                           1359
```

<210> SEQ ID NO 196
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 196

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Ala His Gly Glu Gly Pro Tyr Ile Val Asp Val His Gly Arg Arg
        35                  40                  45

Tyr Leu Asp Ala Met Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Val Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Asn Ala Asn Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
```

```
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 197
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 197

```
atgaacaaac cgcagagctg ggaaacgcgt gcggaaacct atagcctgta tggttttacc     60

gatatgccga gcctgcatca gcgtggcacc gtggtggtgg cccatggcga aggcccgtat    120

atcgtggatg tgcatggccg tcgttatctg gatgcgatga gcggcgcttt caacatggtg    180

gcgggctttg atcataaagg cctgattgat gcggcgaaag cgcagtatga acgttttccg    240

ggctatcatg cgttttgcgg ctatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcagaaa    420

cgtaaaattc tgaccctgtg gaacgcgtat catggctgca ccgtagtgag cgcgagcatg    480

accggctttc cgttcaacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgg ctccgccgtt cattctgacc gaagcgcaga tggatgaaat gttcgataaa   1320

ctggaaaaag cgctggataa agtgtttgcg gaagtggcg                           1359
```

<210> SEQ ID NO 198
<211> LENGTH: 453
<212> TYPE: PRT
<213> ORGANISM: Artificial Sequence
<220> FEATURE:

<223> OTHER INFORMATION: Engineered variant of V. fluvialis transaminase

<400> SEQUENCE: 198

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Val Val
20 25 30

Val Ala His Gly Glu Gly Pro Tyr Ile Val Asp Val His Gly Arg Arg
35 40 45

Tyr Leu Asp Ala Met Ser Gly Ala Phe Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Cys Gly Tyr Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Ala Ala Glu Gly Lys Pro Gln Lys Arg Lys Ile Leu
130 135 140

Thr Leu Trp Asn Ala Tyr His Gly Cys Thr Val Val Ser Ala Ser Met
145 150 155 160

Thr Gly Phe Pro Phe Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Pro Pro Ala Lys Gly Tyr Phe Gln
225 230 235 240

Ala Ile Leu Pro Ile Leu Arg Lys Tyr Asp Ile Pro Val Ile Ser Asp
245 250 255

Glu Val Val Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Pro His Gly
305 310 315 320

Phe Thr Ala Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu His Pro Asn
355 360 365

Ile Gly Glu Tyr Arg Gly Ile Gly Phe Met Trp Ala Leu Glu Val Val
370 375 380

Lys Asp Lys Ala Ser Lys Ala Pro Phe Asp Gly Asn Leu Ser Val Ser
385 390 395 400

-continued

```
Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 199
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 199

```
atgaacaaac cgcagagctg ggaaacgcgt gcggaaacct atagcctgta tggttttacc     60

gatatgccga gcctgcatca gcgtggcacc atggtggtgg cccatggcga aggcccgtat    120

atcgtggatg tgcatggccg tcgttatctg gatgcgatga gcggcgcttt caacatggtg    180

gcgggctttg atcataaagg cctgattgat gcggcgaaag cgcagtatga acgttttccg    240

ggctatcatg cgttttgcgg ctatatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatgcgg cggaaggcaa accgcaaaaa    420

cgtaaaattc tgaccctgtg gaacgcgtat catggcgtga ccgtagtgag cgcgagcatg    480

accggctttc cgttcaacag cgtgtttggc cagccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgctggcggt gttattccgc cggcgaaagg ctattttcag    720

gcgattctgc cgatcctgcg caaatatgat attccggtga tcagcgatga agtggtgtgc    780

ggctttggcc gtaccggtaa cacctggggc tgcgtgacct atgattttac cccggatgcg    840

attattagca gtaaaaacct aaccgcgggt ttttttccgg taggcgcggt gattctgggt    900

ccggaactga gcaaacgtct ggaaaccgcg attgaagcga tcggcgaatt tccgcatggt    960

tttaccgcgg gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacatcc gaacattggc gaatatcgtg gcattggctt tatgtgggcg   1140

ctggaagttg tgaaagataa agcgagcaaa gccccgtttg atggcaacct gagcgtgagc   1200

gaacgtattg cgaacacctg caccgatctg ggcctgattt gccgtccgac aggccagagc   1260

gtggttctgg ctccgcggtt cattctgacc gaagcgcaga tggatgaaat gttcgataaa   1320

ctggaaaaag cgctggataa agtgtttgcg gaagtggcg                          1359
```

<210> SEQ ID NO 200
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 200

```
Met Asn Lys Pro Gln Ser Trp Glu Thr Arg Ala Glu Thr Tyr Ser Leu
```

-continued

```
1               5                   10                  15

Tyr Gly Phe Thr Asp Met Pro Ser Leu His Gln Arg Gly Thr Met Val
            20                  25                  30

Val Ala His Gly Glu Gly Pro Tyr Ile Val Asp Val His Gly Arg Arg
        35                  40                  45

Tyr Leu Asp Ala Met Ser Gly Ala Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Val Thr Val Val Ser Ala Ser Met
145                 150                 155                 160

Thr Gly Phe Pro Phe Asn Ser Val Phe Gly Gln Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Arg Phe Ile Leu Thr Glu Ala
            420                 425                 430
```

Gln Met Asp Glu Met Phe Asp Lys Leu Glu Lys Ala Leu Asp Lys Val
        435                 440                 445

Phe Ala Glu Val Ala
    450

<210> SEQ ID NO 201
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 201
atgaacaaac cgcagagctg ggaaacgcgt gcggaaacct atagcctgta tggttttacc 60
gatatgccga gcctgcatca gcgtggcacc gtggtggtgg cccatggcga aggcccgtat 120
atcgtggatg tgcatggccg tcgttatctg gatgcgatga gcggcgcttt gaacatggtg 180
gcgggctttg atcataaagg cctgattgat gcggcgaaag cgcagtatga acgttttccg 240
ggctatcatg cgttttgcgg ctatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgaccctgtg gaacgcgtat catggctgca ccgtagtgag cgcgagcatg 480
accggctttc cgttcaacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtggtgtgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attaatgcga tcggcggatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacatcc gaacattggc gaatatcgtg gcattggctt tatgtgggcg 1140
ctggaagttg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgg ctccgccgtt cattctgacc gaagcgcaga tggatgaaat gttcgataaa 1320
ctggaaaaag cgctggataa agtgtttgcg gaagtggcg 1359

<210> SEQ ID NO 202
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 202

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

```
Val Ala His Gly Glu Gly Pro Tyr Ile Val Asp Val His Gly Arg Arg
        35                  40                  45

Tyr Leu Asp Ala Met Ser Gly Ala Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Asn Ala Ile Gly Gly Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
```

450

<210> SEQ ID NO 203
<211> LENGTH: 1359
<212> TYPE: DNA
<213> ORGANISM: Artificial Sequence
<220> FEATURE:
<223> OTHER INFORMATION: Engineered variant of V. fluvialis transaminase

<400> SEQUENCE: 203
atgaacaaac cgcagagctg ggaaacgcgt gcggaaacct atagcctgta tggttttacc 60
gatatgccga gcctgcatca gcgtggcact atggtggtgg cccatggcga aggcccgtat 120
atcgtggatg tgcatggccg tcgttatctg gatgcgatga gcggcgcttt caacatggtg 180
gcgggctttg atcataaagg cctgattgat gcggcgaaag cgcagtatga acgttttccg 240
ggctatcatg cgttttgcgg ctatatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatgcgg cggaaggcaa accgcagaaa 420
cgtaaaattc tgaccctgtg gaacgcgtat catggctgca ccgtagtgag cgcgagcatg 480
accggctttc cgttcaacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgctggcggt gttattccgc cggcgaaagg ctattttcag 720
gcgattctgc cgatcctgcg caaatatgat attccggtga tcagcgatga agtggtgtgc 780
ggctttggcc gtaccggtaa cacctggggc tgcgtgacct atgattttac cccggatgcg 840
attattagca gtaaaaacct aaccgcgggt ttttttccgg taggcgcggt gattctgggt 900
ccggaactga gcaaacgtct ggaaaccgcg attaatgcga tcggcgaatt tccgcatggt 960
tttaccgcgg gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacatcc gaacattggc gaatatcgtg gcattggctt tatgtgggcg 1140
ctggaagttg tgaaagataa agcgagcaaa gccccgtttg atggcaacct gagcgtgagc 1200
gaacgtattg cgaacacctg caccgatctg ggcctgattt gccgtccgac aggccagagc 1260
gtggttctgg ctccgccgtt cattctgacc gaagcgcaga tggatgaaat gttcgataaa 1320
ctggaaaaag cgctggataa agtgtttgcg gaagtggcg 1359

<210> SEQ ID NO 204
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 204

Met Asn Lys Pro Gln Ser Trp Glu Thr Arg Ala Glu Thr Tyr Ser Leu
1 5 10 15

Tyr Gly Phe Thr Asp Met Pro Ser Leu His Gln Arg Gly Thr Met Val
20 25 30

Val Ala His Gly Glu Gly Pro Tyr Ile Val Asp Val His Gly Arg Arg
35 40 45

Tyr Leu Asp Ala Met Ser Gly Ala Phe Asn Met Val Ala Gly Phe Asp
50 55 60

```
His Lys Gly Leu Ile Asp Ala Ala Lys Ala Gln Tyr Glu Arg Phe Pro
65                  70                  75                  80

Gly Tyr His Ala Phe Cys Gly Tyr Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Leu Trp Asn Ala Tyr His Gly Cys Thr Val Val Ser Ala Ser Met
145                 150                 155                 160

Thr Gly Phe Pro Phe Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Val Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Asn Ala Ile Gly Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu His Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Ala Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

ENGINEERED BIOCATALYSTS AND METHODS FOR SYNTHESIZING CHIRAL AMINES

CROSS REFERENCE TO RELATED APPLICATIONS

The present application is a national stage application filed under 35 USC § 371 and claims priority to international application to PCT International Application No. PCT/US2013/075294, filed Dec. 16, 2013, and U.S. Prov. Appln. Ser. No. 61/745,219, filed on Dec. 21, 2012. The present application hereby incorporates both of these priority applications by reference, in their entireties and for all purposes.

The present application claims priority to US Provisional Appln. Ser. No. 61/745,219, filed Dec. 21, 2012, which is incorporated for all purposes in its entirety.

1. TECHNICAL FIELD

The disclosure relates to transaminase biocatalysts and processes using the biocatalysts for the preparation of chiral amines.

2. REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-126USP1_ST25.txt", a creation date of Dec. 21, 2012, and a size of 606,099 kilobytes. The Sequence Listing filed via EFS-Web is part of the specification and is incorporated in its entirety by reference herein.

3. BACKGROUND

Transaminases (E.C. 2.6.1) catalyze the transfer of an amino group, a pair of electrons, and a proton from a primary amine of an amino donor substrate to the carbonyl group of an amino acceptor molecule as shown in Scheme 1.

Scheme 1

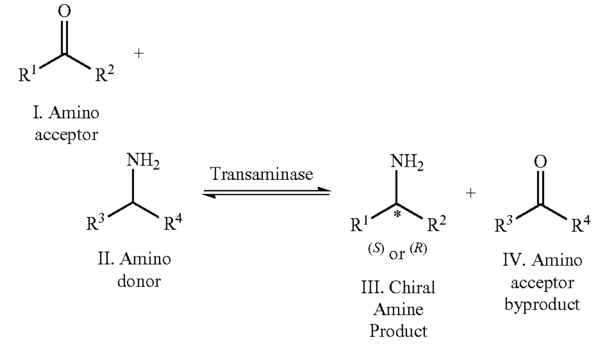

I. Amino acceptor

II. Amino donor

III. Chiral Amine Product

IV. Amino acceptor byproduct

An amino acceptor compound (I) (which is the precursor of the desired chiral amine product (III)) is reacted with an amino donor compound (II). The transaminase catalyzes the transfer of the amine group of the amino donor (II) to the keto group of the amino acceptor (I). The reaction results in the desired chiral amine product compound (III) and a new amino acceptor compound (IV) with a ketone group as a by-product.

Wild-type transaminases having the ability to catalyze a reaction of Scheme 1 have been isolated from various microorganisms, including, but not limited to, *Alcaligenes denitrificans, Bordetella bronchiseptica. Bordetella parapertussis, Brucella melitensis, Burkholderia malle, Burkholderia pseudomallei, Chromobacterium violaceum, Oceanicola granulosus* HTCC2516, *Oceanobacter* sp. RED65. *Oceanospirillum* sp. MED92, *Pseudomonas putida, Ralstonia solanacearum, Rhizobium meliloti, Rhizohium* sp. (strain NGR234), *Bacillus thuringensis, Klebsiella pneumonia*, and *Vibrio fluvialis* (see e.g., Shin et al., 2001. Biosci. Biotechnol, Biochem. 65:1782-1788). Several of these wild-type transaminase genes and encoded polypeptides have been sequenced, including e.g., *Ralsionia solanacearum* (Genbank Acc. No. YP_002257813.1, GI:207739420), *Burkholderia pseudomallei* 1710b (Genbank Acc. No. ABA47738.1. GI:76578263), *Bordetella petrii* (Genbank Acc. No. AM902716.1, GI:163258032), and *Vibrio fluvialis* (Genbank Acc. No. AEA39183.1, GI: 327207066). Two wild-type transaminases of classes EC 2.6.1.18 and EC 2.6.1-19, have been crystallized and structurally characterized (see e.g., Yonaha et al., 1983, Agric. Biol. Chem. 47 (10):2257-2265).

The wild-type transaminase from *Vibrio fluvialis* JS17 is an ω-amino acid:pyruvate transaminase (E.C. 2.6.1.18) that uses pyridoxal-5'-phosphate as cofactor to catalyze the reaction of Scheme 2.

Scheme 2

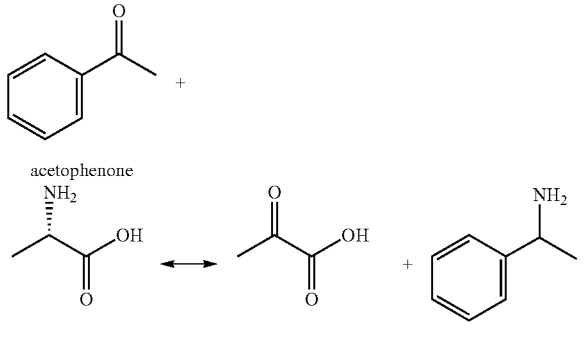

acetophenone

L-alanine pyruvic acid 1-phenylethylamine

This wild-type transaminase from *Vibrio fluvialis* also has been reported to show catalytic activity toward aliphatic amino donors that do not have a carboxyl group.

Chiral amine compounds are frequently used in the pharmaceutical, agrochemical and chemical industries as intermediates or synthons for the preparation of various pharmaceuticals, such as cephalosporine or pyrrolidine derivatives. A great number of these industrial applications of chiral amine compounds involve using only one particular optically active form, e.g., only the (R) or the (S) enantiomer is physiologically active. Transaminases have potential industrial use for the stereoselective synthesis of optically pure chiral amine compounds, such as in the enantiomeric enrichment of amino acids (see e.g., Shin et al., 2001. Biosci. Biotechnol. Biochem. 65:1782-1788; Iwasaki et al., 2003, Biotech. Lett. 25:1843-1846; Iwasaki et al., 2004, Appl. Microb. Biotech. 69:499-505, Yun et al., 2004, Appl. Environ. Microbiol. 70:2529-2534; and Hwang et al., 2004, Enzyme Microbiol. Technol. 34:429-426).

Other examples of the use of transaminases include the preparation of intermediates and precursors of pregabalin (e.g., WO 2008/127646): the enzymatic transamination of cyclopamine analogs (e.g., WO 2011/017551); the stereospecific synthesis and enantiomeric enrichment of β-amino acids (e.g., WO 2005/005633); the enantiomeric enrichment of amines (e.g., U.S. Pat. No. 4,950,606; U.S. Pat. No. 5,300,437; and U.S. Pat. No. 5,169,780); and the production of amino acids and derivatives (e.g., U.S. Pat. No. 5,316,943; U.S. Pat. No. 4,518,692; U.S. Pat. No. 4,826,766; U.S. Pat. No. 6,197,558; and U.S. Pat. No. 4,600,692).

However, transaminases used to catalyze reactions for the preparation of chiral amine compounds can have properties that are undesirable for commercial applications, such as instability to industrially useful process conditions (e.g., solvent, temperature) and narrow substrate recognition. Thus, there is a need for other types of transaminase biocatalysts that can be used in industrial processes for preparing chiral amines compounds in an optically active form.

4. SUMMARY

The present disclosure provides engineered polypeptides having transaminase activity, polynucleotides encoding the polypeptides, methods of the making the polypeptides, and methods of using the polypeptides for the biocatalytic conversion of ketone substrates to amine products. The polypeptides having transaminase activity of the present disclosure have been engineered to have one or more residue differences as compared to a previously engineered transaminase polypeptide (of amino acid sequence SEQ ID NO: 2) with enhanced solvent and thermal stability relative to the wild-type transaminase of *Vibrio fluvialis*. The amino residue differences are located at residue positions affecting various enzyme properties, including among others, activity, stereoselectivity, stability, expression, and product tolerance. In particular, the engineered transaminase polypeptides of the present disclosure have been engineered for efficient conversion of an exemplary large cyclopamine analog ketone compound of compound (2) to its corresponding chiral amine product compound of compound (1) as shown in Scheme 3.

Scheme 3

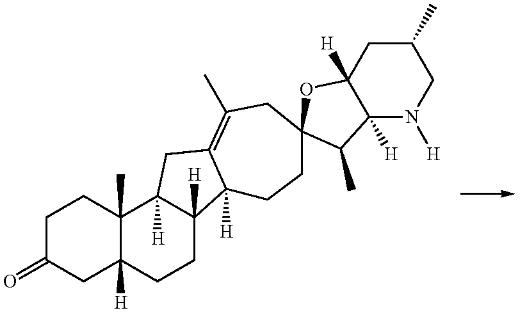

(2)

-continued

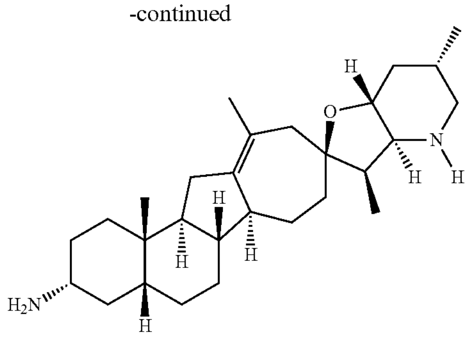

(1)

The evolved structural features of the engineered transaminase polypeptides of the present disclosure also allow for the conversion of a range of large ketone substrate compounds (other than the compound (2)), such as cyclopamine analogs, veratramine analogs, and steroid analogs, of Formula (II) to their corresponding chiral amine product compounds of Formula (I) as shown in Scheme 4.

Scheme 4

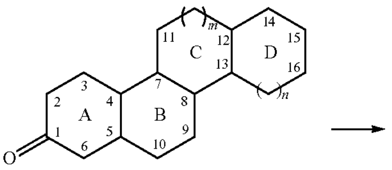

(II)

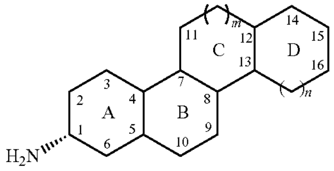

(I)

wherein rings A-D of the compounds can be substituted as follows:

Ring A is a 6-membered carbocyclic ring, optionally including an unsaturated C—C bond between positions 2 and 3 and/or positions 5 and 6, and/or optionally substituted independently positions 2, 3, 4, 5 and 6 with a group selected from halo, hydroxy, and methyl;

Ring B is a 6-membered carbocyclic ring, optionally including an unsaturated C—C bond between positions 5 and 10, and/or optionally substituted independently at one or more of positions 9 and 10 with a group selected from halo, hydroxy, and methyl;

Ring C is a 5- or 6-membered carbocyclic ring (i.e., m=0 or 1), optionally substituted at position 10 with a group selected from halo, hydroxy, methyl, ethyl, and carbonyl;

Ring D is a 5-, 6-, or 7-membered carbocyclic ring (i.e., n=0, 1, or 2), optionally including 1, 2, or 3 unsaturated C—C bonds, and/or optionally substituted independently as follows:

at position 14 with a group selected from halo, hydroxy, amino, carboxy, cyano, nitro, thio, straight-chain or branched $(C_1-C_4)$alkyl, straight-chain or branched $(C_1-C_4)$alkenyl, straight-chain or branched $(C_1-C_3)$alkylamino, and cyclopropyl bridging to position 12;

at position 15 or position 16 with a group selected from halo, hydroxy, amino, carboxy, cyano, nitro, thio, optionally substituted ($C_1$-$C_6$)alkyl, hydroxy($C_1$-$C_6$)alkyl, optionally substituted ($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted arylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$)alkyl.

Thus, the engineered polypeptides disclosed herein display, among others, increased activity, high stereoselectivity, increased solvent and thermal stability, and increased product tolerance in the conversion of large prochiral ketone substrate compounds of Formula (II) to the corresponding chiral amine product compounds of Formula (I).

Accordingly, in one aspect, the present disclosure provides engineered polypeptides having transaminase activity, where the engineered polypeptide comprises an amino acid sequence having at least 80% identity to SEQ ID NO: 2 and one or more residue differences as compared to SEQ ID NO:2 at residue positions selected from X19, X21, X34, X53, X56, X73, X86, X88, X107, X113, X147, X155, X165, X171, X178, X233, X251, X259, X268, X277, X286, X312, X316, X317, X358, X366, X383, X399, X414, X415, X417, X426, X434, and X450, wherein the residue differences at residue positions X21, X56, X86, X88, X107, X113, X133, X147, X233, X286, X312, X316, X383, X415, X417, and X434, are selected from: X21H, X56A/C, X86C, X88H/Y, X107G, X113L/P, X147H/V, X233V, X286C/H, X312N, X316C/F/G/N/S/T, X383C/F/I/M/T, X415A/G/H/UV, X417V, and X434T. In some embodiments, the residue differences at the residue positions X19, X34, X53, X73, X155, X165, X171, X178, X251, X259, X268, X277, X317, X358, X366, X399, X414, X426, and X450 are selected from X19W, X34A, X53M, X73R, X155V, X165F, X171Q, X178W, X251V, X259V, X268A, X277A, X317L, X358K, X366H, X399A, X414I, X426R, and X450S.

In some embodiments of the engineered polypeptides having transaminase activity, the amino acid sequence comprises at least one or more residue differences as compared to SEQ ID NO: 2 selected from: X34A, X56A, X88H, X107G, X113L, X147H, X153C, X155V, X233V, X315G, X316N, X383I, and X450S. In some embodiments, the amino acid sequence further comprises one or more residue differences selected from: X31M, X57F/L, X86N/S. X153A, X233T, X323T, X383V, and X417T.

In some embodiments of the engineered polypeptides having transaminase activity, the amino acid sequence comprises at least a combination of residue differences as compared to SEQ ID NO: 2 comprising X34A, X56A, X57L, X86S, X88A; X153C, X155V, X163F, X315G, and X417T. In some embodiments, the amino acid sequence further comprises the residue difference X316N. In some embodiments, the amino acid sequence further comprises the residue difference X316N and one or more residue differences selected from X31M, X57F, X323T, X383I/T, X415H, and X450S.

In some embodiments of the engineered polypeptides having transaminase activity, the amino acid sequence comprises the residue differences as compared to SEQ ID NO: 2 X34A, X56A, X57L, X86S, X88A; X153C, X155V, X163F, X315G, X316N, and X417T and further comprises a combination of residue differences selected from: (a) X31M, X57F, X323T, and X383V; (b) X31M, X57F, X107G, X113L, X233T, X415H, and X450S; (c) X31M, X57F, X233V, X323T, X383I, X415H, and X450S; and (d) X31M, X57F, X147H, X323T, X383I, X415H, and X450S.

In some embodiments of the engineered polypeptides having transaminase activity, the engineered polypeptide has at least 1.2 fold increased stability as compared to the polypeptide of SEQ ID NO: 4, wherein the amino acid sequence comprises one or more residue differences as compared to SEQ ID NO: 2 selected from: X34T, X107G, X113L, X147H, X155V, X233T/V, X323T, X383I/V, and X450S.

In some embodiments of the engineered polypeptides having transaminase activity, the engineered polypeptide has at least 1.2 fold increased activity as compared to the polypeptide of SEQ ID NO: 4 in converting compound (2) to compound (1), wherein the amino acid sequence comprises one or more residue differences as compared to SEQ ID NO: 2 selected from: X56A, X86S, X88H, X153C. X415H, and X417T.

In some embodiments of the engineered polypeptides having transaminase activity, the engineered polypeptide has increased enantioselectivity as compared to the polypeptide of SEQ ID NO: 4 in converting compound (2) to compound (1), wherein the amino acid sequence comprises one or more residue differences as compared to SEQ ID NO: 2 selected from: X57F, X153C, and X316N.

In some embodiments of the engineered polypeptides having transaminase activity, the amino acid sequence further comprises a residue difference as compared to SEQ ID NO: 2 selected from: X18A, X19W, X21H, X31M, X34A, X53M. X56A/C, X57C/F/L, X73R, X86C/N/S/Y, X88H/Y, X107G, X13C/L/P, X146L, X147H/K/V, X153A/C/V, X155A/V, X163L, X165F, X171Q, X178W, X190K, X206K, X228G, X233T/V, X235P, X244T, X251V, X259V, X268A, X277A, X286C/H, X312N, X314N, X315G, X316A/C/F/N/S/T, X317L, X319N, X323T, X358K, X366H. X383C/F/I/M/T/V, X395P, X399A, X414I, X415A/G/H/L/V, X417T/V, X424A, X426R, X427Y, X434T, and X450S.

In some embodiments of the engineered polypeptides having transaminase activity, the amino acid sequence does not comprise a residue difference as compared to SEQ ID NO: 2 at positions X9, X45, X177, X211, X294, X324, and X391.

In some embodiments, the engineered transaminase polypeptides can have additional residue differences at other residue positions. In some embodiments, the engineered transaminases can have 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 additional residue differences as compared to SEQ ID NO:2. In some embodiments, the engineered transaminases can have 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 additional residue differences. In some embodiments, the amino acid sequence has additionally 1, 2, 3, 4, 5, 6, 7, 8, 9, 10, 11, 12, 13, 14, 15, 16, 18, 20, 21, 22, 23, 24, or 25 residue differences as compared to SEQ ID NO: 2.

Exemplary engineered polypeptides incorporating the residue differences, including various combinations thereof, and having improved properties (e.g., capable of converting compound (2) to compound (1) in at least 90% diastereomeric excess under suitable reaction conditions) are disclosed in Tables 2A and 2B, and the Examples. The amino acid sequences are provided in the Sequence Listing and include SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204.

In another aspect, the present disclosure provides polynucleotides encoding the engineered polypeptides having transaminase activity, as well as expression vectors comprising the polynucleotides, and host cells capable of expressing the polynucleotides encoding the engineered polypeptides. Exemplary polynucleotide sequences are provided in the Sequence Listing incorporated by reference herein and include SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, and 203.

In some embodiments, the present disclosure also provides methods of manufacturing the engineered transaminase polypeptides, where the method can comprise culturing a host cell capable of expressing a polynucleotide encoding the engineered transaminase polypeptide under conditions suitable for expression of the polypeptide. In some embodiments, the method for manufacturing the engineered transaminase polypeptide can also include: (a) synthesizing a polynucleotide encoding a polypeptide comprising an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, and having one or more residue differences as compared to SEQ ID NO:2 at residue positions selected from: X19, X21, X34, X53, X56, X73, X86, X88, X107, X113, X147, X155, X165, X171, X178, X233, X251, X259, X268, X277, X286, X312, X316, X317, X358, X366, X383, X399, X414, X415, X417, X426, X434, and X450, wherein the residue differences at residue positions X21, X56, X86, X88, X107, X113, X133, X147, X233, X286, X312, X316, X383, X415, X417, and X434, are selected from: X21H, X56A/C, X86C, X88H/Y, X107G, X113L/P, X147H/V, X233V, X286C/H, X312N, X316C/F/G/N/S/T, X383C/F/I/M/T, X415A/G/H/L/V, X417V, and X434T; and (b) expressing the transaminase polypeptide encoded by the polynucleotide. As noted above, the residue differences at residue positions X19, X34, X53, X73, X155, X165, X171, X178, X251, X259, X268, X277, X317, X358, X366, X399, X414, X426, and X450 can be selected from X19W, X34A, X53M, X73R, X155V, X165F, X171Q, X178W, X251V, X259V, X268A, X277A, X317L, X358K, X366H, X399A, X414I, X426R, and X450S. As further provided in the detailed description, additional variations can be incorporated during the synthesis of the polynucleotide to prepare engineered transaminases with corresponding differences in the expressed amino acid sequences.

The structural features of the engineered transaminase polypeptides allow for the conversion of large prochiral ketone substrate compounds, other than compound (2), to their corresponding amine product compounds, optionally in stereometric excess of one chiral amine product over another chiral amino product. Thus, another aspect of the present disclosure are processes using the engineered transaminase polypeptides to catalyze a reaction in which an amino group from an amino donor is transferred to an amino acceptor, wherein the process comprises contacting an engineered transaminase polypeptide of the disclosure with an amino acceptor (e.g., a ketone substrate compound) in the presence of an amino donor (e.g., isopropylamine) under reaction conditions suitable for converting the amino acceptor to an amine compound.

Accordingly, in some embodiments, the present disclosure provides a process for the preparation of an amine compound of Formula (I)

(I)

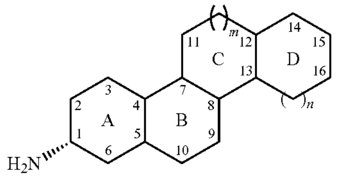

wherein rings A, B, C, and D are as defined above with the proviso that the compound of Formula (I) is not compound (1)

(1)

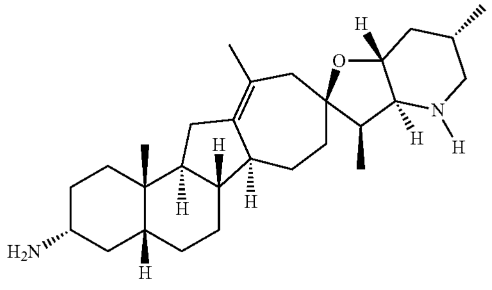

wherein the method comprises contacting the ketone substrate compound of Formula (II), (II)

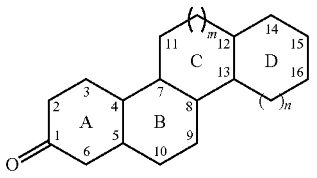

wherein rings A, B, C, and D are as defined above, with an engineered transaminase polypeptide of the present disclosure in the presence of an amino donor under suitable reaction conditions.

In some embodiments of the process for preparing an amine compound of Formula (I), the present disclosure provides a process for preparation of a compound of Formula (Ia)

(Ia)

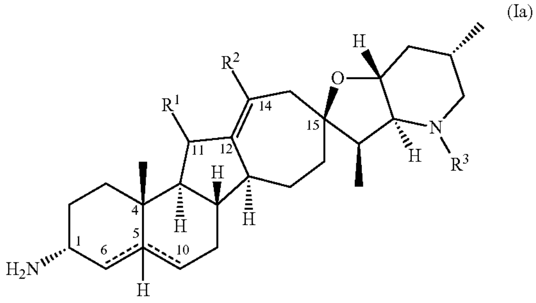

wherein

Rings A and B comprise one of the following:

(a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D comprises an unsaturated C—C bond between positions 12 and 14;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched $(C_1\text{-}C_4)$alkyl, straight-chain or branched $(C_1\text{-}C_4)$alkenyl, and straight-chain or branched $(C_1\text{-}C_3)$alkylamino; and $R^3$ is selected from hydrogen, halo, hydroxy, amino, carboxy, cyano, nitro, thio, optionally substituted $(C_1\text{-}C_6)$alkyl, hydroxy$(C_1\text{-}C_6)$alkyl, optionally substituted $(C_1\text{-}C_6)$alkyloxy, optionally substituted $(C_1\text{-}C_6)$alkylamino, optionally substituted $(C_1\text{-}C_6)$dialkylamino, optionally substituted $(C_1\text{-}C_6)$alkylthio, optionally substituted $(C_1\text{-}C_6)$alkylsulfonyl, optionally substituted $(C_1\text{-}C_6)$alkylsulfinyl, carboxy$(C_1\text{-}C_6)$alkyl, $(C_1\text{-}C_6)$alkyloxycarbonyl, $(C_1\text{-}C_6)$alkylcarbonyloxy, optionally substituted aminocarbonyl, and aminocarbonyl$(C_1\text{-}C_6)$alkyl; wherein the method comprises contacting the ketone substrate compound of Formula (IIa), (IIa)

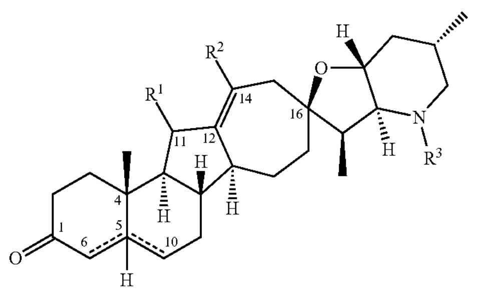

wherein rings A, B, C, and D, and $R^1$, $R^2$, and $R^3$ are as defined above for the compound of Formula (Ia), with an engineered transaminase polypeptide of the present disclosure in the presence of an amino donor under suitable reaction conditions.

In some embodiments of the process for preparing an amine compound of Formula (I), the present disclosure provides a process for preparation of a compound of Formula (Ib)

(Ib)

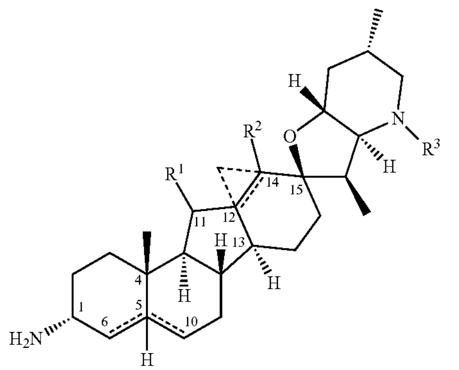

wherein

Rings A and B comprise one of the following:

(a) an unsaturated C—C bond between positions 5 and 6:

(b) an unsaturated C—C bond between positions 5 and 10;

(c) a hydrogen at position 5 cis to the methyl group at position 4; or (d) a hydrogen at position 5 trans to the methyl group at position 4:

Ring D comprises an unsaturated C—C bond between positions 12 and 14, or a bridging cyclopropyl between positions 12 and 14;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched $(C_1\text{-}C_4)$alkyl, straight-chain or branched $(C_1\text{-}C_4)$alkenyl, and straight-chain or branched $(C_1\text{-}C_3)$alkylamino; and $R^3$ is selected from hydrogen, halo, hydroxy, amino, carboxy, cyano, nitro, thio, optionally substituted $(C_1\text{-}C_6)$alkyl, hydroxy$(C_1\text{-}C_6)$alkyl, optionally substituted $(C_1\text{-}C_6)$alkyloxy, optionally substituted $(C_1\text{-}C_6)$alkylamino, optionally substituted $(C_1\text{-}C_6)$dialkylamino, optionally substituted $(C_1\text{-}C_6)$alkylthio, optionally substituted $(C_1\text{-}C_6)$alkylsulfonyl, optionally substituted $(C_1\text{-}C_6)$alkylsulfinyl, carboxy $(C_1-C_6)$alkyl, $(C_1-C_6)$alkyloxycarbonyl, $(C_1-C_6)$alkylcarbonyloxy, optionally substituted aminocarbonyl, and aminocarbonyl$(C_1-C_6)$alkyl;

wherein the method comprises contacting the ketone substrate compound of Formula (IIb), (IIb)

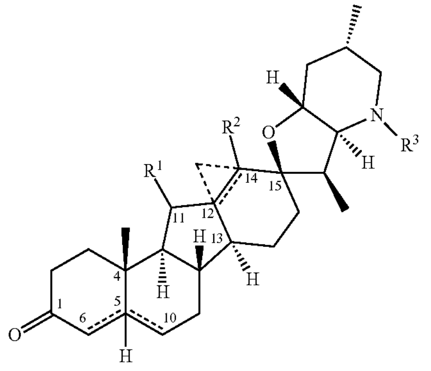

wherein rings A, B, C, and D, and $R^1$, $R^2$, and $R^3$ are as defined above for the compound of Formula (Ib), with an engineered transaminase polypeptide of the present disclosure in the presence of an amino donor under suitable reaction conditions.

In some embodiments of the process for preparing an amine compound of Formula (I), the present disclosure provides a process for preparation of a compound of Formula (Ic)

(Ic)

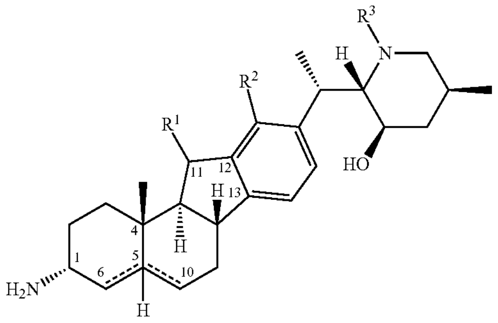

wherein

Rings A and B comprise one of the following:

(a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D is aromatic;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched $(C_1-C_4)$alkyl, straight-chain or branched $(C_1-C_4)$alkenyl, and straight-chain or branched $(C_1-C_3)$alkylamino; and $R^3$ is selected from hydrogen, halo, hydroxy, amino, carboxy, cyano, nitro, thio, optionally substituted $(C_1-C_6)$alkyl, hydroxy$(C_1-C_6)$alkyl, optionally substituted $(C_1-C_6)$alkyloxy, optionally substituted $(C_1-C_6)$alkylamino, optionally substituted $(C_1-C_6)$dialkylamino, optionally substituted $(C_1-C_6)$alkylthio, optionally substituted $(C_1-C_6)$alkylsulfonyl, optionally substituted $(C_1-C_6)$alkylsulfinyl, carboxy$(C_1-C_6)$alkyl, $(C_1-C_6)$alkyloxycarbonyl, $(C_1-C_6)$alkylcarbonyloxy, optionally substituted aminocarbonyl, and aminocarbonyl$(C_1-C_6)$alkyl;

wherein the method comprises contacting the ketone substrate compound of Formula (IIc), (IIc)

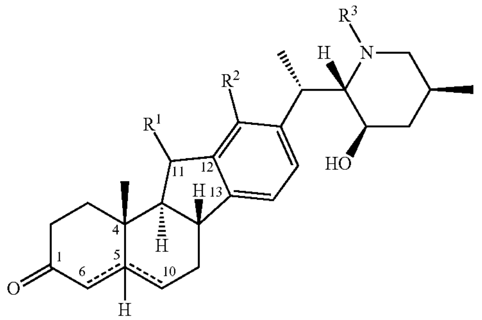

wherein rings A, B, C, and D, and $R^1$, $R^2$, and $R^3$ are as defined above for the compound of Formula (Ic), with an engineered transaminase polypeptide of the present disclosure in the presence of an amino donor under suitable reaction conditions.

In some embodiments of the process for preparing an amine compound of Formula (L), the present disclosure provides a process for preparation of a compound of Formula (Id)

(Id)

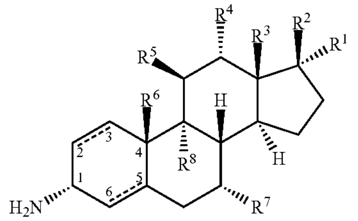

wherein

Ring A comprises an unsaturated C—C bond between positions 2 and 3, or positions 5 and 6;

$R^1$ and $R^2$ are selected independently from hydrogen, halo, hydroxy, amino, carboxy, cyano, nitro, thio, optionally substituted $(C_1-C_6)$alkyl, hydroxy$(C_1-C_6)$alkyl, optionally substituted $(C_1-C_6)$alkyloxy, optionally substituted $(C_1-C_6)$alkylamino, optionally substituted $(C_1-C_6)$dialkylamino, optionally substituted $(C_1-C_6)$alkylthio, optionally substituted $(C_1-C_6)$alkylsulfonyl, optionally substituted $(C_1-C_6)$alkylsulfinyl, carboxy$(C_1-C_6)$alkyl, $(C_1-C_6)$alkyloxycarbonyl, $(C_1-C_6)$alkylcarbonyloxy, optionally substituted aminocarbonyl, aminocarbonyl$(C_1-C_6)$alkyl, optionally substituted cycloalkyl, optionally substituted heterocycloalkyl, optionally substituted aryl, optionally substituted heteroaryl, optionally substituted aryloxy, optionally substituted arylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl;

$R^3$, $R^4$, and $R^5$ are selected independently from hydrogen, halo, hydroxy, amino, carboxy, cyano, nitro, thio, straight-chain or branched ($C_1$-$C_4$)alkyl, straight-chain or branched ($C_1$-$C_4$)alkenyl, and straight-chain or branched ($C_1$-$C_3$)alkylamino; and $R^6$, $R^7$, and $R^8$ are selected independently from hydrogen, halo, hydroxy, and methyl;

wherein the method comprises contacting the ketone substrate compound of Formula (IId), (IId)

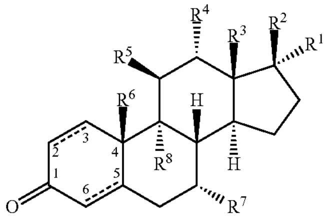

wherein $R^1$, $R^2$, $R^3$, $R^4$, $R^5$, $R^6$, $R^7$, and $R^8$ are as defined above for the compound of Formula (Id), with an engineered transaminase polypeptide of the present disclosure in the presence of an amino donor under suitable reaction conditions.

In some embodiments of the processes for preparing the amine compounds of the present disclosure, the stereoselectivity of the transaminases provides for the preparation of the chiral amine compounds of Formula (I), Formula (Ia), Formula (Ib), Formula (Ic), and Formula (Id) in diastereomeric excess. In some embodiments, the process results in the formation of the chiral amine compound of Formula (I), Formula (Ia), Formula (Ib), Formula (Ic), and Formula (Id) in diastereomeric excess of at least 90%, 95%, 96%, 97%, 98%, 99%, or greater.

As provided herein, the processes using the engineered transaminases can be done under a range of suitable reaction conditions, including, among others, ranges of amine donor, pH, temperature, buffer, solvent system, substrate loading, polypeptide loading, cofactor loading, pressure, and reaction time.

In some embodiments, the suitable reaction conditions for the transamination process can comprise: (a) substrate loading at about 5 g/L to 200 g/L; (b) about 0.1 to 50 g/L of engineered transaminase polypeptide; (c) about 0.1 to 4 M of isopropylamine (IPM); (d) about 0.1 to 10 g/L of pyridoxal phosphate (PLP) cofactor; (e) pH of about 6 to 9; and (f) temperature of about 30 to 60° C.

In some embodiments, the suitable reaction conditions for the transamination process can comprise: (a) substrate loading at about 10 g/L to 150 g/L; (b) about 0.5 to 20 g/L of engineered transaminase polypeptide; (c) about 0.1 to 3 M of isopropylamine (IPM); (d) about 0.1 to 10 g/L of pyridoxal phosphate (PLP) cofactor; (e) about 0.05 to 0.20 M TEA buffer; (f) about 1% to about 45% DMSO; (g) pH of about 6 to 9; and (h) temperature of about 30 to 65° C.

In some embodiments, the suitable reaction conditions for the transamination process can comprise: (a) substrate loading at about 20 to 100 g/L; (b) about 1 to 5 g/L of engineered transaminase polypeptide; (c) about 0.5 to 2 M of isopropylamine (IPM); (d) about 0.2 to 2 g/L of pyridoxal phosphate (PLP) cofactor, (e) about 0.1 M TEA buffer; (f) about 25% DMSO; (e) pH of about 8; and (f) temperature of about 45 to 60° C.

Guidance on the choice of engineered transaminases, preparation of the biocatalysts, the choice of enzyme substrates, and parameters for carrying out the processes are further described in the detailed description that follow.

5. DETAILED DESCRIPTION

As used in this specification and the appended claims, the singular forms "a", "an" and "the" include plural referents unless the context clearly indicates otherwise. Thus, for example, reference to "a polypeptide" includes more than one polypeptide.

Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure.

The section headings used herein are for organizational purposes only and not to be construed as limiting the subject matter described.

5.1 Abbreviations

The abbreviations used for the genetically encoded amino acids are conventional and are as follows:

| Amino Acid | Three-Letter Abbreviation | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | HIS | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon ($C_α$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

5.2 Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Polynucleotide" or "nucleic acid" refers to two or more nucleosides that are covalently linked together. The polynucleotide may be wholly comprised ribonucleosides (i.e., an RNA), wholly comprised of 2'-deoxyribonucleotides (i.e., a DNA) or mixtures of ribo- and 2'-deoxyribonucleosides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. Preferably, such modified or synthetic nucleobases will be encoding nucleobases.

"Aminotransferase" and "transaminase" are used interchangeably herein to refer to a polypeptide having an enzymatic capability of transferring an amino group ($NH_2$) from a primary amine to a carbonyl group (C═O) of an acceptor molecule. Transaminases as used herein include naturally occurring (wild-type) transaminases as well as non-naturally occurring engineered polypeptides generated by human manipulation.

"Amino acceptor" and "amine acceptor," "keto substrate," "keto," and "ketone" are used interchangeably herein to refer to a carbonyl (keto, or ketone) compound which accepts an amino group from a donor amine. In some embodiments, amino acceptors are molecules of the following general formula,

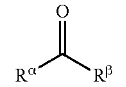

amino acceptor in which each of $R^\alpha$ and $R^\beta$, when taken independently, is an alkyl, cycloalkyl, heterocycloalkyl, aryl, or heteroaryl, which can be unsubstituted or substituted with one or more enzymatically acceptable groups. $R^\alpha$ may be the same or different from $R^\beta$ in structure or chirality. In some embodiments, $R^\alpha$ and $R^\beta$, taken together, may form a ring that is unsubstituted, substituted, or fused to other rings. Amino acceptors include keto carboxylic acids and alkanones (ketones). Typical keto carboxylic acids are α-keto carboxylic acids such as glyoxalic acid, pyruvic acid, oxaloacetic acid, and the like, as well as salts of these acids. Amino acceptors also include substances which are convened to an amino acceptor by other enzymes or whole cell processes, such as fumaric acid (which can be converted to oxaloacetic acid), glucose (which can be convened to pyruvate), lactate, maleic acid, and others. Amino acceptors that can be used include, by way of example and not limitation, 3,4-dihydronaphthalen-1(2H)-one, 1-phenylbutan-2-one, 3,3-dimethylbutan-2-one, octan-2-one, ethyl 3-oxobutanoate, 4-phenylbutan-2-one, 14-(4-bromophenyl)ethanone, 2-methyl-cyclohexamone, 7-methoxy-2-tetralone, 1-hydroxybutan-2-one, pyruvic acid, acetophenone, 3'-hydroxyacetophenone, 2-methoxy-5-fluoroacetophenone, levulinic acid, 1-phenylpropan-1-one, 1-(4-bromophenyl)propan-1-one, 1-(4-nitrophenyl)propan-1-one, 1-phenylpropan-2-one, 2-oxo-3-methylbutanoic acid, 1-(3-trifluoromethylphenyl)propan-1-one, hydroxypropanone, methoxyoxypropanone, 1-phenylbutan-1-one, 1-(2,5-dimethoxy-4-methylphenyl) butan-2-one, 1-(4-hydroxyphenyl)butan-3-one, 2-acetylnaphthalene, phenylpyruvic acid, 2-ketoglutaric acid, and 2-ketosuccinic acid, including both (R) and (S) single isomers where possible.

"Amino donor" or "amine donor" refers to an amino compound which donates an amino group to the amino acceptor, thereby becoming a carbonyl species. In some embodiments, amino donors are molecules of the following general formula,

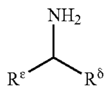

amino donor in which each of $R^\epsilon$ and $R^\delta$, when taken independently, is an alkyl, cycloalkyl, heterocycloalkyl, aryl, or heteroaryl, which is unsubstituted or substituted with one or more enzymatically non-inhibiting groups. $R^\epsilon$ can be the same or different from $R^\delta$ in structure or chirality. In some embodiments, $R^\epsilon$ and $R^\delta$, taken together, may form a ring that is unsubstituted, substituted, or fused to other rings. Typical amino donors that can be used include chiral and achiral amino acids, and chiral and achiral amines. Amino donors that can be used include, by way of example and not limitation, isopropylamine (also referred to as 2-aminopropane), α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-alanine, D-alanine, D,L-alanine, L-aspartic acid, L-lysine, D,L-ornithine, β-alanine, taurine, n-octylamine, cyclohexylamine, 1,4-butanediamine (also referred to as putrescine), 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (S) single isomers where possible and including all possible salts of the amines.

"Chiral amine" refers to amines of general formula $R^{\alpha}$—$CH(NH_2)$—$R^{\beta}$ and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R^{\alpha}$ and $R^{\beta}$ above) also can vary widely and include alkyl, aralkyl, aryl, halo, hydroxy, lower alkyl, lower alkoxy, lower alkylthio, cycloalkyl, carboxy, carbalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

"Pyridoxal-phosphate," "PLP," "pyridoxal-5'-phosphate," "PYP," and "P5P" are used interchangeably herein to refer to the compound that acts as a coenzyme in transaminase reactions. In some embodiments, pyridoxal phosphate is defined by the structure 1-(4'-formyl-3'-hydroxy-2'-methyl-5'-pyridyl)methoxyphosphonic acid. CAS number [54-47-7]. Pyridoxal-5'-phosphate can be produced in vivo by phosphorylation and oxidation of pyridoxol (also known as Vitamin $B_6$). In transamination reactions using transaminase enzymes, the amine group of the amino donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino acceptor). The transfer of the amine group from pyridoxamine phosphate to the amino acceptor produces an amine and regenerates the coenzyme. In some embodiments, the pyridoxal-5'-phosphate can be replaced by other members of the vitamin $B_6$ family, including pyridoxine (PN), pyridoxal (PL), pyridoxamine (PM), and their phosphorylated counterparts; pyridoxine phosphate (PNP), and pyridoxamine phosphate (PMP).

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally occurring" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981. Adv. Appl. Math. 2:482, by the homology alignment algorithm of Needleman and Wunsch, 1970, J. Mol. Biol. 48:443, by the search for similarity method of Pearson and Lipman. 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc, and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989. Proc Natl Acad Sci USA 89:10915). Exemplary determination of sequence alignment and % sequence identity can employ the BESTFIT or GAP programs in the GCG Wisconsin Software package (Accelrys. Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, a "reference sequence based on SEQ ID NO:2 having at the residue corresponding to X34 an alanine" or X34A refers to a reference sequence in which the corresponding residue at X34 in SEQ ID NO:2, which is a threonine, has been changed to alanine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered transaminase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X34 as compared to SEQ ID NO: 2" refers to a change of the amino acid residue at the polypeptide position corresponding to position 34 of SEQ ID NO:2. Thus, if the reference polypeptide of SEQ ID NO: 2 has a threonine at position 34, then a "residue difference at position X34 as compared to SEQ ID NO:2" an amino acid substitution of any residue other than threonine at the position of the polypeptide corresponding to position 34 of SEQ ID NO: 2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some embodiments, where more than one amino acid can appear in a specified residue position, the alternative amino acids can be listed in the form XnY/Z, where Y and Z represent alternate amino acid residues. In some instances (e.g., in Tables 2A and 2B), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. Furthermore, in some instances, a polypeptide of the present disclosure can include one or more amino acid residue differences relative to a reference sequence, which is indicated by a list of the specified positions where changes are made relative to the reference sequence.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid. e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1 below.

TABLE 1

| Residue | Possible Conservative Substitutions |
|---|---|
| A, L, V, I | Other aliphatic (A, L, V, I)<br>Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine), (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered transaminase enzymes comprise insertions of one or more amino acids to the naturally occurring transaminase polypeptide as well as insertions of one or more amino acids to other improved transaminase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the reference polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length transaminase polypeptide, for example the reference engineered transaminase polypeptide of SEQ ID NO: 2.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved transaminase enzymes may be present within a cell, present in the cellular medium, or prepared in various forms, such as lysates or isolated preparations. As such, in some embodiments, the improved transaminase enzyme can be an isolated polypeptide.

"Substantially pure polypeptide" refers to a composition in which the polypeptide species is the predominant species present (i.e., on a molar or weight basis, it is more abundant than any other individual macromolecular species in the composition), and is generally a substantially purified composition when the object species comprises at least about 50 percent of the macromolecular species present by mole or % weight. Generally, a substantially pure transaminase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved transaminase polypeptide is a substantially pure polypeptide composition.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereometric excess.

"Highly stereoselective" refers to a chemical or enzymatic reaction that is capable of converting a substrate, e.g., compound (2), to its corresponding chiral amine product, e.g., compound (1), with at least about 85% stereometric excess.

"Improved enzyme property" refers to a transaminase polypeptide that exhibits an improvement in any enzyme property as compared to a reference transaminase. For the engineered transaminase polypeptides described herein, the comparison is generally made to the wild-type transaminase enzyme, although in some embodiments, the reference transaminase can be another engineered transaminase. Enzyme properties for which improvement is desirable include, but are not limited to, enzymatic activity (which can be expressed in terms of percent conversion of the substrate), thermo stability, solvent stability, pH activity profile, cofactor requirements, refractoriness to inhibitors (e.g., substrate or product inhibition), and stereoselectivity (including enantioselectivity).

"Increased enzymatic activity" refers to an improved property of the engineered transaminase polypeptides, which can be represented by an increased specific activity (e.g., product produced/time/weight protein) or an increased percent conversion of the substrate to the product (e.g., percent conversion of starting amount of substrate to product in a specified time period using a specified amount of transaminase) as compared to the reference transaminase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.2 fold the enzymatic activity of the corresponding wild-type transaminase enzyme, to as much as 2 fold, 5 fold, 10 fold, 20 fold, 25 fold, 50 fold, 75 fold, 100 fold, or more enzymatic activity than the naturally occurring transaminase or another engineered transaminase from which the transaminase polypeptides were derived. Transaminase activity can be measured by any one of standard assays, such as by monitoring changes in spectrophotometric properties of reactants or products. In some embodiments, the amount of products produced can be measured by High-Performance Liquid Chromatography (HPLC) separation combined with UV absorbance or fluorescent detection following derivatization, such as with o-phthaldialdehyde (OPA). Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a transaminase polypeptide can be expressed as "percent conversion" of the substrate to the product.

"Thermostable" refers to a transaminase polypeptide that maintains similar activity (more than 60% to 80% for example) after exposure to elevated temperatures (e.g., 40-80° C.) for a period of time (e.g., 0.5-24 hrs) compared to the wild-type enzyme.

"Solvent stable" refers to a transaminase polypeptide that maintains similar activity (more than e.g., 60% to 80%) after exposure to varying concentrations (e.g., 5-99%) of solvent (ethanol, isopropyl alcohol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 hrs) compared to the wild-type enzyme.

"Thermo- and solvent stable" refers to a transaminase polypeptide that is both thermostable and solvent stable.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The T, values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad. Sci USA 83:8893-8897; Freier et al., 1986, Proc. Natl. Acad. Sci USA 83:9373-9377; Kierzek et al., Biochemistry 25:7840-7846; Rychlik et al., 1990, Nucleic Acids Res 18:6409-6412 (erratum, 1991. Nucleic Acids Res 19:698); Sambrook et al. supra); Suggs et al., 1981, In Developmental Biology Using Purified Genes (Brown et al., eds.), pp. 683-693, Academic Press; and Wetmur, 1991, Crit Rev Biochem Mol Biol 26:227-259. All publications incorporated herein by reference). In some embodiments, the polynucleotide encodes the polypeptide disclosed herein and hybridizes under defined conditions, such as moderately stringent or highly stringent conditions, to the complement of a sequence encoding an engineered transaminase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C., and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the transaminase enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; Mclnerney, J. O, 1998, Bioinformatics 14:372-73; Stenico et al., 1994, Nucleic Acids Res. 222437-46; Wright. F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella,*" 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount. D., Bioinformatics: Sequence and Genome Analysis, Chapter 8, Cold Spring Harbor Laboratory Press, Cold Spring Harbor, N.Y., 2001: Uberbacher, E. C., 1996, Methods Enzymol. 266:259-281; Tiwari et al., 1997, Comput. Appl. Biosci. 13:263-270).

"Control sequence" is defined herein to include all components, which are necessary or advantageous for the expression of a polynucleotide and/or polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refer to those conditions in the biocatalytic reaction solution (e.g., ranges of enzyme loading, substrate loading, cofactor loading, temperature, pH, buffers, co-solvents, etc.) under which a transaminase polypeptide of the present disclosure is capable of converting a substrate compound to a product compound (e.g., conversion of compound (2) to compound (1)). Exemplary "suitable reaction conditions" are provided in the detailed description and illustrated by the Examples.

"Loading", such as in "compound loading" or "enzyme loading" or "cofactor loading" refers to the concentration or amount of a component in a reaction mixture at the start of the reaction.

"Substrate" in the context of a biocatalyst mediated process refers to the compound or molecule acted on by the biocatalyst. For example, an exemplary substrate for the engineered transaminase biocatalysts in the process disclosed herein is compound (2).

"Product" in the context of a biocatalyst mediated process refers to the compound or molecule resulting from the action of the biocatalyst. For example, an exemplary product for the engineered transaminase biocatalysts in the process disclosed herein is compound (1).

"Heteroalkyl, "heteroalkenyl," and "heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, $—NR^{Y}—$, —PH—, —S(O)—, —S(O)2-, $—S(O)NR^{Y}—$, $—S(O)_2NR^{Y}—$, and the like, including combinations thereof, where each $R^{Y}$ is independently selected from hydrogen, alkyl, heteroalkyl, cycloalkyl, heterocycloalkyl, aryl, heteroaryl, and other suitable substituents.

"Aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

"Arylalkyl" refers to an alkyl substituted with an aryl, i.e., aryl-alkyl-groups, preferably having from 1 to 6 carbon atoms inclusively in the alkyl moiety and from 6 to 12 carbon atoms inclusively in the aryl moiety. Such arylalkyl groups are exemplified by benzyl, phenethyl and the like.

"Arylalkenyl" refers to an alkenyl substituted with an aryl, i.e., aryl-alkenyl-groups, preferably having from 2 to 6 carbon atoms inclusively in the alkenyl moiety and from 6 to 12 carbon atoms inclusively in the aryl moiety.

"Arylalkynyl" refers to an alkynyl substituted with an aryl, i.e., aryl-alkynyl-groups, preferably having from 2 to 6 carbon atoms inclusively in the alkynyl moiety and from 6 to 12 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Exemplary cycloalkyl groups include, but are not limited to, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures, including bridged ring systems, such as adamantyl, and the like.

"Cycloalkylalkyl" refers to an alkyl substituted with a cycloalkyl, i.e., cycloalkyl-alkyl-groups, preferably having from 1 to 6 carbon atoms inclusively in the alkyl moiety and from 3 to 12 carbon atoms inclusively in the cycloalkyl moiety. Such cycloalkylalkyl groups are exemplified by cyclopropylmethyl, cyclohexylethyl and the like.

"Cycloalkylalkenyl" refers to an alkenyl substituted with a cycloalkyl, i.e., cycloalkyl-alkenyl-groups, preferably having from 2 to 6 carbon atoms inclusively in the alkenyl moiety and from 3 to 12 carbon atoms inclusively in the cycloalkyl moiety.

"Cycloalkylalkynyl" refers to an alkynyl substituted with a cycloalkyl, i.e., cycloalkyl-alkynyl-groups, preferably having from 2 to 6 carbon atoms inclusively in the alkynyl moiety and from 3 to 12 carbon atoms inclusively in the cycloalkyl moiety.

"Amino" refers to the group —$NH_2$. Substituted amino refers to the group —$NHR^{\eta}$, $NR^{\eta}R^{\eta}$, and $NR^{\eta}R^{\eta}R^{\eta}$, where each $R^{\eta}$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylysulfonylamino, furanyl-oxy-sulfamino, and the like.

"Alkylamino" refers to a —$NHR^{\xi}$ group, where $R^{\xi}$ is an alkyl, an N-oxide derivative, or a protected derivative thereof, e.g., methylamino, ethylamino, n-propylamino, iso-propylamino, n-butylamino, iso-butylamino, tert-butylamino, or methylamino-N-oxide, and the like.

"Arylamino" refers to —$NHR^{\lambda}$, where $R^{\lambda}$ is an aryl group, which can be optionally substituted.

"Heteroarylamino" refers to —$NHR^{\sigma}$, where $R^{\sigma}$ is a heteroaryl group, which can be optionally substituted.

"Aminoalkyl" refers to an alkyl group in which one or more of the hydrogen atoms is replaced with an amino group, including a substituted amino group.

"Oxo" refers to =O

"Oxy" refers to a divalent group —O—, which may have various substituents to form different oxy groups, including ethers and esters.

"Alkoxy" or "alkyloxy" are used interchangeably herein to refer to the group —$OR^{\xi}$, wherein $R^{\xi}$ is an alkyl group, including optionally substituted alkyl groups as also defined herein.

"Aryloxy" refers to —$OR^{\lambda}$ groups, where $R^{\lambda}$ is an aryl group, which can be optionally substituted.

"Heteroaryloxy" refers to —$OR^{\sigma}$, where $R^{\sigma}$ is a heteroaryl group, which can be optionally substituted.

"Carboxy" refers to —COOH.

"Carboxyalkyl" refers to an alkyl substituted with a carboxy group.

"Carbonyl" refers to —C(O)—, which may have a variety of substituents to form different carbonyl groups including acids, acid halides, aldehydes, amides, esters, and ketones.

"Alkylcarbonyl" refers to —C(O)$R^{\xi}$, where $R^{\xi}$ is an alkyl group, which can be optionally substituted.

"Arylcarbonyl" refers to —C(O)$R^{\lambda}$, where $R^{\lambda}$ is an aryl group, which can be optionally substituted.

"Heteroarylcarbonyl" refers to —C(O)$R^{\sigma}$, where $R^{\sigma}$ is a heteroaryl group, which can be optionally substituted.

"Alkyloxycarbonyl" refers to —C(O)O$R^{\xi}$, where $R^{\xi}$ is an alkyl group, which can be optionally substituted.

"Aryloxycarbonyl" refers to —C(O)O$R^{\lambda}$, where $R^{\lambda}$ is an aryl group, which can be optionally substituted.

"Heteroaryloxycarbonyl" refers to —C(O)O$R^{\sigma}$, where $R^{\sigma}$ is a heteroaryl group, which can be optionally substituted.

"Arylalkyloxycarbonyl" refers to —C(O)O$R^{\rho}$, where $R^{\rho}$ is an aryl-alkyl-group, which can be optionally substituted.

"Alkylcarbonyloxy" refers to —OC(O)—$R^{\lambda}$, where R is an alkyl group, which can be optionally substituted.

"Arylcarbonyloxy" refers to —OC(O)$R^{\lambda}$, where R is an aryl group, which can be optionally substituted.

"Heteroarylalkyloxycarbonyl" refers to —C(O)O$R^{\omega}$, where $R^{\omega}$ is a heteroarylalkyl group, which can be optionally substituted.

"Heteroarylcarbonyloxy" refers to —OC(O)$R^{\sigma}$, where $R^{\sigma}$ is an heteroaryl group, which can be optionally substituted.

"Aminocarbonyl" refers to —C(O)$NH_2$. Substituted aminocarbonyl refers to —C(O)$NR^{\eta}R^{\eta}$, where the amino group $NR^{\eta}R^{\eta}$ is as defined herein.

"Aminocarbonylalkyl" refers to an alkyl substituted with an aminocarbonyl group.

"Halogen" or "halo" refers to fluoro, chloro, bromo and iodo.

"Haloalkyl" refers to an alkyl group substituted with one or more halogen. Thus, the term "haloalkyl" is meant to include monohaloalkyls, dihaloalkyls, trihaloalkyls, etc. up to perhaloalkyls. For example, the expression "($C_1$ $C_2$) haloalkyl" includes 1-fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

"Hydroxy" refers to —OH.

"Hydroxyalkyl" refers to an alkyl substituted with one or more hydroxy group.

"Cyano" refers to —CN.

"Nitro" refers to —$NO_2$.

"Thio" or "sulfanyl" refers to —SH. Substituted thio or sulfanyl refers to —S—$R^{\eta}$, where $R^{\eta}$ is an alkyl, aryl or other suitable substituent.

"Alkylthio" refers to —$SR^{\lambda}$, where $R^{\lambda}$ is an alkyl, which can be optionally substituted. Typical alkylthio group include, but are not limited to, methylthio, ethylthio, n-propylthio, and the like.

"Arylthio" refers to —$SR^{\lambda}$, where $R^{\lambda}$ is an aryl, which can be optionally substituted. Typical arylthio groups include, but are not limited to, phenylthio, (4-methylphenyl) thio, pyridinylthio, and the like.

"Heteroarylthio" refers to —$SR^{\sigma}$, where $R^{\sigma}$ is a heteroaryl, which can be optionally substituted.

"Sulfonyl" refers to —$SO_2$—. Substituted sulfonyl refers to —$SO_2$—$R^{\eta}$, where $R^{\eta}$ is an alkyl, aryl or other suitable substituent.

"Alkylsulfonyl" refers to —$SO_2$—$R^{\xi}$, where $R^{\xi}$ is an alkyl, which can be optionally substituted. Typical alkylsulfonyl groups include, but are not limited to, methylsulfonyl, ethylsulfonyl, n-propylsulfonyl, and the like.

"Arysulfonyl" refers to —$SO_2$—$R^{\lambda}$, where $R^{\lambda}$ is an aryl, which can be optionally substituted. Typical arylsulfonyl groups include, but are not limited to, phenylsulfonyl, (4-methylphenyl)sulfonyl, pyridinylsulfonyl, and the like.

"Heteroarylsulfonyl" refers to —$SO_2$—$R^{\sigma}$, where $R^{\sigma}$ is a heteroaryl group, which can be optionally substituted.

"Sulfinyl" refers to —SO—. Substituted sulfinyl refers to —SO—$R^{\eta}$, where $R^{\eta}$ is an alkyl, aryl or other suitable substituent.

"Alkylsulfinyl" refers to —SO—$R^{\xi}$, where $R^{\xi}$ is an alkyl, which can be optionally substituted. Typical alkylsulfinyl groups include, but are not limited to, methylsulfinyl, ethylsulfinyl, n-propylsulfinyl, and the like.

"Arysulfinyl" refers to —SO—$R^{\lambda}$, where $R^{\lambda}$ is an aryl, which can be optionally substituted. Typical arylsulfinyl groups include, but are not limited to, phenylsulfinyl, (4-methylphenyl)sulfinyl, pyridinylsulfinyl, and the like.

"Heteroarylsulfinyl" refers to —SO—$R^{\sigma}$, where $R^{\sigma}$ is a heteroaryl group, which can be optionally substituted.

"Alkylaminosulfonylalkyl" refers to an alkyl substituted with an alkyl-NH—$SO_2$— group.

"Arylsulfonylalkyl" refers to an alkyl substituted with an aryl-$SO_2$— group.

"Heteroarylsulfonylalkyl" refers to an alkyl substituted with a heteroaryl-$SO_2$— group.

"Aminosulfonyl" refers to —$SO_2NH_2$. Substituted aminosulfonyl refers to —$SO_2NR^{\delta}R^{\delta}$, where the amino group —$NR^{\eta}R^{\eta}$ is as defined herein.

"Heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to an alkyl substituted with a heteroaryl, i.e., heteroaryl-alkyl-groups, preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

"Heteroarylalkenyl" refers to an alkenyl substituted with a heteroaryl, i.e., heteroaryl-alkenyl-groups, preferably having from 2 to 6 carbon atoms inclusively in the alkenyl moiety and from 5 to 12 ring atoms inclusively in the heteroaryl moiety.

"Heteroarylalkynyl" refers to an alkynyl substituted with a heteroaryl, i.e., heteroaryl-alkynyl-groups, preferably having from 2 to 6 carbon atoms inclusively in the alkynyl moiety and from 5 to 12 ring atoms inclusively in the heteroaryl moiety.

"Heterocycle". "heterocyclic" and interchangeably "heterocycloalkyl" refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Heterocycloalkylalkyl" refers to an alkyl substituted with a heterocycloalkyl, i.e., heterocycloalkyl-alkyl-groups, preferably having from 1 to 6 carbon atoms inclusively in the alkyl moiety and from 3 to 12 ring atoms inclusively in the heterocycloalkyl moiety.

"Heterocycloalkylalkenyl" refers to an alkenyl substituted with a heterocycloalkyl, i.e., heterocycloalkyl-alkenyl-groups, preferably having from 2 to 6 carbon atoms inclusively in the alkenyl moiety and from 3 to 12 ring atoms inclusively in the heterocycloalkyl moiety.

"Heterocycloalkylalkynyl" refers to an alkynyl substituted with a heterocycloalkyl, i.e., heterocycloalkyl-alkynyl-groups, preferably having from 2 to 6 carbon atoms inclusively in the alkynyl moiety and from 3 to 12 ring atoms inclusively in the heterocycloalkyl moiety.

"Leaving group" generally refers to any atom or moiety that is capable of being displaced by another atom or moiety in a chemical reaction. More specifically, a leaving group refers to an atom or moiety that is readily displaced and substituted by a nucleophile (e.g., an amine, a thiol, an alcohol, or cyanide). Such leaving groups are well known and include carboxylates. N-hydroxysuccinimide ("NHS"), N-hydroxybenzotriazole, a halogen (fluorine, chlorine, bromine, or iodine), and alkyloxy groups. Non-limiting characteristics and examples of leaving groups can be found, for example in Organic Chemistry, 2d ed., Francis Carey (1992), pages 328-331; Introduction to Organic Chemistry, 2d ed., Andrew Streitwieser and Clayton Heathcock (1981), pages 169-171; and Organic Chemistry, 5th Ed., John McMurry, Brooks/Cole Publishing (2000), pages 398 and 408; all of which are incorporated herein by reference.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present disclosure, and is otherwise chemically reasonable.

"Optional" or "optionally" means that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

"Protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts and Greene, "Greene's Protective Groups in Organic Synthesis," $4^{th}$ Ed., Wiley Interscience (2006), and Harrison et al., Compendium of Synthetic Organic Methods. Vols. 1-8, 1971-1996, John Wiley & Sons, NY. Functional groups that can have a protecting group include, but are not limited to, hydroxy, amino, and carboxy groups. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like.

"Polyol" as used herein refers to compounds containing multiple hydroxy groups. In reference to polymers, polyol includes polymers with hydroxyl functional groups. Exemplary polymeric polyols include, by way of example and not limitation, polyethers and polyesters, e.g., polyethylene glycol, polypropylene glycol, poly(tetramethylene) glycol and polytetrahydrofuran.

5.3 Engineered Transaminase Polypeptides

The present disclosure provides engineered polypeptides having transaminase activity, polynucleotides encoding the polypeptides, and methods for using the polypeptides. Where the foregoing description relates to polypeptides, it is to be understood that it also describes the polynucleotides encoding the polypeptides.

Transaminases, also known as aminotransferases, catalyze the transfer of an amino group from a primary amine of an amino donor substrate to the carbonyl group (e.g., a keto or aldehyde group) of an amino acceptor molecule. Transaminases have been identified from a variety of microorganisms including but not limited to *Alcaligenes denitrificans, Bordetella bronchiseptica, Bordetella parapertussis, Brucella melitensis, Burkholderia malle, Burkholderia pseudomallei, Chromobacterium violaceum, Oceanicola granulosus* HTCC2516, *Oceanobacter* sp. RED65, *Oceanospirillum* sp. MED92. *Pseudomonas putida, Ralstonia solanacearum, Rhizobium meliloti, Rhizohium* sp. (strain NGR234). *Bacillus thuringensis, Klebsiella pneumoniae* and *Vibrio fluvialis* (see e.g., Shin et al., 2001, Biosci. Biotechnol, Biochem. 65:1782-1788).

Transaminases are useful for the chiral resolution of racemic amines by exploiting the ability of the transaminases to carry out the reaction in a stereospecific manner, i.e., preferential conversion of one enantiomer to the corresponding ketone, thereby resulting in a mixture enriched in the other enantiomer (see, e.g., Koselewski et al., 2009. Org Lett. 11(21):4810-2). The stereoselectivity of transaminases in the conversion of a ketone to the corresponding amine also make these enzymes useful in the asymmetric synthesis of optically pure amines from the corresponding keto compounds (see, e.g., Höhne et al., "Biocatalytic Routes to Optically Active Amines," Chem Cat Chem 1(1):42-51; Zua and Hua, 2009, Biotechnol J. 4(10):1420-31).

The wild-type ω-transaminase from *Vibrio fluvialis* ω-VfT displays high enantioselectivity for (S)-enantiomers of certain chiral amines and has substrate specificity for chiral aromatic amines (see e.g., Shin and Kim, 2002, J. Org. Chem. 67:2848-2853). The high enantioselectivity of ω-VfT has been applied to chiral resolution of amines (see e.g., Yun, et al., 2004. Biotechnol. Bioeng. 87:772-778; Shin and Kim, 1997, Biotechnol. Bioeng. 55:348-358; M. Hçhne, et al., 2008, Adv. Synth. Catal. 350:802-807). The ω-VfT transaminase has also been used in the asymmetric synthesis of optically pure amines using a prochiral ketone substrate. However, the use of this transaminase in asymmetric synthesis of chiral amines is limited by the unfavorable equilibrium of the reverse reaction (see e.g., Shin and Kim, 1999, Biotechnol. Bioeng. 65, 206-211); inhibition of by the chiral amine product (see e.g., Shin et al., 2001, Biotechnol Bioeng 73:179-187; Yun and Kim, 2008, Biosci. Biotechnol. Biochem. 72(11):3030-3033); low activity on amine acceptors having bulky side chains, such as aromatic groups (see e.g., Shin and Kim, 2002, J. Org. Chem. 67:2848-2853); and low enzyme stability (see e.g., Yun and Kim, supra).

Variant transaminases derived from the ω-VfT transaminase of *Vibrio fluvialis* have been reported that have increased resistance to aliphatic ketones (see e.g., Yun et al., 2005, Appl Environ Micriobiol. 71(8):4220-4224) and broadened amino donor substrate specificity (see e.g., Cho et al., 2008, Biotechnol Bioeng. 99(2):275-84). Patent publications WO2010081053 and US20100209981 (each of which is hereby incorporated by reference herein) describe engineered transaminases derived from ω-VfT that have improved properties for use in synthesis of chiral amine compounds including increased stability to temperature and/or organic solvent, and increased enzymatic activity towards structurally different amino acceptor molecules. Patent publication WO2011159910 (which is hereby incorporated by reference herein) describes engineered transaminases derived from ω-VfT that are optimized for the enantioselective conversion of the substrate 3'-hydroxyacetophenone to the product (S)-3-(1-aminoethyl)-phenol.

The present disclosure relates to engineered transaminase polypeptides derived from the previously engineered transaminases disclosed in patent publication WO2010081053. The engineered transaminases of the present disclosure have been engineered with amino acid residue substitutions that allow for conversion of particularly large amino acceptor compound substrates to the corresponding chiral amine compound products.

Significantly, the present disclosure identifies amino acid residue positions and corresponding amino acid residue substitutions in the engineered transaminase polypeptide that can increase the enzymatic activity, enantioselectivity, stability, and refractoriness to product inhibition, with these particularly large amine acceptor substrates.

The identification of the specific residue positions and substitutions in the engineered transaminase polypeptides of the present disclosure by engineering through directed evolution methods using structure-based rational sequence library design with screening for improved functional properties using an activity assay based on the conversion of the prochiral ketone group of an exemplary large substrate amine acceptor of compound to its corresponding chiral amine product. Specifically, the conversion of the ketone of the cyclopamine analog compound of compound (2) to the corresponding chiral amine compound of compound (1), as shown in Scheme 3.

Scheme 3

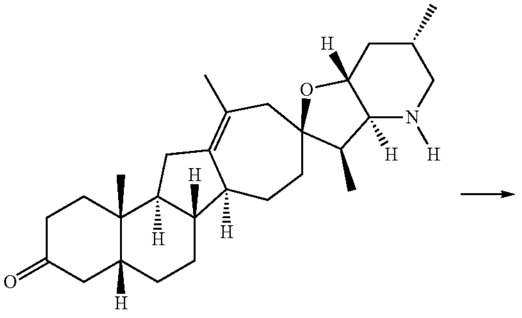

(2)

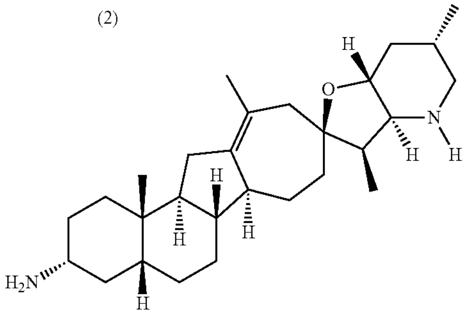

(1)

The engineered transaminase polypeptides of the present disclosure were evolved to efficiently convert the ketone of the exemplary substrate compound (2) to the corresponding chiral amine of the exemplary product compound (1), in the presence of an amino donor under suitable reaction conditions, and in diasteriomeric excess (i.e., in excess of other diastereomers having the opposite enantiomer at the chiral amine center).

The specific structural features and structure-function correlating information of the engineered transaminase polypeptides of the present disclosure also allows for engineered transaminase polypeptides to carry out the conversion of large prochiral ketone substrate compounds, other than compound (2), to the chiral amine compounds, other than compound (1). In some embodiments, the engineered transaminase polypeptides of the present disclosure are capable of converting large prochiral ketone substrate compounds which are structural analogs of compound (2), to the corresponding chiral amine product compounds which are structural analogs of compound (1).

The range of large ketone substrate structural analog compounds capable of undergoing catalytic conversion using the engineered transaminase polypeptides provided by the present disclosure is illustrated by the conversion of compound of Formula (II) to the compound of Formula (I) shown in Scheme 4.

Scheme 4

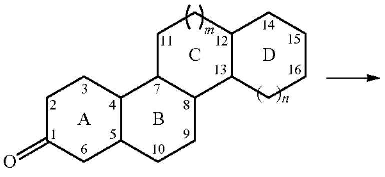

(II)

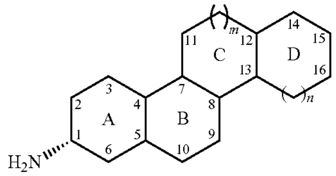

(I)

As shown in Scheme 4, the large substrate ketone compound of Formula (II) has a structure comprising four rings with the prochiral ketone group that is converted to a chiral amine located at position 1 of ring A. Rings A and B are 6-membered carbocyclic rings optionally substituted independently at one or more of positions 2-10; ring C is a 5- or 6-membered carbocyclic ring (i.e., m=0 or 1), optionally substituted at position 11; and ring D is a 5-, 6-, or 7-membered carbocyclic ring (i.e., n=0, 1, or 2), optionally substituted independently at positions 14, 15, and 16. The structural features of the engineered transaminase polypeptides of the disclosure are capable of accommodating substrates compounds of Formula (II) that have large groups substituted at positions 14, 15, and 16 of ring D while maintaining activity in the stereoselective conversion of the ketone at position 1 of ring A of the compound of Formula (II) to a chiral amine. Without being bound by theory, the structure of the engineered transaminase polypeptides of the disclosure allows large groups substituted at positions 14, 15, and 16 of ring D to extend into the solvent surrounding the enzyme, while maintaining the ketone at the 1 position of ring A in the appropriate position of the active site for stereoselective transamination. Additionally, the binding pocket of the engineered transaminase polypeptides of the present disclosure allows for substitutions of smaller groups at certain positions on rings A, B, and C (as described further below), while maintaining activity in the stereoselective conversion of the ketone at position 1 of ring A of the compound of Formula (II) to a chiral amine.

In some embodiments, the engineered transaminase polypeptides of the disclosure are capable of converting the ketone substrate compounds of Formula (II) to the corresponding chiral amine compounds of Formula (I) wherein rings A-D of the compounds can be substituted as follows:

Ring A is a 6-membered carbocyclic ring, optionally including an unsaturated C—C bond between positions 2 and 3 and/or positions 5 and 6, and/or optionally substituted independently positions 2, 3, 4, 5 and 6 with a group selected from halo, hydroxy, and methyl;

Ring B is a 6-membered carbocyclic ring, optionally including an unsaturated C—C bond between positions 5 and 10, and/or optionally substituted independently at one or more of positions 9 and 10 with a group selected from halo, hydroxy, and methyl;

Ring C is a 5- or 6-membered carbocyclic ring (i.e., m=0 or 1), optionally substituted at position 10 with a group selected from halo, hydroxy, methyl, ethyl, and carbonyl;

Ring D is a 5-, 6-, or 7-membered carbocyclic ring (i.e., n=0, 1, or 2), optionally including 1, 2, or 3 unsaturated C—C bonds, and/or optionally substituted independently as follows:

at position 14 with a group selected from halo, hydroxy, amino, carboxy, cyano, nitro, thio, straight-chain or branched ($C_1$-$C_4$)alkyl, straight-chain or branched ($C_1$-$C_4$)alkenyl, straight-chain or branched ($C_1$-$C_3$)alkylamino, and cyclopropyl bridging to position 12;

at position 15 or position 16 with a group selected from halo, hydroxy, amino, carboxy, cyano, nitro, thio, optionally substituted ($C_1$-$C_6$)alkyl, hydroxy($C_1$-$C_6$)alkyl, optionally substituted ($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted arylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl ($C_1$-$C_6$)alkyl, arylsulfonyl($C_1$-$C_6$)alkyl, and heteroarylsulfonyl($C_1$-$C_6$)alkyl.

In some embodiments, the engineered transaminase polypeptides of the disclosure are capable of converting ketone substrate compounds of Formula (II) that are cyclopamine analog compounds such as the compounds of Formula (Ha), wherein Ring C is a 5-membered carbocyclic ring, optionally substituted at position 11, and Ring D is a 7-membered carbocyclic ring substituted at position 16, which can be converted to the chiral amine product of Formula (Ia) as shown in Scheme 5:

Scheme 5

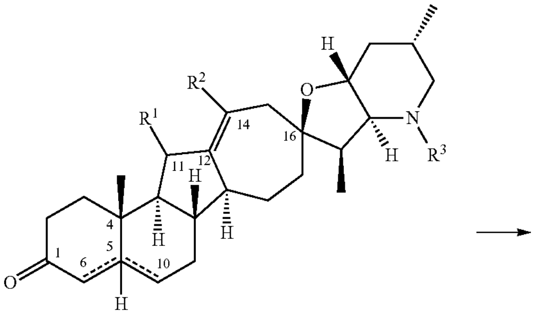

(IIa)

-continued

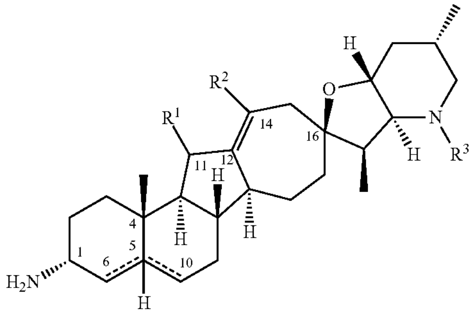

(Ia)

wherein

Rings A and B comprise one of the following:

(a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D comprises an unsaturated C—C bond between positions 12 and 14;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched ($C_1$-$C_4$)alkyl, straight-chain or branched ($C_1$-$C_4$)alkenyl, and straight-chain or branched ($C_1$-$C_3$)alkylamino; and $R^3$ is selected from hydrogen, halo, hydroxy, amino, carboxy, cyano, nitro, thio, optionally substituted ($C_1$-$C_6$)alkyl, hydroxy($C_1$-$C_6$)alkyl, optionally substituted ($C_1$-$C_6$)alkyloxy, optionally substituted ($C_1$-$C_6$)alkylamino, optionally substituted ($C_1$-$C_6$)dialkylamino, optionally substituted ($C_1$-$C_5$)alkylthio, optionally substituted ($C_1$-$C_6$)alkylsulfonyl, optionally substituted ($C_1$-$C_6$)alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, and aminocarbonyl($C_1$-$C_6$)alkyl.

In some embodiments, the engineered transaminase polypeptides of the disclosure are capable of converting ketone substrate compounds of Formula (II) that are cyclopamine analog compounds such as the compounds of Formula (IIb), wherein Ring C is 5-membered carbocyclic ring and Ring D is a 6-membered carbocyclic ring, which can be converted to the chiral amine product of Formula (Ib) as shown in Scheme 6:

Scheme 6

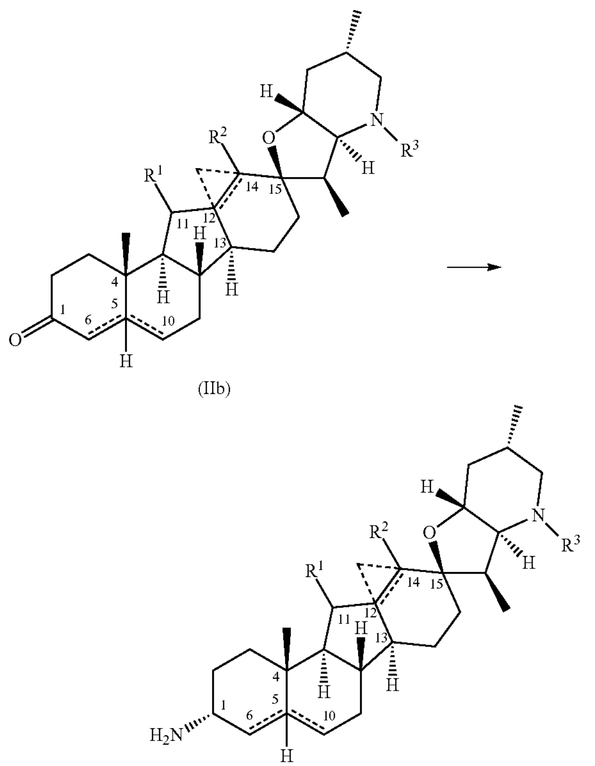

(IIb)

(Ib)

wherein

Rings A and B comprise one of the following:

(a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D comprises an unsaturated C—C bond between positions 12 and 14, or a bridging cyclopropyl between positions 12 and 14;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched ($C_1$-$C_4$)alkyl, straight-chain or branched ($C_1$-$C_4$)alkenyl, and straight-chain or branched ($C_1$-$C_3$)alkylamino; and $R^3$ is selected from hydrogen, halo, hydroxy, amino, carboxy, cyano, nitro, thio, optionally substituted ($C_1$-$C_6$) alkyl, hydroxy($C_1$-$C_6$)alkyl, optionally substituted ($C_1$-$C_6$) alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy ($C_1$-$C_6$)alkyl, ($C_1$-$C_6$)alkyloxycarbonyl, ($C_1$-$C_6$)alkylcarbonyloxy, optionally substituted aminocarbonyl, and aminocarbonyl($C_1$-$C_6$)alkyl.

In some embodiments, the engineered transaminase polypeptides of the disclosure are capable of converting ketone substrate compounds of Formula (II) that are veratramine analog compounds such as the compounds of Formula (IIc), wherein Ring C is 5-membered carbocyclic ring and Ring D is a 6-membered carbocyclic ring, which can be converted to the chiral amine product of Formula (Ic) as shown in Scheme 7:

Scheme 7

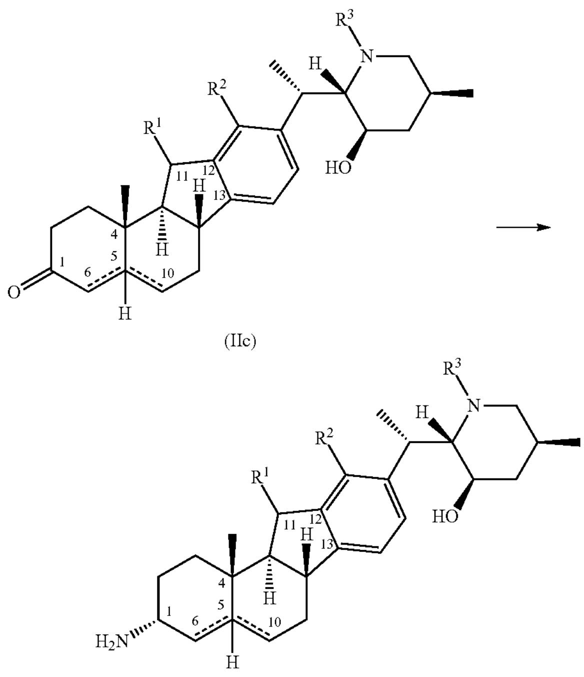

(IIc)

(Ic)

wherein

Rings A and B comprise one of the following:

(a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D is aromatic;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched ($C_1$-$C_4$)alkyl, straight-chain or branched ($C_1$-$C_4$)alkenyl, and straight-chain or branched ($C_1$-$C_3$)alkylamino; and $R^3$ is selected from hydrogen, halo, hydroxy, amino, carboxy, cyano, nitro, thio, optionally substituted ($C_1$-$C_6$) alkyl, hydroxy($C_1$-$C_6$)alkyl, optionally substituted ($C_1$-$C_6$) alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy ($C_1$-$C_6$)alkyl, ($C_1$-$C_6$)alkyloxycarbonyl, ($C_1$-$C_6$)alkylcarbonyloxy, optionally substituted aminocarbonyl, and aminocarbonyl($C_1$-$C_6$)alkyl.

In some embodiments, In some embodiments, the engineered transaminase polypeptides of the disclosure are capable of converting ketone substrate compounds of Formula (II) that are steroid analog compounds such as the compounds of Formula (IId), wherein Ring C is 6-membered carbocyclic ring and Ring D is a 5-membered carbocyclic ring, which can be converted to the chiral amine product of Formula (Id) as shown in Scheme 8:

Scheme 8

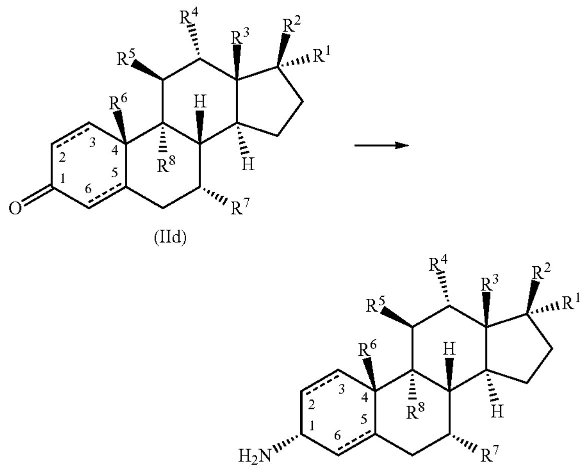

(IId)

(Id)

wherein

Ring A comprises an unsaturated C—C bond between positions 2 and 3, or positions 5 and 6;

$R^1$ and $R^2$ are selected independently from hydrogen, halo, hydroxy, amino, carboxy, cyano, nitro, thio, optionally substituted $(C_1-C_6)$alkyl, hydroxy$(C_1-C_6)$alkyl, optionally substituted $(C_1-C_6)$alkyloxy, optionally substituted $(C_1-C_6)$alkylamino, optionally substituted $(C_1-C_6)$dialkylamino, optionally substituted $(C_1-C_6)$alkylthio, optionally substituted $(C_1-C_6)$alkylsulfonyl, optionally substituted $(C_1-C_6)$alkylsulfinyl, carboxy$(C_1-C_6)$alkyl, $(C_1-C_6)$alkyloxycarbonyl, $(C_1-C_6)$alkylcarbonyloxy, optionally substituted aminocarbonyl, aminocarbonyl$(C_1-C_6)$alkyl, optionally substituted cycloalkyl, optionally substituted heterocycloalkyl, optionally substituted aryl, optionally substituted heteroaryl, optionally substituted aryloxy, optionally substituted arylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl$(C_1-C_6)$alkyl, arylsulfonyl$(C_1-C_6)$alkyl, and heteroarylsulfonyl$(C_1-C_6)$alkyl;

$R^3$, $R^4$, and $R^5$ are selected independently from hydrogen, halo, hydroxy, amino, carboxy, cyano, nitro, thio, straight-chain or branched $(C_1-C_4)$alkyl, straight-chain or branched $(C_1-C_4)$alkenyl, and straight-chain or branched $(C_1-C_3)$alkylamino; and $R^6$, $R^7$, and $R^8$ are selected independently from hydrogen, halo, hydroxy, and methyl.

The engineered transaminase polypeptides adapted for efficient conversion of large ketone substrate compounds of Formula (II) to chiral amine product compounds of Formula (I) have one or more residue differences as compared to the amino acid sequence of the reference engineered transaminase polypeptide of SEQ ID NO: 2. The residue differences are associated with enhancements in enzyme properties, including enzymatic activity, enzyme stability, and resistance to inhibition by the product amine.

In some embodiments, the engineered transaminase polypeptides show increased activity in the conversion of substrate compounds of Formula (I) (e.g., compound (2)) to the amino product compounds of Formula (I) (e.g., compound (1)) in diastereomeric excess in a defined time with the same amount of enzyme as compared to the wild-type or the reference engineered transaminase of SEQ ID NO: 4. In some embodiments, the engineered transaminase polypeptide has at least about 1.2 fold, 1.5 fold, 2 fold, 3 fold, 4 fold, 5 fold, 10 fold, 20 fold, 30 fold, 40 fold, or 50 fold or more the activity as compared to the reference engineered polypeptide represented by SEQ ID NO:4 under suitable reaction conditions.

In some embodiments, the engineered transaminase polypeptides have increased stability to temperature and/or solvents used in the conversion reaction as compared to the wild-type or a reference engineered enzyme. In some embodiments, the engineered transaminase polypeptide has at least 1.2 fold, 1.5 fold, 2 fold, 3 fold, 4 fold, 5 fold, 10 fold or more the stability as compared to the reference polypeptide of SEQ ID NO: 4 under suitable reaction conditions.

In some embodiments, the engineered transaminase polypeptides have increased refractoriness or resistance to inhibition by product chiral amine of compound (1) as compared to the wild-type or a reference engineered enzyme. In some embodiments, the engineered transaminase polypeptide has at least 1.2 fold, 1.5 fold, 2 fold, 3 fold, 4 fold, 5 fold, or more increased resistance to inhibition by the product of compound (1), as compared to the polypeptide represented by SEQ ID NO:4 under suitable reaction conditions, as further described below.

In some embodiments, the engineered transaminase polypeptides are capable of converting the substrate of compound (2) to compound (1) in diastereomeric excess of greater than 90%, 91%, 92%, 93%, 94%, 95%, 96%, 97%, 98%, 99%, 99.5% or greater under suitable reaction conditions (i.e., excess over other diastereomeric product compounds having the opposite enantiomer at the chiral amine center).

In some embodiments, the engineered transaminase polypeptides are capable of converting substrate compound (2) to product compound (1) with increased tolerance for the presence of substrate relative to the reference polypeptide of SEQ ID NO: 4 under suitable reaction conditions. Thus, in some embodiments the engineered transaminase polypeptides are capable of converting the substrate compound (2) to product compound (1) under a substrate loading concentration of at least about 1 g/L, about 5 g/L, about 10 g/L, about 20 g/L, about 30 g/L, about 40 g/L, about 50 g/L, about 70 g/L, about 100 g/L, about 125 g/L, about 150 g/L, about 175 g/L or about 200 g/L or more with a percent conversion of at least about at least about 50%, at least about 60%, at least about 70%, at least about 80%, at least about 90%, at least about 95%, at least about 98%, or at least about 99%, in a reaction time of about 72 h or less, about 48 h or less, about 36 h or less, or about 24 h less, under suitable reaction conditions.

The suitable reaction conditions under which the above-described improved properties of the engineered polypeptides carry out the conversion can be determined with respect to concentrations or amounts of polypeptide, substrate, cofactor, buffer, co-solvent, pH, and/or conditions including temperature and reaction time, as further described below and in the Examples.

The present disclosure provides 200 exemplary engineered transaminase polypeptides having structural features capable of converting large prochiral ketone substrate compounds of Formula (II), which are structural analogs of compound (2), to the corresponding chiral amine product compounds of Formula (I), which are structural analogs of compound (1). The present disclosure provides the sequence structure of the 200 exemplary engineered transaminase polypeptides as SEQ ID NOs: 5-204 in the electronic Sequence Listing file accompanying this disclosure, which is hereby incorporated by reference herein. The odd numbered sequence identifiers (i.e., SEQ ID NOs) refer to the nucleotide sequence encoding the amino acid sequence provided by the even numbered SEQ ID NOs. The present disclosure also provides in Tables 2A and 2B sequence structural information correlating specific amino acid sequence features with the functional activity of the engineered transaminase polypeptides. This structure-function correlation information is provided in the form of specific amino acid residues differences relative to the reference engineered polypeptide of SEQ ID NO: 2 and associated experimentally determined activity data for the 200 exemplary engineered transaminases of SEQ ID NOs: 5-204. The amino acid residue differences are based on comparison to the reference sequence of SEQ ID NO: 2, which has the following 10 amino acid residue differences relative to the sequence of the wild-type ω-VfT polypeptide (Accession: gi|327207066|gb|AEA39183.1|): A9T; N45H; W57L; F86S; V153A; V177L; R211K; M294V; S324G; and T391A. The relative transaminase activity of each exemplary engineered transaminase polypeptide was determined as conversion of the prototype large substrate ketone of compound (2), to the chiral amine product of compound (1) in comparison to the transaminase activity of the engineered transaminase polypeptide of SEQ ID NO: 4 over a set time period and temperature in a high-throughput (HTP) assay, which was used as the primary screen. The engineered transaminase polypeptide of SEQ ID NO: 4 used as the activity reference has the following 8 amino acid residue differences relative to the reference sequence of SEQ ID NO: 2: T34A; L56A; R88H: A153C; A155V; K163F; E315G; and L417T. The HTP Activity assay values in Table 2A were determined using *E. coli*, clear cell lysates in 96 well-plate format of ~200 L volume per well following assay reaction conditions as noted in the table and the Examples.

TABLE 2A

Engineered Polypeptides and Relative Enzyme Improvements Using HTP Preparations

| SEQ ID NO: (nt/aa) | Amino Acid Differences (relative to SEQ ID NO: 2) | HTP Activity[1] (relative to SEQ ID NO: 4) | % de |
|---|---|---|---|
| 3/4 | T34A; L56A; R88H; A153C; A155V; K163F; E315G; L417T; | 1 | 98.6 |
| 5/6 | T34A; N53M; L56A; S86C; R88Y; R146L; A153C; A155V; K163F; Y165F; E315G; R366H; A383V; L417T | 1.57 | n.d. |
| 7/8 | T34A; N53M; L56A; S86C; R88Y; R146L; A153C; A155V; K163F; Y165F; A228G; I259V; E315G; R366H; A383V; L417T | 2.19 | n.d. |
| 9/10 | T34A; N53M; L56A; S86C; R88Y; R146L; A153C; A155V; K163F; Y165F; I259V; E315G; R366H; A383V; R415A; L417T | 1.37 | n.d. |
| 11/12 | T34A; N53M; L56A; S86C; R88Y; R146L; A153C; A155V; K163F; Y165F; I259V; E315G; A383V; R415A; L417T | 1.40 | n.d. |
| 13/14 | T34A; N53M; L56A; S86C; R88Y; R146L; A153C; A155V; K163F; Y165F; A228G; I259V; E315G; R366H; A383V; R415V; L417T | 2.30 | n.d. |
| 15/16 | T34A; N53M; L56A; S86C; R88Y; R146L; A153C; A155V; K163F; Y165F; A228G; I259V; E315G; R366H; A383V; R415A; L417T | 2.31 | n.d. |
| 17/18 | T34A; N53M; L56A; S86C; R88Y; R146L; A153C; A155V; K163F; Y165F; I259V; E315G; R366H; A383V; R415G; L417T | 1.67 | n.d. |
| 19/20 | T34A; N53M; S86C; R88Y; R146L; A153C; A155V; K163F; Y165F; A228G; E315G; R366H; A383V; L417T | 1.63 | n.d. |
| 21/22 | T34A; N53M; S86C; R88Y; R146L; A153C; A155V; K163F; Y165F; I259V; E315G; R366H; A383V; R415V; L417T | 1.90 | n.d. |
| 23/24 | T34A; N53M; L56A; S86C; R88Y; R146L; A153C; A155V; K163F; Y165F; A228G; I259V; T277A; E315G; R366H; A383V; R415G; L417T | 2.25 | n.d. |
| 25/26 | T34A; N53M; L56A; S86C; R88Y; R146L; A153C; A155V; K163F; Y165F; I259V; E315G; R366H; A383V; L417T | 2.71 | n.d. |
| 27/28 | T34A; N53M; L56A; S86C; R88Y; R146L; A153C; A155V; K163F; Y165F; A228G; I251V; I259V; E315G; R366H; A383V; V399A; L417T | 1.46 | n.d. |
| 29/30 | G18A; T34A; L56A; R88H; A153C; A155V; K163F; P233T; E315G; A383V; L417T | 2.11 | n.d. |
| 31/32 | V31M; T34A; L56A; R88H; A153C; A155V; K163F; P233T; P244T; E315G; A383V; L417T; | 1.57 | n.d. |
| 33/34 | V31M; T34A; L56A; R88H; A153C; A155V; K163F; E315G; A383V; L417T; C424A; | 2.23 | n.d. |
| 35/36 | D21H; V31M; T34A; L56A; R88H; A153C; A155V; K163F; P244T; E315G; A383V; L417T; | 1.99 | n.d. |
| 37/38 | V31M; T34A; L56A; R88H; A153C; A155V; K163F; E315G; A383V; L417T; F427Y; | 2.32 | n.d. |
| 39/40 | V31M; T34A; L56A; R88H; A153C; A155V; K163F; P233T; E315G; A383V; L417T; C424A; | 2.42 | n.d. |

TABLE 2A-continued

Engineered Polypeptides and Relative Enzyme Improvements Using HTP Preparations

| SEQ ID NO: (nt/aa) | Ammo Acid Differences (relative to SEQ ID NO: 2) | HTP Activity[1] (relative to SEQ ID NO: 4) | % de |
|---|---|---|---|
| 41/42 | D21H; V31M; T34A; L56A; R88H; R146L; A153C; A155V; K163F; P233T; E315G; A383V; L417T; | 1.79 | n.d. |
| 43/44 | V31M; T34A; L56A; R88H; A153C; A155V; K163F; E315G; A383V; L417T; | 2.21 | n.d. |
| 45/46 | V31M; T34A; L56A; R88H; A153C; A155V; K163F; P244T; E315G; A383V; L417T; | 1.72 | n.d. |
| 47/48 | V31M; T34A; L56A; R88H; R146L; A153C; A155V; K163F; P233T; A235P; P244T; E315G; A383V; L417T; C424A; F427Y; | 2.00 | n.d. |
| 49/50 | V31M; T34A; L56A; R88H; A153C; A155V; K163F; E315G; A383V; L417T; C424A; F427Y; | 2.23 | n.d. |
| 51/52 | V31M; T34A; L56A; R88H; A153C; A155V; K163F; P233T; E315G; A383V; L417T; F427Y; | 2.40 | n.d. |
| 53/54 | V31M; T34A; L56A; R88H; A153C; A155V; K163F; P233T; P244T; E315G; A383V; L417T; F427Y; | 1.58 | n.d. |
| 55/56 | V31M; T34A; L56A; R88H; A153C; A155V; K163F; P233T; E315G; L417T; C424A; | 1.40 | n.d. |
| 57/58 | T34A; L56A; R88H; A153C; A155V; K163F; A383V; E315G; L417T; | 1.69 | n.d. |
| 59/60 | V31M; T34A; L56A; R88H; A153C; A155V; K163F; W147K; P233T; P244T; E315G; A383V; L417T; | 1.94 | n.d. |
| 61/62 | V31M; T34A; L56A; R88H; A153C; A155V; K163F; E315G; L417T; C424A; | 1.44 | n.d. |
| 63/64 | D21H; V31M; T34A; L56A; R88H; A153C; A155V; K163F; E315G; L417T; | 1.48 | n.d. |
| 65/66 | V31M; T34A; L56A; R88H; R146L; A153C; A155V; K163F; E315G; A383V; L417T; F427Y; | 1.62 | n.d. |
| 67/68 | G18A; V31M; T34A; L56A; R88H; A153C; A155V; K163F; P233T; E315G; A383V; L417T; C424A; | 2.33 | n.d. |
| 69/70 | D21H; V31M; T34A; L56A; R88H; A153C; A155V; K163F; E315G; A383V; L417T; F427Y; | 2.61 | n.d. |
| 71/72 | F19W; T34A; L56A; R88H; A153C; A155V; K163F; E315G; E358K; L417T; | 0.24 | n.d. |
| 73/74 | T34A; L56C; R88H; A153C; A155V; K163F; E315G; L417T; | 0.67 | n.d. |
| 75/76 | T34A; L56A; L57F; R88H; A153C; A155V; K163F; E315G; L417T; | 0.93 | n.d. |
| 77/78 | T34A; L56A; L57C; R88H; A153C; A155V; K163F; E315G; L417T; | 1.30 | n.d. |
| 79/80 | T34A; L56A; S86N; R88H; A153C; A155V; K163F; E315G; L417T; | 0.72 | n.d. |
| 81/82 | T34A; L56A; R88H; A153C; A155V; K163L; E315G; A323T; L417T; M434T; | 1.38 | n.d. |
| 83/84 | T34A; L56A; R88H; A153C; A155V; K163F; E315G; R415L; L417T; | 1.39 | n.d. |
| 85/86 | T34A; L56A; R88H; A153C; A155V; K163F; E315G; R415H; L417T; | 1.31 | n.d. |
| 87/88 | T34A; L56A; R88H; A153C; A155V; K163F; T268A; E315G; A383F; L417T; | 1.71 | n.d. |
| 89/90 | T34A; L56A; R88H; A153C; A155V; K163F; N286H; E315G; L417T; | 1.00 | n.d. |
| 91/92 | T34A; L56A; R88H; A153C; A155V; K163F; E315G; E316S; L417T; | 1.85 | n.d. |
| 93/94 | T34A; L56A; R88H; A153C; A155V; K163F; E315G; E316C; L417T; | 1.61 | n.d. |
| 95/96 | T34A; L56A; R88H; A153C; A155V; K163F; E315G; G395P; L417T; | 1.16 | n.d. |
| 97/98 | T34A; L56A; R88H; A153C; A155V; K163F; E315G; E316T; L417T; | 1.67 | n.d. |
| 99/100 | T34A; L56A; R88H; A153C; A155V; K163F; E315G; E316N; L417T; | 1.88 | n.d. |
| 101/102 | T34A; L56A; R88H; A153C; A155V; K163F; E315G; E316F; L417T; | 1.73 | n.d. |
| 103/104 | T34A; L56A; R88H; A153C; A155V; K163F; N286C; E315G; L417T; | 1.56 | n.d. |
| 105/106 | T34A; L56A; R88H; D107G; A153C; A155V; K163F; E315G; L417T; | 1.28 | n.d. |
| 107/108 | T34A; L56A; R88H; Y113P; A153C; A155V; K163F; E315G; L417T; | 1.51 | n.d. |
| 109/110 | T34A; L56A; R88H; Y113L; A153C; A155V; K163F; E315G; L417T; | 1.58 | n.d. |
| 111/112 | T34A; L56A; R88H; Y113C; A153C; A155V; K163F; E315G; L417T; | 1.71 | n.d. |

TABLE 2A-continued

Engineered Polypeptides and Relative Enzyme Improvements Using HTP Preparations

| SEQ ID NO: (nt/aa) | Ammo Acid Differences (relative to SEQ ID NO: 2) | HTP Activity[1] (relative to SEQ ID NO: 4) | % de |
|---|---|---|---|
| 113/114 | T34A; L56A; R88H; W147V; A153C; A155V; K163F; E315G; L417T; | 1.49 | n.d. |
| 115/116 | T34A; L56A; R88H; W147H; A153C; A155V; K163F; E315G; L417T; | 1.54 | n.d. |
| 117/118 | T34A; L56A; R88H; A153C; A155V; K163F; H178W; E315G; L417T; | 1.12 | n.d. |
| 119/120 | T34A; L56A; R88H; A153C; A155V; K163F; P233V; E315G; L417T; | 1.35 | n.d. |
| 121/122 | T34A; L56A; R88H; A153C; A155V; K163F; E315G; A323T; L417T; | 1.81 | n.d. |
| 123/124 | T34A; L56A; R88H; A153C; A155V; K163F; E315G; A383T; L417T; | 2.67 | n.d. |
| 125/126 | T34A; L56A; R88H; A153C; A155V; K163F; E315G; C414I; L417T; | 2.56 | n.d. |
| 127/128 | T34A; L56A; R88H; A153C; A155V; K163F; P233T; E315G; L417T; | 2.67 | n.d. |
| 129/130 | T34A; L56A; R88H; A153C; A155V; K163F; E315G; A383C; L417T; | 1.43 | n.d. |
| 131/132 | T34A; L56A; R88H; A153C; A155V; K163F; E315G; A383I; L417T; | 2.50 | n.d. |
| 133/134 | T34A; L56A; R88H; A153C; A155V; K163F; E315G; L417T; A450S; | 2.61 | n.d. |
| 135/136 | T34A; L56A; R88H; A153C; A155V; K163F; E206K; E315G; E316A; L417T; | 1.44 | n.d. |
| 137/138 | T34A; L56A; R88H; A153C; A155V; K163F; E315G; A383F; L417T; | 1.72 | n.d. |
| 139/140 | T34A; L56A; R88H; A153C; A155V; K163F; E315G; A383M; L417T; | 1.77 | n.d. |
| 141/142 | T34A; L56A; R88H; A153C; A155V; K163F; E315G; L417V; | 1.40 | n.d. |
| 143/144 | T34A; L56A; K73R; R88H; A153C; A155V; K163F; E315G; A383L; L417T; | 1.34 | n.d. |
| 145/146 | V31M; T34A; L56A; L57F; R88H; A153C; A155V; K163F; N286C; E315G; E316N; A383V; R415H; L417T; | 5.61 | 95.4 |
| 147/148 | V31M; T34A; L56A; L57F; R88H; A153C; A155V; K163F; E315G; E316N; A323T; A383V; L417T; | 5.79 | 99.4 |
| 149/150 | V31M; T34A; L56A; L57F; R88H; Y113C; W147V; A153C; A155V; K163F; N286C; E315G; E316S; A323T; A383M; R415H; L417T; A450S; | 7.82 | 93.1 |
| 151/152 | V31M; T34A; L56A; L57F; R88H; Y113L; A153C; A155V; K163F; E190K; P233V; E315G; E316N; A383M; R415H; L417T; A450S; | 5.96 | 94.8 |
| 153/154 | V31M; T34A; L56A; L57F; R88H; D107G; Y113L; W147V; A153C; A155V; K163F; P233V; E315G; E316N; A383T; R415H; L417T; A450S; | 5.84 | 94.1 |
| 155/156 | V31M; T34A; L56A; L57F; R88H; D107G; Y113L; A153C; A155V; K163F; P233T; E315G; E316N; A323T; L417T; | 6.07 | 99.4 |
| 157/158 | V31M; T34A; L56A; L57F; R88H; D107G; W147V; A153C; A155V; K163F; E315G; E316N; A323T; R415H; L417T; | 7.61 | 94.6 |
| 159/160 | V31M; T34A; L56A; L57F; R88H; A153C; A155V; K163F; P233V; E315G; E316N; A323T; A383I; R415H; L417T; A450S; | 8.85 | 93.9 |
| 161/162 | V31M; T34A; L56A; L57F; R88H; W147V; A153C; A155V; K163F; N286C; E315G; E316N; A323T; A383I; C414I; L417T; A450S; | 5.75 | 98.9 |
| 163/164 | V31M; T34A; L56A; L57F; R88H; A153C; A155V; K163F; P233T; N286C; E315G; E316N; A323T; A383I; L417T; A450S; | 5.42 | 98.9 |
| 165/166 | V31M; T34A; L56A; L57F; R88H; W147V; A153C; A155V; K163F; P233V; E315G; E316N; A323T; A383T; R415H; L417T; A450S; | 7.41 | 93.7 |
| 167/168 | V31M; T34A; L56A; L57F; R88H; A153C; A155V; K163F; E315G; E316N; A383I; R415H; L417T; | 5.81 | 95.6 |
| 169/170 | V31M; T34A; L56A; L57F; R88H; A153C; A155V; K163F; N286C; E315G; E316S; A323T; A383I; L417T; | 6.04 | 98.5 |
| 171/172 | V31M; T34A; L56A; L57F; R88H; A153C; A155V; K163F; P233V; E315G; E316S; A323T; A383V; L417T; | 5.68 | 98.7 |
| 173/174 | V31M; T34A; L56A; L57F; R88H; Y113C; A153C; A155V; K163F; P233V; E315G; E316N; A383I; L417T; A450S; | 5.23 | 99.4 |
| 175/176 | T34A; L56A; L57F; R88H; W147H; A153C; A155V; K163F; N286C; E315G; E316S; A323T; R415H; L417T; | 6.80 | 97.0 |
| 177/178 | V31M; T34A; L56A; L57F; R88H; A153C; A155V; K163F; N286C; E316N; A323T; A450S; E315G; L417T; | 5.08 | 99.4 |

TABLE 2A-continued

Engineered Polypeptides and Relative Enzyme Improvements Using HTP Preparations

| SEQ ID NO: (nt/aa) | Ammo Acid Differences (relative to SEQ ID NO: 2) | HTP Activity[1] (relative to SEQ ID NO: 4) | % de |
|---|---|---|---|
| 179/180 | V31M; T34A; L56A; L57F; R88H; W147H; A153C; A155V; K163F; E315G; E316N; A323T; A383I; L417T; A450S; | 6.22 | 99.0 |
| 181/182 | V31M; L57F; W147H; P233V; E316S; A323T; A383I; A450S; T34A; L56A; R88H; A153C; A155V; K163F; E315G; L417T; | 5.62 | 98.8 |
| 183/184 | V31M; T34A; L56A; L57F; R88H; A153C; A155V; K163F; P233V; N286C; E315G; E316N; H319N; A323T; A383T; R415H; L417T; | 5.39 | 96.4 |
| 185/186 | V31M; T34A; L56A; R88H; L57F; Y113C; A153C; A155V; K163F; E315G; E316N; R415H; L417T; | 5.70 | 96.7 |
| 187/188 | V31M; T34A; L56A; L57F; R88H; W147H; A153C; A155V; K163F; E315G; E316N; A383I; L417T; | 5.38 | 99.4 |
| 189/190 | V31M; T34A; L56A; L57F; R88H; W147V; A153C; A155V; K163F; P233V; N286C; E315G; E316N; A323T; A383M; L417T; A450S; | 5.17 | 99.3 |
| 191/192 | V31M; T34A; L56A; L57F; R88H; A153C; A155V; K163F; P233V; E315G; E316N; F317L; A323T; A383V; R415H; L417T; | 5.58 | 95.5 |
| 193/194 | V31M; T34A; N53M; L56A; L57F; S86C; R88Y; R146L; A153C; A155V; K163F; Y165F; I259V; E315G; R366H; A383V; L417T; C424A; | 5.04 | 95.9 |
| 195/196 | T34A; N53M; L56A; L57F; S86C; R88Y; R146L; A153V; A155V; K163F; Y165F; I259V; E312N; I314N; E315G; R366H; A383V; L417T; C424A; | 5.11 | 99.0 |
| 197/198 | T34A; N53M; L56A; L57F; S86C; R88Y; R146L; A153C; A155V; K163F; Y165F; I259V; E315G; R366H; A383V; L417T; C424A; | 6.38 | 98.6 |
| 199/200 | V31M; T34A; N53M; L56A; L57F; S86C; R88Y; R146L; A153V; A155V; K163F; Y165F; L171Q; I259V; E315G; R366H; A383V; L417T; C424A; P426R; | 4.85 | 95.4 |
| 201/202 | T34A; N53M; L56A; S86C; R88Y; R146L; A153C; A155V; K163F; Y165F; I259V; E312N; E315G; E316G; R366H; A383V; L417T; C424A; | 5.59 | 95.8 |
| 203/204 | V31M; T34A; N53M; L56A; L57F; S86C; R88Y; R146L; A153C; A155V; K163F; Y165F; 1259V; E312N; E315G; R366H; A383V; L417T; C424A; | 5.40 | 95.7 |

[1]HTP Activity Improvement (relative to SEQ ID NO: 4) is calculated as the ratio of % conversion of product formed by the engineered transaminase polypeptide of interest to the % conversion of the reference polypeptide of SEQ ID NO: 4 under Reaction Conditions A. % Conversion was quantified by dividing the areas of the product peak by the sum of the areas of the substrate and product peak as determined by HPLC analysis.
Reaction Conditions A: 20 g/L substrate, 10 μL lysate (prepared by adding 200 μL of Lysis Buffer (1 mg/mL lysozyme, 0.5 mg/mL polymyxin B sulfate, 1 mM PLP, 0.1M triethanolamine (TEA), pH 7.0) to *E. coli* expressing polypeptide of interest grown in 96 well plates). 0.5 g/L pyridoxal-5'-phosphate (PLP), 1M isopropylamine (IPM), 25% DMSO, pH 8.0, 60° C., 24 h. Total reaction volume is 200 μL.
"n.d." = not determined In some instances, a shake-flask powder (SFP) and/or downstream processed (DSP) powder assay were used as a secondary screen to assess the properties of the exemplary engineered transaminase polypeptides, the results of which are provided in Table 2B. The SFP and DSP forms provide a more purified powder preparation of the engineered polypeptides. For example, the engineered transaminase in a SFP preparation is approximately 30% of the total protein in the preparation while the engineered transaminase in a DSP preparation is approximately 80% of total protein. Assessment of stability was made by comparing activities at two different temperatures, 55° C., and 60° C.

TABLE 2B

Engineered Transaminase Polypeptides and Relative Improvements Using Shake Flask and DSP Enzyme Preparations

| SEQ ID NO: (nt/aa) | Amino Acid Differences (relative to SEQ ID NO: 2) | % Conversion (24 h at 55° C.) | % de (55° C.) | % Conversion (24 h at 60° C.) | % de (60° C.) |
|---|---|---|---|---|---|
| SFP enzyme preparation assayed using reaction conditions B[1] | | | | | |
| 3/4 | T34A; L56A; R88H; A153C; A155V; K163F; E315G; L417T | 41.2 | 98.6 | 26.0 | 98.4 |
| 7/8 | T34A; N53M; L56A; S86C; R88Y; R146L; A153C; A155V; K163F; Y165F; A228G; I259V; E315G; R366H; A383V; L417T | 96.2 | 85.8 | 84.8 | 83.5 |
| 25/26 | T34A; N53M; L56A; S86C; R88Y; R146L; A153C; A155Y; K163F; | 95.6 | 92.0 | 98.0 | 91.6 |

TABLE 2B-continued

Engineered Transaminase Polypeptides and Relative Improvements Using Shake Flask and DSP Enzyme Preparations

| SEQ ID NO: (nt/aa) | Amino Acid Differences (relative to SEQ ID NO: 2) | % Conversion (24 h at 55° C.) | % de (55° C.) | % Conversion (24 h at 60° C.) | % de (60° C.) |
|---|---|---|---|---|---|
| | Y165F; I259V; E315G; R366H; A383V; L417T | | | | |
| 35/36 | D21H; V31M; T34A; L56A; R88H; A153C; A155V; K163F; P244T; E315G; A383V; L417T; | 79.4 | 96.4 | 52.7 | 95.3 |
| 39/40 | V31M; T34A; L56A; R88H; A153C; A155V; K163F; P233T; E315G; A383V; L417T; C424A; | 95.2 | 96.8 | 66.9 | 95.9 |
| 77/78 | T34A; L56A; L57C; R88H; A153C; A155V; K163F; E315G; L417T; | 67.5 | 96.9 | 31.4 | 97.0 |
| 99/100 | T34A; L56A; R88H; A153C; A155V; K163F; E315G; E316N; L417T; | 86.9 | 98.4 | 23.1 | 100.0 |
| 101/102 | T34A; L56A; R88H; A153C; A155V; K163F; E315G; E316F; L417T; | 81.1 | 97.5 | 20.1 | 100.0 |
| | SFP enzyme preparations assayed using reaction conditions C[2] | | | | |
| 99/100 | T34A; L56A; R88H; A153C; A155V; K163F; E315G; E316N; L417T; | 49.8 | 100.0 | 13.0 | 100.0 |
| 147/148 | V31M; T34A; L56A; L57F; R88H; A153C; A155V; K163F; E315G; E316N; A323T; A383V; L417T; | 93.9 | 100.0 | 94.1 | 100.0 |
| 155/156 | V31M; T34A; L56A; L57F; R88H; D107G; Y113L; A153C; A155V; K163F; P233T; E315G; E316N; A323T; L417T; | 93.7 | 99.3 | 75.4 | 100.0 |
| 159/160 | V31M; T34A; L56A; L57F; R88H; A153C; A155V; K163F; P233V; E315G; E316N; A323T; A383I; R415H; L417T; A450S; | 98.3 | 95.7 | 90.5 | 96.2 |
| 169/170 | V31M; T34A; L56A; L57F; R88H; A153C; A155V; K163F; N286C; E315G; E316S; A323T; A383I; L417T; | 93.9 | 99.4 | 95.6 | 98.4 |
| 171/172 | V31M; T34A; L56A; L57F; R88H; A153C; A155V; K163F; P233V; E315G; E316S; A323T; A383V; L417T; | 96.0 | 99.6 | 94.3 | 99.5 |
| 179/180 | V31M; T34A; L56A; L57F; R88H; W147H; A153C; A155V; K163F; E315G; E316N; A323T; A383I; L417T; A450S; | 96.9 | 100.0 | 91.9 | 100.0 |
| 197/198 | T34A; N53M; L56A; L57F; S86C; R88Y; R146L; A153C; A155V; K163F; Y165F; I259V; E315G; R366H; A383V; L417T; C424A; | 48.1 | 97.2 | 82.0 | 98.0 |
| | DSP enzyme preparations assayed using reaction conditions D[3] | | | | |
| 3/4 | T34A; L56A; R88H; A153C; A155V; K163F; E315G; L417T | 22.3 | 98.6 | 15.2 | 98.6 |
| 99/100 | T34A; L56A; R88H; A153C; A155V; K163F; E315G; E316N; L417T; | 49.3 | >99 | 23.5 | >99 |
| 147/148 | V31M; T34A; L56A; L57F; R88H; A153C; A155V; K163F; E315G; E316N; A323T; A383V; L417T; | 96.1 | >99 | 96.8 | 98.9 |
| 155/156 | V31M; T34A; L56A; L57F; R88H; D107G; Y113L; A153C; A155V; K163F; P233T; E315G; E316N; A323T; L417T; | 96.4 | >99 | 96.7 | >99 |
| 159/160 | V31M; T34A; L56A; L57F; R88H; A153C; A155V; K163F; P233V; E315G; E316N; A323T; A383I; R415H; L417T; A450S; | 96.1 | 97.3 | 97.0 | 95.7 |

TABLE 2B-continued

Engineered Transaminase Polypeptides and Relative Improvements Using Shake Flask and DSP Enzyme Preparations

| SEQ ID NO: (nt/aa) | Amino Acid Differences (relative to SEQ ID NO: 2) | % Conversion (24 h at 55° C.) | % de (55° C.) | % Conversion (24 h at 60° C.) | % de (60° C.) |
|---|---|---|---|---|---|
| 179/180 | V31M; T34A; L56A; L57F; R88H; W147H; A153C; A155V; K163F; E315G; E316N; A323T; A383I; L417T; A450S; | 96.3 | 98.8 | 94.3 | 99.2 |

[1]Reaction Conditions B: 20 g/L substrate, 4 g/L SFP enzyme preparation, 0.5 g/L pyridoxal-5'-phosphate (PLP), 1M isopropylamine (IPM), 25% v/v DMSO, pH 8.0, 55° C. and 60° C. Total reaction volume: 10 mL.
[2]Reaction Conditions C: 20 g/L substrate, 2 g/L SFP enzyme preparation, 0.5 g/L pyridoxal-5'-phosphate (PLP), 1M isopropylamine (IPM), 25% v/v DMSO, pH 8.0, 55° C. and 60° C. Total reaction volume: 10 mL.
Reaction Conditions D: 20 g/L substrate, 2 g/L DSP enzyme preparation, 0.5 g/L pyridoxal-5'-phosphate (PLP), 1M isopropylamine (IPM), 25% v/v DMSO, pH 8.0, 55° C. and 60° C. Total reaction volume: 10 mL.

From an inspection of the amino acid sequences, and results for the 200 exemplary engineered polypeptides of Tables 2A and 2B, improved properties of increased activity, enantioselectivity, and/or stability, that are associated with one or more residue differences as compared to SEQ ID NO:4 at the following residue positions: X18, X19, X21, X31, X34, X53, X56, X57 X73, X86, X88, X107, X113, X133, X147, X155, X163, X165, X171, X178, X190, X206, X228, X233, X235, X244, X251, X259, X268, X277, X286, X312, X314, X316, X317, X319, X323, X358, X366, X383, X395, X399, X414, X415, X417, X424, X426, X427, X434, and X450. The specific amino acid differences at each of these positions that are associated with the improved properties include: X18A; X19W; X21H; X31M; X53M; X56A/C; X57C/F; X73R; X86C/N; X88H/Y; X107G; X113C/L/P; X146L; X147H/K/V; X153V; X155A; X163L; X165F; X171Q; X178W; X190K; X206K; X228G; X233T/V; X235P; X244T; X251V; X259V; X268A; X277A; X286C/H; X312N; X314N; X316A/C/F/N/S/T; X317L; X319N; X323T; X358K; X366H; X383C/F/I/L/M/T/V; X395P; X399A; X414I; X415A/G/H/L/V; X417V; X424A; X426R; X427Y; X434T; and X450S.

In some embodiments, the engineered transaminase polypeptides of the present disclosure comprise amino acid sequences having residue differences as compared to the engineered transaminase represented by SEQ ID NO:4 at residue positions selected from: X19, X21, X34, X53, X56, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450, wherein the residue differences at residue positions X21, X56, X86, X88, X107, X113, X133, X147, X233, X286, X312, X316, X323, X383, X415, X417, and X434, are selected from: X21H, X56A/C, X86C, X88H/Y, X107G, X113L/P, X133A, X147H/V, X233V, X286C/H. X312N, X316C/F/G/N/S/T, X323A, X383C/F/I/M/T, X415A/G/H/L/V, X417V, and X434T.

In some embodiments, the engineered transaminase polypeptides of the present disclosure comprise amino acid sequences having residue differences as compared to the engineered transaminase represented by SEQ ID NO:4 at residue positions selected from: X19, X34, X53, X73, X155, X165, X171, X178, X251, X259, X268, X277, X317, X358, X366, X399, X414, X426, and X450. In some embodiments, the specific amino acid differences at positions X19, X34, X53, X73, X155, X165, X171, X178, X251, X259, X268, X277, X317, X358, X366, X399, X414, X426, and X450 are selected from: X19W, X34A, X53M, X73R, X155V, X165F, X171Q, X178W, X251V, X259V, X268A, X277A, X317L, X358K, X366H, X399A, X414I, X426R, and X450S.

The specific enzyme properties associated with the residues differences as compared to SEQ ID NO:4 at the residue positions above include, among others, enzyme activity, and stability. Residue differences associated with increased enzyme stability are associated with residue differences at residue positions X34, X107, X113, X147, X155, X233, X323, X383, and X450, including the specific residue differences. X34T, X107G, X113L, X147H, X155V, X233T/V, X323T, X383I/V, and X450S. Residue differences associated with increased activity in the conversion of large ketone substrates of Formula (II) to the corresponding chiral amine compound of Formula (I) are associated with residue differences at residue positions X56, X57, X86, X88, X153, X316, X415, and X417, including the specific residue differences. X56A, X57F, X88H, X153C. X316N, X415H, and X417T. Residue differences specifically associated with increased % ee for the conversion of compounds of Formula (II), such as compound (2), to compounds of Formula (I), such as compound (1), include X57F, X153C, and X316N.

As will be appreciated by the skilled artisan, residue differences disclosed in Tables 2A and 2B have no significant deleterious effects on the activity and/or enantioselectivity of the engineered transaminase polypeptides, which are maintain transaminase activity and enantioselectivity (85% d.e. or greater) for the conversion of compound (2) to compound (1). Nearly all of the polypeptides have enantioselectivities equal to or greater than 95% de. Accordingly, the skilled artisan will understand that the residue differences at the residue positions disclosed herein can be used individually or in various combinations to produce engineered transaminase polypeptides having the desired functional properties, including, among others, transaminase activity, stereoselectivity, and stability, in converting large ketone substrate compounds of Formula (II) to chiral amine compounds of Formula (I).

In light of the guidance provided herein, it is further contemplated that any of the exemplary engineered polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204 can be used as the starting amino acid sequence for synthesizing other engineered transaminase polypeptides, for example by subsequent rounds of evolution by adding new combinations of various amino acid differences from other polypeptides in Tables 2A and 2B, and other residue positions described herein. Further improvements may be generated by including amino acid differences at residue positions that had been maintained as unchanged throughout earlier rounds of evolution.

Accordingly, in some embodiments, the present disclosure provides engineered polypeptides having transaminase activity, and optionally improved properties in converting a ketone substrate compound (2) to a chiral amine product compound (1) as compared to a reference polypeptide of SEQ ID NO:4, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO: 2 and one or more residue differences as compared to SEQ ID NO:2 at residue positions selected from X19, X21, X34, X53, X56, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450, wherein the residue differences at residue positions X21, X56, X86, X88, X107, X113, X133, X147, X233, X286, X312, X316, X323, X383, X415, X417, and X434, are selected from: X21H, X56A/C, X86C, X88H/Y, X107G, X113L/P, X133A, X147H/V, X233V, X286C/H, X312N, X316C/F/G/N/S/T, X323A, X383C/F/I/M/T, X415A/G/H/L/V, X417V, and X434T. In some embodiments, the specific amino acid differences at positions X19, X34, X53, X73, X155, X165, X171, X178, X251, X259, X268, X277, X317, X358, X366, X399, X414, X426, and X450 are selected from: X19W, X34A, X53M, X73R, X155V, X165F, X171Q, X178W, X251V, X259V, X268A, X277A, X317L, X358K, X366H, X399A, X414I, X426R, and X450S. In some embodiments, the engineered transaminase polypeptides are capable converting substrate compound (2) to product compound (1) with the improved enantioselectivities described herein, e.g., ≥90% de.

In some embodiments, the engineered polypeptide having transaminase activity of the present disclosure comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, and one or more residue differences as compared to SEQ ID NO:2 at residue positions selected from X19, X21, X34, X53, X56, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450, wherein the residue differences at residue positions X21, X56, X86, X88, X107, X113, X133, X147, X233, X286, X312, X316, X323, X383, X415, X417, and X434, are selected from: X21H, X56A/C, X86C, X88H/Y, X107G, X113L/P, X133A, X147H/V, X233V, X286C/H, X312N, X316C/F/G/N/S/T, X323A, X383C/F/I/M/T, X415A/G/H/L/V, X417V, and X434T. In some embodiments, the specific amino acid differences at positions X19, X34, X53, X73, X155, X165, X171, X178, X251, X259, X268, X277, X317, X358, X366, X399, X414, X426, and X450 are selected from: X19W, X34A, X53M, X73R, X155V, X165F, X171Q, X178W, X251V, X259V, X268A, X277A, X317L, X358K, X366H, X399A, X414I, X426R and X450S. In some embodiments, the reference sequence is selected from SEQ ID NO: 4, 8, 26, 36, 40, 78, 100, 102, 148, 156, 160, 170, 172, 180, and 198. In some embodiments, the reference sequence is SEQ ID NO:4. In some embodiments, the reference sequence is SEQ ID NO: 100. In some embodiments, the reference sequence is SEQ ID NO:148. In some embodiments, the reference sequence is SEQ ID NO:156. In some embodiments, the reference sequence is SEQ ID NO: 160. In some embodiments, the reference sequence is SEQ ID NO: 180.

In some embodiments, the engineered polypeptide having transaminase activity of the present disclosure comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, and at least the following combination of residue differences as compared to SEQ ID NO: 2 of X34A, X56A, X57L, X86S, X88A; X153C, X155V, X163F, X315G, and X417T. In some embodiments, the engineered polypeptide having transaminase activity further comprises a combination of residue differences selected from: (a) X31M, X57F, X316N, X323T, and X383V; (b) X31M, X57F, X107G, X113L, X233T, X316N, X415H, and X450S; (c) X31M, X57F, X233V, X316N, X323T, X383I, X415H, and X450S; and (d) X31M, X57F, X147H, X316N, X323T, X383I, X415H, and X450S.

As will be appreciated by the skilled artisan, in some embodiments, one or a combination of residue differences above that is selected can be conserved in the engineered transaminases as a core sequence (or feature), and additional residue differences at other residue positions incorporated into the core sequence to generate additional engineered transaminase polypeptides with improved properties. Accordingly, it is to be understood for any engineered transaminase containing one or a subset of the residue differences above, the present disclosure contemplates other engineered transaminases that comprise the one or subset of the residue differences, and additionally one or more residue differences at the other residue positions disclosed herein. By way of example and not limitation, an engineered transaminase comprising a residue difference at residue position X316, can further incorporate one or more residue differences at the other residue positions, e.g., X19, X21, X34, X53, X56, X73, X86, X88, X107, X13, X133, X147, X155, X165, X171, X178, X233, X251, X259, X268, X277, X286, X312, X317, X323, X358, X366, X383, X399, X414, X415, X417, X426, X434, and X450. Another example is an engineered transaminase comprising a residue difference at residue position X56, which can further comprise one or more residue differences at the other residue positions, e.g., X19, X21, X34, X53, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450. For each of the foregoing embodiments, the engineered transaminase can further comprise additional residue differences selected from: X18A; X19W; X21H; X31M; X53M; X56A/C; X57C/F; X73R; X86C/N; X88H/Y; X107G; X13C/L/P; X146L; X147H/K/V; X153V; X155A; X163L; X165F;

X171Q; X178W; X190K; X206K; X228G; X233T/V; X235P; X244T; X251V; X259V; X268A; X277A; X286C/H; X312N; X314N; X316A/C/F/N/S/T; X317L; X319N; X323T; X358K; X366H; X383C/F/I/L/M/T/V; X395P; X399A; X414I; X415A/G/H/UV; X417V; X424A; X426R; X427Y; X434T; and X450S.

In some embodiments, the engineered transaminase polypeptide is capable of converting the substrate compound (2) to the product compound (1) with at least 1.2 fold, 1.5 fold, 2 fold, 3 fold, 4 fold, 5 fold, 10 fold, or more activity relative to the activity of the reference polypeptide of SEQ ID NO: 4. In some embodiments, the engineered transaminase polypeptide capable of converting the substrate compound (2) to the product compound (1) with at least 1.2 fold, 1.5 fold, 2 fold, 3 fold, 4 fold, 5 fold, 10 fold, or more activity relative to the activity of the reference polypeptide of SEQ ID NO:4 comprises an amino acid sequence having one or more residue differences as compared to SEQ ID NO:4 selected from: X34T, X107G, X113L, X147H, X155V, X233T/V, X323T, X383I/V, and X450S.

In some embodiments, the engineered transaminase polypeptide capable of converting the substrate compound (2) to the product compound (1) with at least 1.2 fold the activity relative to SEQ ID NO:4 comprises an amino acid sequence selected from: SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 78, 82, 84, 86, 88, 92, 94, 96, 98, 100, 102, 104, 106, 108, 110, 112, 114, 116, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204.

In some embodiments, the engineered transaminase polypeptides have increased stability to temperature and/or solvents used in the conversion reaction as compared to the reference engineered transaminase of SEQ ID NO: 4. In some embodiments, the engineered transaminase polypeptide has at least 1.2 fold, 1.5 fold, 2 fold, 3 fold, 4 fold, 5 fold, 10 fold or more stability than the reference polypeptide of SEQ ID NO: 4, as measured by relative activity at 60° C. compared to activity at 55° C. under the same assay conditions. In some embodiments, the engineered transaminase polypeptide having at least 1.2 fold increased stability as compared to the polypeptide of SEQ ID NO: 4 comprises an amino acid sequence having one or more residue differences as compared to SEQ ID NO: 2 selected from: X34T, X107G, X113L, X147H, X155V, X233T/V, X323T, X383I/V, and X450S.

In some embodiments, the engineered transaminase polypeptide is capable of converting at least 90% or more, 91% or more, 92% or more, 93% or more, 94% or more, or 95% or more of compound (2) to compound (1) in 24 h or less, at a substrate loading of at least about 20 g/L under the Reaction Conditions B, C, or D of Table 2B. In some embodiments, the engineered transaminase polypeptide is capable of converting at least 90% or more of compound (2) to compound (1) in 24 h or less at a substrate loading of at least about 20 g/L at 55° C. In some embodiments, the engineered transaminase polypeptide capable of converting at least 90% or more of compound (2) to compound (1) in 24 h or less at a substrate loading of at least about 20 g/L under conditions at 55° C. comprises an amino acid sequence selected from SEQ ID NO: 8, 26, 40, 148, 156, 160, 170, 172, and 180.

In some embodiments, the engineered polypeptide of the present disclosure having transaminase activity, e.g., in the conversion of a substrate compound (2) to product compound (1), has an amino acid sequence comprising a sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204.

In some embodiments, the engineered transaminase having transaminase activity comprises an amino acid sequence having at least 80%, 85%, 86%, 87%, 88%, 89%, 90%, 91%, 92%, 93%, 94%, 95%, 96%, 97%, 98%, or 99% identity to one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, and the amino acid residue differences as compared to SEQ ID NO:2 present in any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, as provided in Tables 2A and 2B.

In addition to the residue positions specified above, any of the engineered transaminase polypeptides disclosed herein can further comprise other residue differences relative to SEQ ID NO:2 at other residue positions, i.e., residue positions other than X18, X19, X21, X31, X34, X53, X56, X57 X73, X86, X88, X107, X113, X133, X147, X155, X163, X165, X171, X178, X190, X206, X228, X233, X235, X244, X251, X259, X268, X277, X286, X312, X314, X316, X317, X319, X323, X358, X366, X383, X395, X399, X414, X415, X417, X424, X426, X427, X434, and X450. Residue differences at these other residue positions provide for additional variations in the amino acid sequence without adversely affecting the ability of the polypeptide to carry out the transaminase reaction, such as the conversion of compound (2) to compound (1). Accordingly, in some embodiments, in addition to the amino acid residue differences of any one of the engineered transaminase polypeptides selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, the sequence can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, or 1-50 residue differences at other amino acid residue positions as compared to the SEQ ID NO: 2. In some embodiments, the number of amino acid residue differences as compared to the reference sequence can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45 or 50 residue positions. The residue difference at these other positions can include conservative changes or non-conservative changes. In some embodiments, the residue differences can comprise conservative substitutions and non-conservative substitutions as compared to the wild-type transaminase polypeptide of *V. fluvialis* or the engineered transaminase polypeptide of SEQ ID NO: 2.

Amino acid residue differences at other positions relative to the wild-type *V. fluvialis* or the reference sequence of SEQ ID NO: 2 and the effect of these differences on enzyme function are described for other engineered transaminase polypeptides in patent publications WO2010081053, US20100209981, and WO2011159910; Yun et al., 2005, Appl Environ Micriobiol., 71(8):4220-4224); and Cho et al., 2008. Biotechnol Bioeng. 99(2):275-84; all of which are incorporated herein by reference. Accordingly, in some embodiments, one or more of the amino acid differences as compared to the sequence of SEQ ID NO: 2 can also be introduced into an engineered transaminase polypeptide of the present disclosure at residue positions selected from X4; X6; X12; X18; X30; X44; X56; X81; X82; X85; X95; X112; X122; X127; X130; X157; X164; X166; X167; X174; X181; X208; X228; X253; X256; X272; X285; X286; X293; X297; X302; X311; X312; X316; X317; X319; X320; X321; X332; X385; X407; X408; X409; X415; X418; X431; X434; X438; X444; and X446. In particular, the amino acid residues at the foregoing positions can be selected from the following: X4R/Q/L; X6R/I/N; X12A/G/K; X18A/V/L/I; X30A; X44A; X56V; X81D; X82H; X85A/S/V/T/N/C/G; X95T; X112I; X122E; X127L; X130G/M/A/V/L/I; X157T; X164N/Q/S/T/G/M/A/V/L/I; X166S; X167K/R; XI 74E/D; X181R; X2081; X228G/T; X253M; X256A; X272A; X285H; X286N/Q/S/T; X293N/Q/S/T; X297A; X302K; X311V; X312D/E; X316K/H/P; X317L/M/Y; X319Q/G/M/N/V; X320A/K; X321L/M/I; X332N/Q/S/T; X385R; X407S; X408A; X409G; X415M/L; X418V/N/Q/S/T; X431D; X434V; X438L; X444V; and X446V. Guidance on the choice of the amino acid residues at these residue positions and their effect on desirable enzyme properties can be found in the cited references.

In some embodiments, the present disclosure also provides engineered transaminase polypeptides that comprise a fragment of any of the engineered polypeptides described herein that retains the functional activity and/or improved property of that engineered transaminase. Accordingly, in some embodiments, the present disclosure provides a polypeptide fragment having transaminase activity, such as in converting compound (2) to compound (1) under suitable reaction conditions, wherein the fragment comprises at least about 80%, 90%, 95%, 96%, 97%, 98%, or 99% of a full-length amino acid sequence of an engineered transaminase polypeptide of the present disclosure, such as an exemplary engineered transaminase polypeptide selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204.

In some embodiments, the engineered transaminase polypeptide can have an amino acid sequence comprising a deletion of any one of the engineered transaminase polypeptides described herein, such as the exemplary engineered polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204. Thus, for each and every embodiment of the engineered transaminase polypeptides of the disclosure, the amino acid sequence can comprise deletions of one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the transaminase polypeptides, where the associated functional activity and/or improved properties of the engineered transaminase described herein is maintained. In some embodiments, the deletions can comprise 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residues. In some embodiments, the number of deletions can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residues. In some embodiments, the deletions can comprise deletions of 1, 2, 3, 4, 5, 6, 7, 8, 9, 10, 11, 12, 13, 14, 15, 16, 18, 20, 21, 22, 23, 24, or 25 amino acid residues.

In some embodiments, the engineered transaminase polypeptide herein can have an amino acid sequence comprising an insertion as compared to any one of the engineered transaminase polypeptides described herein, such as the exemplary engineered polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204. Thus, for each and every embodiment of the transaminase polypeptides of the disclosure, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, 20 or more amino acids, 30 or more amino acids, 40 or more amino acids, or 50 or more amino acids, where the associated functional activity and/or improved properties of the engineered transaminase described herein is maintained. The insertions can be to amino or carboxy terminus, or internal portions of the transaminase polypeptide.

In some embodiments, the engineered transaminase polypeptide herein can have an amino acid sequence comprising a sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, and optionally one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

In some embodiments, the present disclosure provides an engineered polypeptide having transaminase activity, which polypeptide comprises an amino acid sequence having at least 80%, 85%, 86%, 87%, 88%, 89%, 90%, 91%, 92%, 93%, 94%, 95%, 96%, 97%, 98%, or 99% identity to a sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, with the proviso that the amino acid sequence is not identical to (that is, it excludes) any of the exemplary engineered transaminase polypeptide amino acid sequences disclosed in patent application publications WO2010081053. US20100209981, and WO2011159910; Yun et al., 2005. Appl Environ Micriobiol., 71(8):4220-4224); and Cho et al., 2008, Biotechnol Bioeng. 99(2):275-84; all of which are incorporated by reference herein.

In the above embodiments, the suitable reaction conditions for the engineered polypeptides can be those described in Tables 2A and 2B, the Examples, and elsewhere herein.

In some embodiments, the polypeptides of the disclosure can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

It is to be understood that the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (InAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(S-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the engineered transaminase polypeptides can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having transaminase activity of the present disclosure can be immobilized on a solid support such that they retain their improved activity, stereoselectivity, and/or other improved properties relative to the reference polypeptide of SEQ ID NO: 4. In such embodiments, the immobilized polypeptides can facilitate the biocatalytic conversion of the substrate compounds of Formula (II) or other suitable substrates, to the product compound of Formula (I), or corresponding product (e.g., as shown in Schemes 4-8 described herein), and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the engineered transaminase polypeptides of the present disclosure can be carried out using the same engineered transaminase polypeptides bound or immobilized on a solid support.

Methods of enzyme immobilization are well-known in the art. The engineered transaminase polypeptide can be bound non-covalently or covalently. Various methods for conjugation and immobilization of enzymes to solid supports (e.g., resins, membranes, beads, glass, etc.) are well known in the art and described in e.g., Yi et al., "Covalent immobilization of co-transaminase from *Vibrio fluvialis* JS17 on chitosan beads," *Process Biochemistry* 42(5): 895-898 (May 2007); Martin et al., "Characterization of free and immobilized (S)-aminotransferase for acetophenone production," *Applied Microbiology and Biotechnology* 76(4): 843-851 (September 2007); Koszelewski et al., "Immobilization of ω-transaminases by encapsulation in a sol-gel/celite matrix," *Journal of Molecular Catalysis B: Enzymatic*, 63: 39-44 (April 2010); Truppo et al., "Development of an Improved Immobilized CAL-B for the Enzymatic Resolution of a Key Intermediate to Odanacatib," *Organic Process Research & Development*, published online: dx.doi.org/10.1021/op200157c; Hermanson, G. T., Bioconjugate Techniques, Second Edition, Academic Press (2008); Mateo et al., "Epoxy sepabeads: a novel epoxy support for stabilization of industrial enzymes via very intense multipoint covalent attachment," *Biotechnology Progress* 18(3):629-34 (2002); and Bioconjugation Protocols: Strategies and Methods, In Methods in Molecular Biology, C. M. Niemeyer ed., Humana Press (2004); the disclosures of each which are incorporated by reference herein. Solid supports useful for immobilizing the engineered transaminases of the present disclosure include but are not limited to beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the engineered transaminases of the present disclosure include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, the engineered polypeptides can be in various forms, for example, such as an isolated preparation, as a substantially purified enzyme, whole cells transformed with gene(s) encoding the enzyme, and/or as cell extracts and/or lysates of such cells. The enzymes can be lyophilized, spray-dried, precipitated or be in the form of a crude paste, as further discussed below.

In some embodiments, the polypeptide described herein can be provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the polypeptides can be provided on the solid support in the form of an array in which the polypeptides are arranged in positionally distinct locations. The array can be used to test a variety of substrate compounds for conversion by the polypeptides. A plurality of supports can be configured on an array at various locations, addressable for robotic delivery of reagents, or by detection methods and/or instruments. Various methods for conjugation to substrates, e.g., membranes, beads, glass, etc. are described in, among others, Hermanson, G. T., Bioconjugate Techniques, $2^{nd}$ Edition, Academic Press: (2008), and Bioconjugation Protocols: Strategies and Methods, In Methods in Molecular Biology, C. M. Niemeyer ed., Humana Press (2004); the disclosures of which are incorporated herein by reference.

In some embodiments, the kits of the present disclosure include arrays comprising a plurality of different engineered ketoreductase polypeptides disclosed herein at different addressable position, wherein the different polypeptides are different variants of a reference sequence each having at least one different improved enzyme property. Such arrays comprising a plurality of engineered polypeptides and methods of their use are described in WO2009008908.

5.4 Polynucleotides Encoding Engineered Polypeptides, Expression Vectors and Host Cells In another aspect, the present disclosure provides polynucleotides encoding the engineered transaminase polypeptides described herein. The polynucleotides may be operatively linked to one or more heterologous regulatory sequences that control gene expression to create a recombinant polynucleotide capable of expressing the polypeptide. Expression constructs containing a heterologous polynucleotide encoding the engineered transaminase can be introduced into appropriate host cells to express the corresponding transaminase polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the improved transaminase enzymes. Thus, having knowledge of a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made encoding the polypeptides described herein by selecting combinations based on the possible codon choices, and all such variations are to be considered specifically disclosed for any polypeptide described herein, including the amino acid sequences presented in Tables 2A and 2B, and disclosed in the sequence listing incorporated by reference herein as SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204.

In various embodiments, the codons are preferably selected to fit the host cell in which the protein is being produced. For example, preferred codons used in bacteria are used for expression in bacteria; preferred codons used in yeast are used for expression in yeast; and preferred codons used in mammals are used for expression in mammalian cells. In some embodiments, all codons need not be replaced to optimize the codon usage of the transaminases since the natural sequence will comprise preferred codons and because use of preferred codons may not be required for all amino acid residues. Consequently, codon optimized polynucleotides encoding the transaminase enzymes may contain preferred codons at about 40%, 50%, 60%, 70%, 80%, or greater than 90% of codon positions of the full length coding region.

In some embodiments, as described above, the polynucleotide encodes an engineered polypeptide having transaminase activity with the properties disclosed herein, such as the ability to convert substrate compound (2) to product compound (1), where the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, and one or more residue differences as compared to the reference polypeptide of SEQ ID NO:2 at residue positions selected from X19, X21, X34, X53, X56, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450, wherein the residue differences at residue positions X21, X56, X86, X88, X107, X113, X133, X147, X233, X286, X312, X316, X323, X383, X415, X417, and X434, are selected from: X21H, X56A/C, X86C, X88H/Y, X107G, X113L/P, X133A, X147H/V, X233V, X286C/H, X312N, X316C/F/G/N/S/T, X323A, X383C/F/I/M/T, X415A/G/H/L/V, X417V, and X434T. In some embodiments, the specific amino acid differences at positions X19, X34, X53, X73, X155, X165, X171, X178, X251, X259, X268, X277, X317, X358, X366, X399, X414, X426, and X450 are selected from: X19W, X34A, X53M. X73R, X155V, X165F, X171Q, X178W, X251V, X259V, X268A, X277A, X317L, X358K, X366H, X399A, X414I, X426R, and X450S. In some embodiments, the reference sequence is selected from SEQ ID NO: 4, 8, 26, 36, 40, 78, 100, 102, 148, 156, 160, 170, 172, 180, and 198. In some embodiments, the reference sequence is SEQ ID NO: 4.

In some embodiments, the reference sequence is SEQ ID NO: 100. In some embodiments, the reference sequence is SEQ ID NO:148. In some embodiments, the reference sequence is SEQ ID NO: 156. In some embodiments, the reference sequence is SEQ ID NO:160. In some embodiments, the reference sequence is SEQ ID NO: 180.

In some embodiments, the polynucleotide encodes an engineered polypeptide having transaminase activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO: 2 at residue positions selected from X19, X21, X34, X53, X56, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450, wherein the residue differences at residue positions X21, X56, X86, X88, X107, X113, X133, X147, X233, X286, X312, X316, X323, X383, X415, X417, and X434, are selected from: X21H, X56A/C, X86C, X88H/Y, X107G, X113L/P, X133A, X147H/V, X233V, X286C/H, X312N, X316C/F/G/N/S/T. X323A, X383C/F/I/M/T, X415A/G/H/L/V. X417V, and X434T.

In some embodiments, the polynucleotide encodes an engineered polypeptide having transaminase activity, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and at least the following combination of residue differences as compared to SEQ ID NO: 2: X34A, X56A, X57L, X86S, X88A; X153C, X155V, X163F, X315G, and X417T. In some embodiments, the polynucleotide encodes a polypeptide that further comprises combination of residue differences as compared to SEQ ID NO: 2 selected from: (a) X31M, X57F, X316N, X323T, and X383V; (b) X31M, X57F, X107G, X113L, X233T, X316N, X415H, and X450S; (c) X31M, X57F, X233V, X316N, X323T, X383I, X415H, and X450S; and (d) X31M, X57F, X147H, X316N. X323T, X383I, X415H, and X450S.

In some embodiments, the polynucleotide encodes an engineered polypeptide having transaminase activity, wherein the polypeptide comprises an amino acid sequence having at least 80%, 85%, 86%, 87% 88%, 89%, 90%, 91%, 92%, 93%, 94%, 95%, 96%, 97%, 98%, or 99% identity to a reference polypeptide selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, with the proviso that the amino acid sequence comprises any one of the set of residue differences as compared to SEQ ID NO: 2 contained in any one of the polypeptide sequences of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, as listed in Tables 2A and 2B.

In some embodiments, the polynucleotide encoding the engineered transaminase comprises a polynucleotide sequence selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, and 203.

In some embodiments, the polynucleotides are capable of hybridizing under highly stringent conditions to a reference polynucleotide sequence selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, and 203, or a complement thereof, and encodes a polypeptide having transaminase activity with one or more of the improved properties described herein. In some embodiments, the polynucleotide capable of hybridizing under highly stringent conditions encodes a transaminase polypeptide comprising an amino acid sequence that has one or more residue differences as compared to SEQ ID NO: 2 at residue positions selected from: X19, X21, X34, X53, X56, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450, wherein the residue differences at residue positions X21, X56, X86, X88, X107, X113, X133, X147, X233, X286, X312, X316, X323, X383, X415, X417, and X434, are selected from: X21H, X56A/C, X86C, X88H/Y, X107G, X113L/P, X133A, X147H/V, X233V, X286C/H, X312N. X316C/F/G/N/S/T, X323A, X383C/F/I/M/T, X415A/G/H/L/V, X417V, and X434T.

In some embodiments, the polynucleotides encode the polypeptides described herein but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered transaminase. In some embodiments, the reference polynucleotide sequence is selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, and 203.

An isolated polynucleotide encoding any of the engineered transaminase polypeptides herein may be manipulated in a variety of ways to provide for expression of the polypeptide. In some embodiments, the polynucleotides encoding the polypeptides can be provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3$^{rd}$ Ed., Cold Spring Harbor Laboratory Press; and Current Protocols in Molecular Biology, Ausubel. F. ed., Greene Pub. Associates, 1998, updates to 2006.

In some embodiments, the control sequences include among others, promoter, leader sequence, polyadenylation sequence, propeptide sequence, signal peptide sequence, and transcription terminator. Suitable promoters can be selected based on the host cells used. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ). *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983. Proc. Natl Acad. Sci. USA 80: 21-25). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase. *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxvsporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae enolase* (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention. For example, exemplary transcription terminators for filamentous fungal host cells can be obtained from the genes for *Aspergillus oryzae* TAKA amylase, *Aspergillus niger* glucoamylase. *Aspergillus nidulans* anthranilate synthase, *Aspergillus niger* alpha-glucosidase, and *Fusarium oxvsporum* trypsin-like protease. Exemplary terminators for yeast host cells can be obtained from the genes for *Saccharomyces cerevisiae enolase, Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces*

*cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region which directs the expressed polypeptide into the secretory pathway of a host cell of choice may be used for expression of the engineered polypeptides. Effective signal peptide coding regions for bacterial host cells are the signal peptide coding regions obtained from the genes for *Bacillus* NCIB 11837 maltogenic amylase, *Bacillus stearothermophilus* alpha-amylase. *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57:109-137. Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase. *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase.

The control sequence may also be a propeptide coding region that codes for an amino acid sequence positioned at the amino terminus of a polypeptide. The resultant polypeptide is referred to as a proenzyme or propolypeptide (or a zymogen in some cases). A propolypeptide can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), Saccharomyces *cerevisiae* alpha-factor, *Rhizomucor miehei* aspartic proteinase, and *Myceliophthora thermophila* lactase (WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

In another aspect, the present disclosure is also directed to a recombinant expression vector comprising a polynucleotide encoding an engineered transaminase polypeptide, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP 1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

In another aspect, the present disclosure provides a host cell comprising a polynucleotide encoding an engineered transaminase polypeptide of the present disclosure, the polynucleotide being operatively linked to one or more control sequences for expression of the transaminase enzyme in the host cell. Host cells for use in expressing the polypeptides encoded by the expression vectors of the present invention are well known in the art and include but are not limited to, bacterial cells, such as *E. coli, Vibrio fluvialis, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. An exemplary host cells are *Escherichia coli* W3110 (ΔfhuA) and BL21.

Accordingly, in another aspect, the present disclosure provides methods of manufacturing the engineered transaminase polypeptides, where the method can comprise culturing a host cell capable of expressing a polynucleotide encoding the engineered transaminase polypeptide under conditions suitable for expression of the polypeptide. The method can further comprise isolated or purifying the expressed transaminases polypeptide, as described herein.

Appropriate culture mediums and growth conditions for the above-described host cells are well known in the art. Polynucleotides for expression of the transaminase may be introduced into cells by various methods known in the art. Techniques include, among others, electroporation, biolistic particle bombardment, liposome mediated transfection, calcium chloride transfection, and protoplast fusion.

For the embodiments herein, the engineered polypeptides and corresponding polynucleotides can be obtained using methods used by those skilled in the art. The parental polynucleotide sequence encoding the wild-type polypeptide of *Vibrio fluvialis* described in Shin et al., 2003, Appl. Microbiol. Biotechnol. 61 (5-6):463-471, and methods of generating engineered transaminase polypeptides with improved stability and substrate recognition properties are disclosed in patent application publications WO2010081053 and US20100209981, incorporated herein by reference.

The engineered transaminases with the properties disclosed herein can be obtained by subjecting the polynucleotide encoding the naturally occurring or engineered transaminase to mutagenesis and/or directed evolution methods, as discussed above. An exemplary directed evolution technique is mutagenesis and/or DNA shuffling as described in Stemmer, 1994, Proc Natl Acad Sci USA 91:10747-10751; WO 95/22625; WO 97/0078; WO 97/35966: WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, Anal. Biochem. 254(2):157-78; Dale et al., 1996, "Oligonucleotide-directed random mutagenesis using the phosphorothioate method," In Methods Mol. Biol. 57:369-74; Smith, 1985, Ann. Rev. Genet. 19:423-462: Botstein et al., 1985, Science 229:1193-1201; Carter, 1986, Biochem. J. 237:1-7; Kramer et al., 1984, Cell, 38:879-887; Wells et al., 1985, Gene 34:315-323; Minshull et al., 1999, Curr Opin Chem Biol 3:284-290; Christians et al., 1999, Nature Biotech 17:259-264; Crameri et al., 1998. Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; Stemmer, 1994, Nature 370:389-391; Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. All publications are incorporated herein by reference.

The clones obtained following mutagenesis treatment can be screened for engineered transaminases having a desired improved enzyme property. For example, where the improved enzyme property desired is thermostability, enzyme activity may be measured after subjecting the enzyme preparations to a defined temperature and measuring the amount of enzyme activity remaining after heat treatments. Clones containing a polynucleotide encoding a transaminase are then isolated, sequenced to identify the nucleotide sequence changes (if any), and used to express the enzyme in a host cell. Measuring enzyme activity from the expression libraries can be performed using the standard biochemistry techniques, such as HPLC analysis following derivatization, e.g., with OPA, of the product amine.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using, e.g., the classical phosphoramidite method described by Beaucage et al., 1981. Tet Lett 22:1859-69, or the method described by Matthes et al., 1984. EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors.

Accordingly, in some embodiments, a method for preparing the engineered transaminase polypeptide can comprise: (a) synthesizing a polynucleotide encoding a polypeptide comprising an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204 and having one or more residue differences as compared to SEQ ID NO: 2 at residue positions selected from: X19, X21, X34, X53, X56, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450, wherein the residue differences at residue positions X21, X56, X86, X88, X107, X113, X133, X147, X233, X286, X312, X316, X323, X383, X415, X417, and X434, are selected from: X21H. X56A/C, X86C, X88H/Y, X107G. X113L/P, X133A, X147H/V, X233V, X286C/H. X312N, X316C/F/G/N/S/T, X323A, X383C/F/I/M/T, X415A/G/H/L/V, X417V, and X434T; and (b) expressing the transaminase polypeptide encoded by the polynucleotide. In some embodiments of the method, the residue differences at residue positions X19, X34, X53, X73, X155, X165, X171, X178, X251, X259, X268, X277, X317, X358, X366, X399, X414, X426, and X450 are selected from X19W, X34A, X53M, X73R, X155V, X165F, X171Q, X178W, X251V, X259V, X268A, X277A, X317L, X358K, X366H, X399A, X414I, X426R, and X450S.

In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

The expressed engineered transaminase can be measured for the desired improved property, e.g., activity, enantioselectivity, stability, and product tolerance, in the conversion of compound (2) to compound (1) by any of the assay conditions described herein.

In some embodiments, any of the engineered transaminase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are provided in Table 2A and the Examples, and also commercially available, e.g., CelLytic B™ from Sigma-Aldrich of St. Louis Mo.

Chromatographic techniques for isolation of the transaminase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved transaminase enzymes. For affinity chromatography purification, any antibody which specifically binds the transaminase polypeptide may be used. For the production of antibodies, various host animals, including but not limited to rabbits, mice, rats, etc., may be immunized by injection with a transaminase polypeptide, or a fragment thereof. The transaminase polypeptide or fragment may be attached to a suitable carrier, such as BSA, by means of a side chain functional group or linkers attached to a side chain functional group.

5.7 Methods of Using the Engineered Transaminase Enzymes

As noted above, the engineered transaminase polypeptides of the present disclosure were evolved to efficiently convert the ketone of the exemplary substrate compound (2) to the corresponding chiral amine of the exemplary product compound (1) in diastereomeric excess, in the presence of an amino donor under suitable reaction conditions. The structural features of the engineered transaminase polypeptides also allow for the conversion of large prochiral ketone substrate compounds, other than compound (2), to their corresponding chiral amine compounds in stereometric excess. Accordingly, in another aspect, the present disclosure provides processes using the engineered transaminase polypeptides to carry out a transamination reaction in which an amino group from an amino donor is transferred to an amino acceptor, e.g., a ketone substrate compound, to produce an amine compound. Generally, the process for performing the transamination reaction comprises contacting or incubating an engineered transaminase polypeptide of the disclosure with an amino acceptor (e.g., a ketone substrate compound) and an amino donor (e.g., isopropylamine) with under reaction conditions suitable for converting the amino acceptor to an amine compound.

In some embodiments, the present disclosure provides a process for the preparation of an amine compound of Formula (I)

(I)

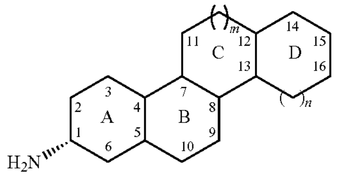

wherein

Ring A is a 6-membered carbocyclic ring, optionally including an unsaturated C—C bond between positions 2 and 3 and/or positions 5 and 6, and/or optionally substituted independently positions 2, 3, 4, 5 and 6 with a group selected from halo, hydroxy, and methyl;

Ring B is a 6-membered carbocyclic ring, optionally including an unsaturated C—C bond between positions 5 and 10, and/or optionally substituted independently at one or more of positions 9 and 10 with a group selected from halo, hydroxy, and methyl;

Ring C is a 5- or 6-membered carbocyclic ring (i.e., m=0 or 1), optionally substituted at position 10 with a group selected from halo, hydroxy, methyl, ethyl, and carbonyl;

Ring D is a 5-, 6-, or 7-membered carbocyclic ring (i.e., n=0, 1, or 2), optionally including 1, 2, or 3 unsaturated C—C bonds, and/or optionally substituted independently as follows: at position 14 with a group selected from halo, hydroxy, amino, carboxy, cyano, nitro, thio, straight-chain or branched ($C_1$-$C_4$)alkyl, straight-chain or branched ($C_1$-$C_4$) alkenyl, straight-chain or branched ($C_1$-$C_3$)alkylamino, and cyclopropyl bridging to position 12; at position 15 or position 16 with a group selected from halo, hydroxy, amino, carboxy, cyano, nitro, thio, optionally substituted ($C_1$-$C_6$) alkyl, hydroxy($C_1$-$C_6$)alkyl, optionally substituted ($C_1$-$C_6$) alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy ($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted arylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl; with the proviso that the compound of Formula (I) is not compound (1)

(1)

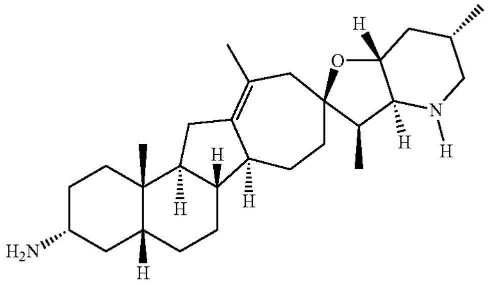

wherein the method comprises contacting the ketone substrate compound of Formula (II), (II)

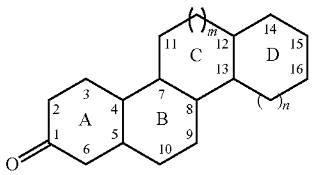

wherein rings A, B, C, and D are as defined above for the compound of Formula (I), with an engineered transaminase polypeptide of the present disclosure in the presence of an amino donor under suitable reaction conditions.

In some embodiments, the engineered transaminase polypeptides of the disclosure are capable of converting cyclopamine analog compounds of Formula (IIa), wherein Ring C is a 5-membered carbocyclic ring, optionally substituted at position 11, and Ring D is a 7-membered carbocyclic ring substituted at position 16, which can be converted to an amine product compound of Formula (Ia) as in Scheme 5.

Scheme 5

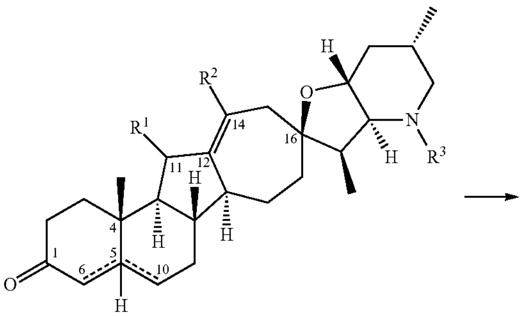

(IIa)

-continued

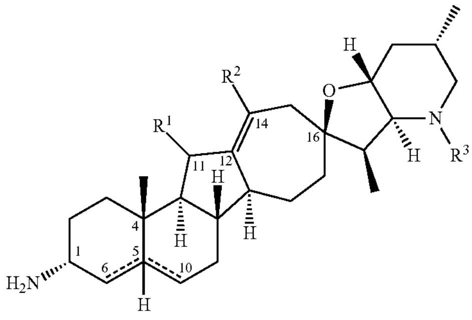

(Ia)

Accordingly, in some embodiments, the present disclosure provides a process for preparation of an amine compound of Formula (Ia)

(Ia)

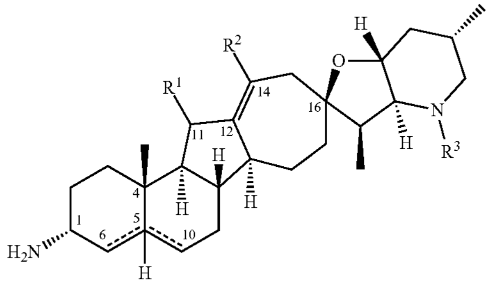

wherein

Rings A and B comprise one of the following:

(a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D comprises an unsaturated C—C bond between positions 12 and 14;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched ($C_1$-$C_4$)alkyl, straight-chain or branched ($C_1$-$C_4$)alkenyl, and straight-chain or branched ($C_1$-$C_3$)alkylamino; and $R^3$ is selected from hydrogen, halo, hydroxy, amino, carboxy, cyano, nitro, thio, optionally substituted ($C_1$-$C_6$) alkyl, hydroxy($C_1$-$C_6$)alkyl, optionally substituted ($C_1$-$C_6$) alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy ($C_1$-$C_6$)alkyl, ($C_1$-$C_6$)alkyloxycarbonyl, ($C_1$-$C_6$)alkylcarbonyloxy, optionally substituted aminocarbonyl, and aminocarbonyl($C_1$-$C_6$)alkyl; with the proviso that the compound of Formula (I) is not compound (1)

(1)

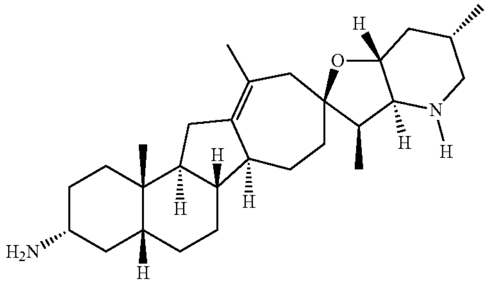

wherein the method comprises contacting the ketone substrate compound of Formula (IIa), (IIa)

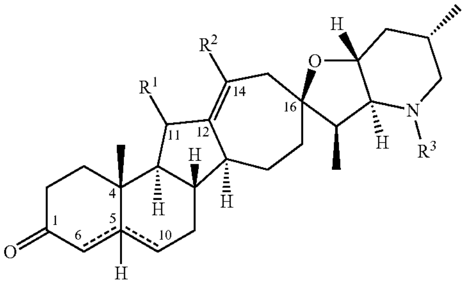

wherein rings A, B, C, and D, and $R^1$, $R^2$, and $R^3$ are as defined above for the compound of Formula (Ia), with an engineered transaminase polypeptide of the present disclosure in the presence of an amino donor under suitable reaction conditions.

In some embodiments, the engineered transaminase polypeptides of the disclosure are capable of converting cyclopamine analog compounds of Formula (IIb), wherein Ring C is 5-membered carbocyclic ring and Ring D is a 6-membered carbocyclic ring, to the chiral amine product compound of Formula (Ib) as shown in Scheme 6:

Scheme 6

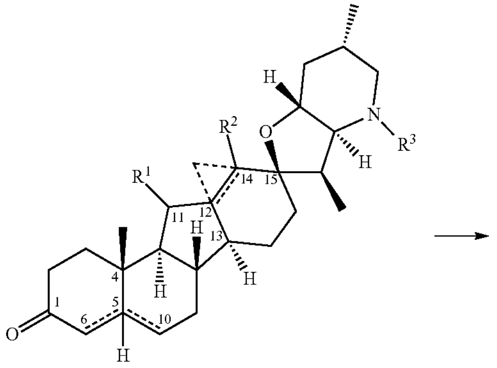

(IIb)

-continued

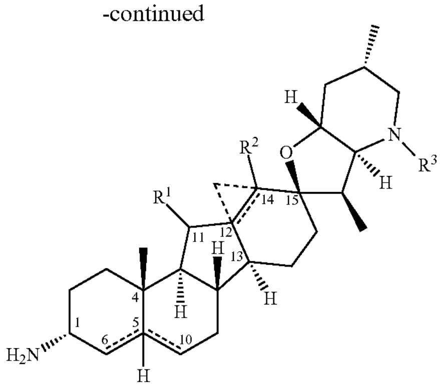

(Ib)

Accordingly, in some embodiments, the present disclosure provides a process for preparation of an amine compound of Formula (Ib)

(Ib)

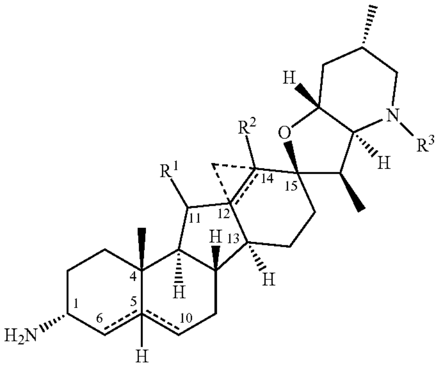

wherein

Rings A and B comprise one of the following:

(a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D comprises an unsaturated C—C bond between positions 12 and 14, or a bridging cyclopropyl between positions 12 and 14:

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched ($C_1$-$C_4$)alkyl, straight-chain or branched ($C_1$-$C_4$)alkenyl, and straight-chain or branched ($C_1$-$C_3$)alkylamino; and $R^3$ is selected from hydrogen, halo, hydroxy, amino, carboxy, cyano, nitro, thio, optionally substituted ($C_1$-$C_6$) alkyl, hydroxy($C_1$-$C_6$)alkyl, optionally substituted ($C_1$-$C_6$) alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy ($C_1$-$C_6$)alkyl, ($C_1$-$C_6$)alkyloxycarbonyl, ($C_1$-$C_6$)alkylcarbonyloxy, optionally substituted aminocarbonyl, and aminocarbonyl($C_1$-$C_6$)alkyl;

wherein the method comprises contacting the ketone substrate compound of Formula (IIb).

(IIb)

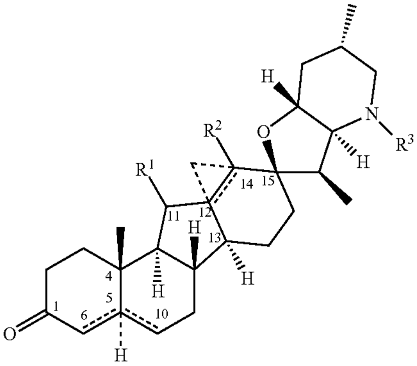

wherein rings A, B, C, and D, and $R^1$, $R^2$, and $R^3$ are as defined above for the compound of Formula (Ib), with an engineered transaminase polypeptide of the present disclosure in the presence of an amino donor under suitable reaction conditions.

In some embodiments, the engineered transaminase polypeptides can be used to prepare any of the cyclopamine analog compounds disclosed in WO 2011017551A1, published Feb. 10, 2011, which is hereby incorporated by reference herein.

Numerous other cyclopamine analog compounds (other than those encompassed by Formulas (Ia) and (Ib)) are known in the art. In some embodiments, it is contemplated that the engineered transaminase polypeptides of the present disclosure can be used in biocatalytic processes to prepare any of the known veratramine analog compounds.

In some embodiments, the engineered transaminase polypeptides of the disclosure are capable of converting veratramine analog compounds of Formula (IIc), wherein Ring C is 5-membered carbocyclic ring and Ring D is a 6-membered carbocyclic ring, to the chiral amine product compound of Formula (Ic) as shown in Scheme 7:

Scheme 7

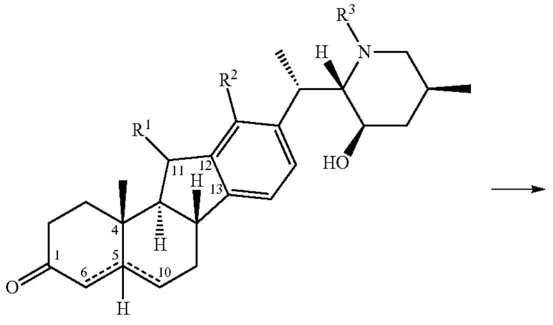

(IIc)

-continued

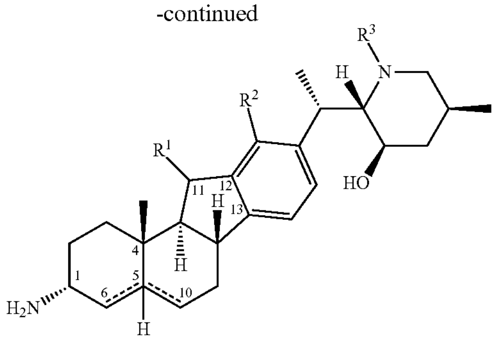

(Ic)

Accordingly, in some embodiments, the present disclosure provides a process for preparation of an amine compound of Formula (Ic)

(Ic)

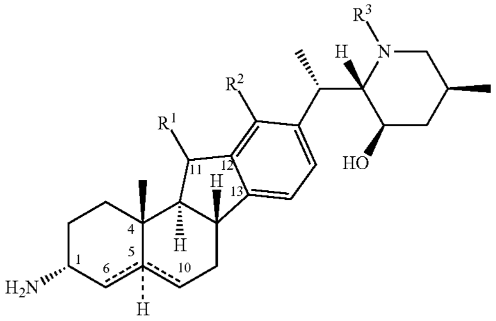

wherein

Rings A and B comprise one of the following:

(a) an unsaturated C—C bond between positions 5 and 6:

(b) an unsaturated C—C bond between positions 5 and 10;

(c) a hydrogen at position 5 cis to the methyl group at position 4; or (d) a hydrogen at position 5 trans to the methyl group at position 4;

Ring D is aromatic;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched ($C_1$-$C_4$)alkyl, straight-chain or branched ($C_1$-$C_4$)alkenyl, and straight-chain or branched ($C_1$-$C_3$)alkylamino; and $R^3$ is selected from hydrogen, halo, hydroxy, amino, carboxy, cyano, nitro, thio, optionally substituted ($C_1$-$C_6$) alkyl, hydroxy($C_1$-$C_6$)alkyl, optionally substituted ($C_1$-$C_6$) alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy ($C_1$-$C_6$)alkyl, ($C_1$-$C_6$)alkyloxycarbonyl, ($C_1$-$C_6$)alkylcarbonyloxy, optionally substituted aminocarbonyl, and aminocarbonyl($C_1$-$C_6$)alkyl;

wherein the method comprises contacting the ketone substrate compound of Formula (IIc).

(IIc)

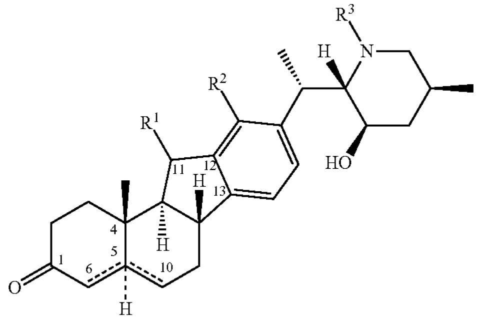

wherein rings A, B, C, and D, and $R^1$, $R^2$, and $R^3$ are as defined above for the compound of Formula (Ic), with an engineered transaminase polypeptide of the present disclosure in the presence of an amino donor under suitable reaction conditions.

Numerous other veratramine analog compounds (other than those encompassed by Formula (Ic)) are known in the art. In some embodiments, it is contemplated that the engineered transaminase polypeptides of the present disclosure can be used in biocatalytic processes to prepare any of the known veratramine analog compounds.

In some embodiments, the engineered transaminase polypeptides of the disclosure are capable of converting steroid analog compounds of Formula (Hd), wherein Ring C is 6-membered carbocyclic ring and Ring D is a 5-membered carbocyclic ring, to a chiral amine product of Formula (Id) as shown in Scheme 8:

Scheme 8

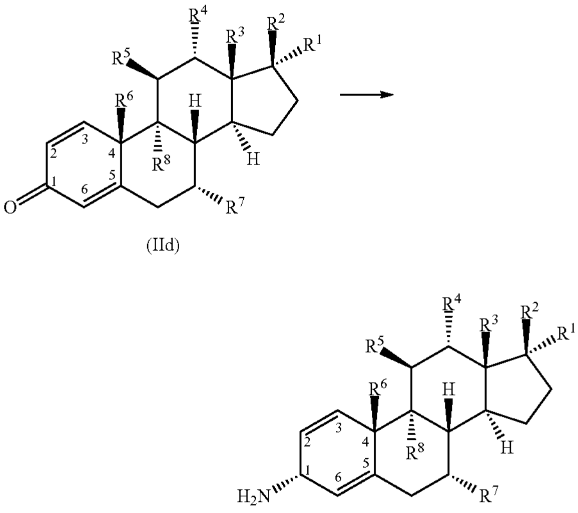

(IId)

(Id)

Accordingly, in some embodiments, the present disclosure provides a process for preparation of an amine compound of Formula (Id)

(Id)

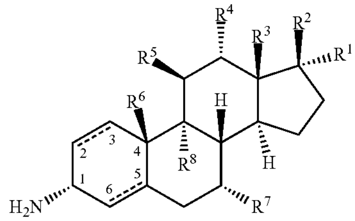

wherein

Ring A comprises an unsaturated C—C bond between positions 2 and 3, or positions 5 and 6;

$R^1$ and $R^2$ are selected independently from hydrogen, halo, hydroxy, amino, carboxy, cyano, nitro, thio, optionally substituted ($C_1$-$C_6$)alkyl, hydroxy($C_1$-$C_6$)alkyl, optionally substituted ($C_1$-$C_6$)alkyloxy, optionally substituted ($C_1$-$C_6$) alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$) alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted arylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl;

$R^3$, $R^4$, and $R^5$ are selected independently from hydrogen, halo, hydroxy, amino, carboxy, cyano, nitro, thio, straight-chain or branched ($C_1$-$C_4$)alkyl, straight-chain or branched ($C_1$-$C_4$)alkenyl, and straight-chain or branched ($C_1$-$C_3$)alkylamino; and $R^6$, $R^7$, and $R^8$ are selected independently from hydrogen, halo, hydroxy, and methyl;

wherein the method comprises contacting the ketone substrate compound of Formula (IId), (IId)

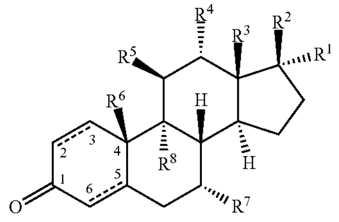

wherein $R^1$, $R^2$, $R^3$, $R^4$, $R^5$, $R^6$, $R^7$, and $R^8$ are as defined above for the compound of Formula (Id), with an engineered transaminase polypeptide of the present disclosure in the presence of an amino donor under suitable reaction conditions.

In some embodiments of the process for preparing an amine compound of Formula (Id), the process can be carried out using a ketone substrate compound of Formula (IId) selected from those shown in Table 3.

TABLE 3
| Ketone substrate compound of Formula (IId) | Chiral amine product compound of Formula (Id) |
| --- | --- |
| 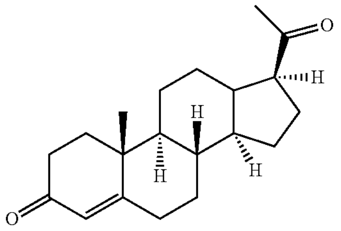 | 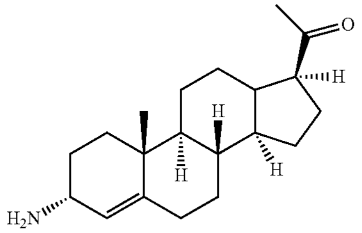 |
| 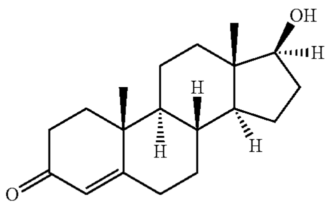 | 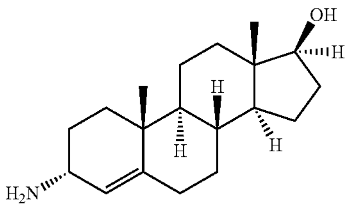 |
| 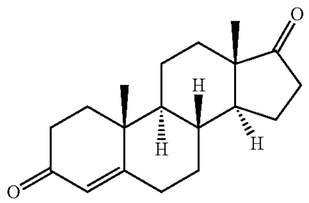 | 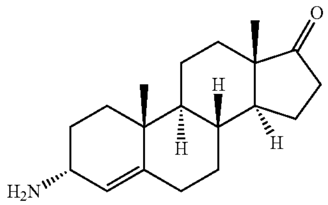 |
| 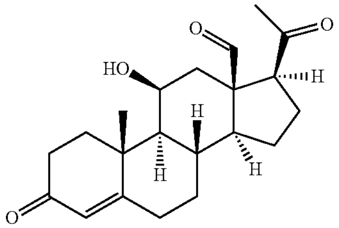 | 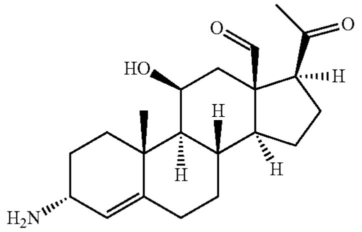 |
| 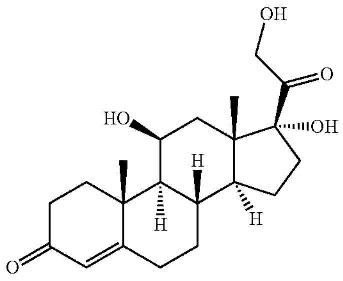 | 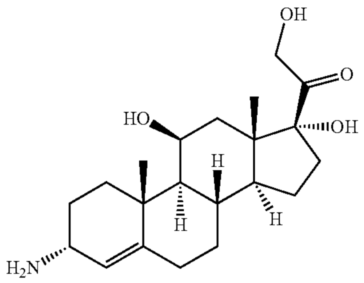 |
| 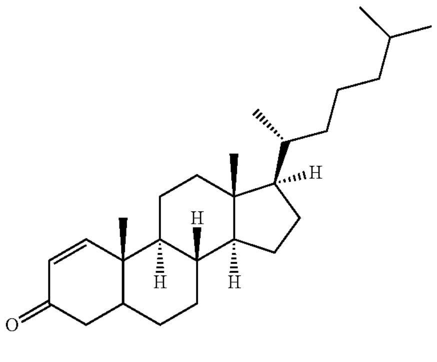 | 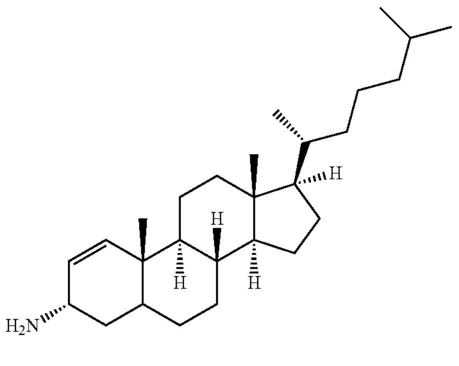 |

TABLE 3-continued

| Ketone substrate compound of Formula (IId) | Chiral amine product compound of Formula (Id) |
| --- | --- |
| 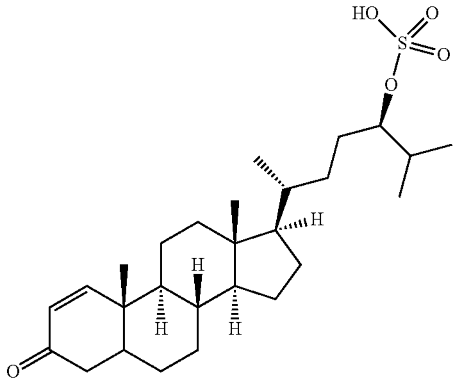 | 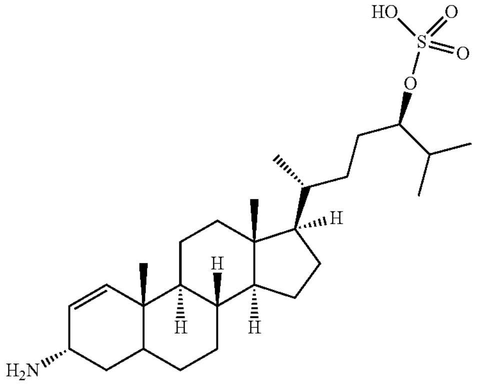 |
| 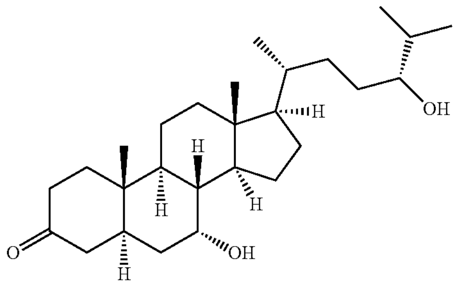 | 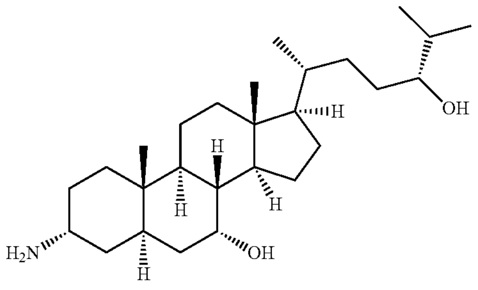 |
| 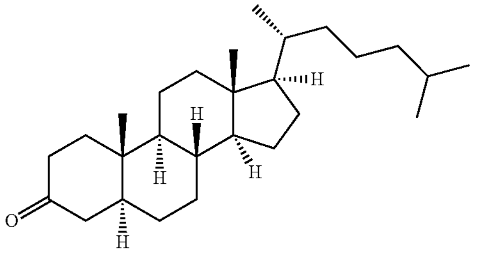 | 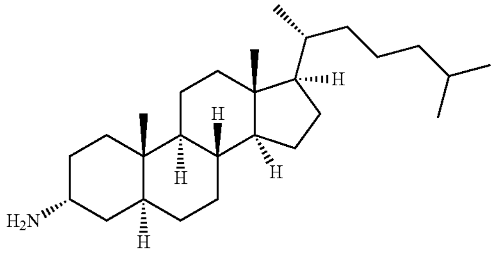 |
| 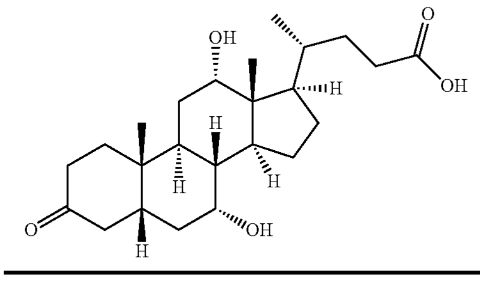 | 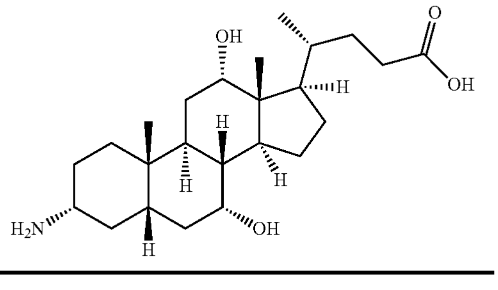 |

In addition to the compounds of Formula (IId), including those shown in Table 3, there are a multitude of steroid analog compounds known in the art. The present disclosure contemplates that any steroid analog compound with a ketone group at position 1 of Ring A could be used as ketone substrates with an engineered transaminase polypeptides of the present disclosure in a process to prepare its corresponding steroid analog compound with a chiral amine group at position 1.

In view of the stereoselectivity of the engineered transaminase polypeptides of the present disclosure, in some embodiments the process results in the formation of the chiral amine compounds of Formula (I), Formula (Ia), Formula (Ib), Formula (Ic), and Formula (Id) in diastereomeric excess.

In some embodiments, the process results in the formation of the chiral amine compound of Formula (I), Formula (Ia), Formula (Ib), Formula (Ic), and Formula (Id) in diastereomeric excess of at least 90%, 95%, 96%, 97%, 98%, 99%, or greater.

For the foregoing processes, any of the engineered transaminase polypeptides described herein can be used. By way of example and without limitation, in some embodiments, the process can use an engineered polypeptide having transaminase activity of the present disclosure comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204, and one or more residue differences as compared to SEQ ID NO:2 at residue positions selected from X19, X21, X34, X53, X56, X73, X86, X88, X107, X113, X133, X147, X155, X165, X171, X178, X233, X251, X259, X268, X277, X286, X312, X316, X317, X323, X358, X366, X383, X399, X414, X415, X417, X426, X434, and X450, wherein the residue differences at residue positions X21, X56, X86, X88, X107, X113, X133, X147, X233, X286, X312, X316, X323, X383, X415, X417, and X434, are selected from: X21H, X56A/C, X86C, X88H/Y, X107G, X113L/P, X133A, X147H/V, X233V, X286C/H, X312N, X316C/F/G/N/S/T, X323A, X383C/F/I/M/T, X415A/G/H/L/V, X417V, and X434T. In some embodiments, the specific amino acid differences at positions X19, X34, X53, X73, X155, X165, X171, X178, X251, X259, X268, X277, X317, X358, X366, X399, X414, X426, and X450 are selected from: X19W, X34A, X53M, X73R, X155V, X165F, X171Q, X178W, X251V, X259V, X268A, X277A, X317L, X358K, X366H, X399A, X414I, X426R, and X450S. In some embodiments, the reference sequence is selected from SEQ ID NO: 4, 8, 26, 36, 40, 78, 100, 102, 148, 156, 160, 170, 172, 180, and 198. In some embodiments, the reference sequence is SEQ ID NO:4. In some embodiments, the reference sequence is SEQ ID NO:100. In some embodiments, the reference sequence is SEQ ID NO:148. In some embodiments, the reference sequence is SEQ ID NO: 156. In some embodiments, the reference sequence is SEQ ID NO: 160. In some embodiments, the reference sequence is SEQ ID NO: 180.

In some embodiments, exemplary transaminase polypeptides capable of carrying out the processes herein can be a polypeptide comprising an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 154, 156, 158, 160, 162, 164, 166, 168, 170, 172, 174, 176, 178, 180, 182, 184, 186, 188, 190, 192, 194, 196, 198, 200, 202, and 204. Guidance on the choice and use of the engineered transaminase polypeptides is provided in the descriptions herein, for example Tables 2A and 2B and the Examples.

In the embodiments herein and illustrated in the Examples, various ranges of suitable reaction conditions that can be used, including but not limited, to ranges of amino donor, pH, temperature, buffer, solvent system, substrate loading, polypeptide loading, cofactor loading, pressure, and reaction time. Further suitable reaction conditions for carrying out the process for biocatalytic conversion of substrate compounds to product compounds using an engineered transaminase polypeptide described herein can be readily optimized in view of the guidance provided herein by routine experimentation that includes, but is not limited to, contacting the engineered transaminase polypeptide and substrate compound under experimental reaction conditions of concentration, pH, temperature, solvent conditions, and detecting the product compound.

In some embodiments herein, the transaminase polypeptide uses an amino donor to form the product compounds. In some embodiments, the amino donor in the reaction condition can be selected from isopropylamine (also referred to herein as "IPM"), putrescine, L-lysine, α-phenethylamine, D-alanine, L-alanine, or D,L-alanine, or D,L-ornithine. In some embodiments, the amino donor is selected from IPM, putrescine, L-lysine, D- or L-alanine. In some embodiments, the amino donor is IPM. In some embodiments, the suitable reaction conditions comprise the amino donor, in particular IPM, present at a concentration of at least about 0.1 to about 3 M, 0.2 to about 2.5 M, about 0.5 to about 2 M or about 1 to about 2 M. In some embodiments, the amino donor is present at a concentration of about 0.1, 0.2, 0.3, 0.4, 0.5, 0.6, 0.7, 0.8, 1, 1.5, 2, 2.5 or 3 M. Higher concentrations of amino donor, e.g., IPM, can be used to shift the equilibrium towards amine product formation.

Suitable reaction conditions using the engineered transaminase polypeptides also typically comprise a cofactor. Cofactors useful for transaminase enzymes herein include, but are not limited to, pyridoxal-5'-phosphate (also known as pyridoxal-phosphate, PLP, P5P), pyridoxine (PN), pyridoxal (PL), pyridoxamine (PM), and their phosphorylated counterparts pyridoxine phosphate (PNP) and pyridoxamine phosphate (PMP). In some embodiments, the cofactor PLP is present naturally in the cell extract and does not need to be supplemented. In some embodiments of the processes, the suitable reaction conditions comprise exogenous cofactor added to the enzyme reaction mixture, for example, when using partially purified or purified transaminase enzyme. In some embodiments, the suitable reaction conditions can comprise the presence of a cofactor selected from PLP, PN, PL, PM, PNP, and PMP, at a concentration of about 0.1 g/L to about 10 g/L, about 0.2 g/L to about 5 g/L, about 0.5 g/L to about 2.5 g/L. In some embodiments, the reaction conditions comprise a PLP concentration of about 0.1 g/L or less, 0.2 g/L or less, 0.5 g/L or less, 1 g/L or less, 2.5 g/L or less, 5 g/L or less, or 10 g/L or less. In some embodiments, the cofactor can be added either at the beginning of the reaction and/or additional cofactor is added during the reaction.

Substrate compound in the reaction mixtures can be varied, taking into consideration, for example, the desired amount of product compound, the effect of substrate concentration on enzyme activity, stability of enzyme under reaction conditions, and the percent conversion of substrate to product. In some embodiments, the suitable reaction conditions comprise a substrate compound loading of at least about 0.5 to about 200 g/L, 1 to about 200 g/L, about 5 to about 150 g/L, about 10 to about 100 g/L, about 20 to about 100 g/L, or about 50 to about 100 g/L. In some embodiments, the suitable reaction conditions comprise a substrate compound loading of at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L, at least about 150 g/L or at least about 200 g/L, or even greater. The values for substrate loadings provided herein are based on the molecular weight of compound (2), however it also contemplated that the equivalent molar amounts of various hydrates and salts of compound (2) also can be used in the process. In addition, ketone substrate compounds of Formula (II), including compounds of Formula (IIa), (IIb), (IIc), and (IId) can also be used in appropriate amounts, in light of the amounts used for compound (2).

In carrying out the reactions described herein, the engineered transaminase polypeptide may be added to the reaction mixture in the form of a purified enzyme, whole cells transformed with gene(s) encoding the enzyme, and/or as cell extracts and/or lysates of such cells. Whole cells transformed with gene(s) encoding the engineered transaminase enzyme or cell extracts, lysates thereof, and isolated enzymes may be employed in a variety of different forms, including solid (e.g., lyophilized, spray-dried, and the like) or semisolid (e.g., a crude paste). The cell extracts or cell lysates may be partially purified by precipitation (ammonium sulfate, polyethyleneimine, heat treatment or the like), followed by a desalting procedure prior to lyophilization (e.g., ultrafiltration, dialysis, and the like). Any of the cell preparations may be stabilized by crosslinking using known crosslinking agents, such as, for example, glutaraldehyde, or immobilization to a solid phase (e.g., Eupergit C, and the like).

The gene(s) encoding the engineered transaminase polypeptides can be transformed into host cell separately or together into the same host cell. For example, in some embodiments one set of host cells can be transformed with gene(s) encoding one engineered transaminase polypeptide and another set can be transformed with gene(s) encoding another engineered transaminase polypeptide. Both sets of transformed cells can be utilized together in the reaction mixture in the form of whole cells, or in the form of lysates or extracts derived therefrom. In other embodiments, a host cell can be transformed with gene(s) encoding multiple engineered transaminase polypeptide. In some embodiments the engineered polypeptides can be expressed in the form of secreted polypeptides and the culture medium containing the secreted polypeptides can be used for the transaminase reaction.

The enhancements in activity and/or stereoselectivity of the engineered transaminase polypeptides disclosed herein provide for processes wherein higher percentage conversion can be achieved with lower concentrations of the engineered polypeptide. In some embodiments of the process, the suitable reaction conditions comprise an engineered polypeptide concentration of about 0.01 to about 50 g/L; about 0.05 to about 50 g/L; about 0.1 to about 40 g/L; about 1 to about 40 g/L; about 2 to about 40 g/L; about 5 to about 40 g/L; about 5 to about 30 g/L; about 0.1 to about 10 g/L; about 0.5 to about 10 g/L; about 1 to about 10 g/L; about 0.1 to about 5 g/L; about 0.5 to about 5 g/L; or about 0.1 to about 2 g/L. In some embodiments, the transaminase polypeptide is concentration at about 0.01, 0.05, 0.1, 0.2, 0.5, 1, 2, 5, 10, 15, 20, 25, 30, 35, 40, or 50 g/L.

During the course of the transamination reactions, the pH of the reaction mixture may change. The pH of the reaction mixture may be maintained at a desired pH or within a desired pH range. This may be done by adding an acid or base, before and/or during the course of the reaction. Alternatively, the pH may be controlled by using a buffer. Accordingly, in some embodiments, the reaction condition comprises a buffer. Suitable buffers to maintain desired pH ranges are known in the art and include, by way of example and not limitation, borate, carbonate, phosphate, triethanolamine (TEA), and the like. In some embodiments, the buffer is borate. In some embodiments of the process, the suitable reaction conditions comprise a buffer solution of TEA, where the TEA concentration is from about 0.01 to about 0.4 M, 0.05 to about 0.4 M, 0.1 to about 0.3 M, or about 0.1 to about 0.2 M. In some embodiments, the reaction condition comprises a TEA concentration of about 0.01, 0.02, 0.03, 0.04, 0.05, 0.07, 0.1, 0.12, 0.14, 0.16, 0.18, 0.2, 0.3, or 0.4 M. In some embodiments, the reaction conditions comprise water as a suitable solvent with no buffer present.

In the embodiments of the process, the reaction conditions can comprise a suitable pH. The desired pH or desired pH range can be maintained by use of an acid or base, an appropriate buffer, or a combination of buffering and acid or base addition. The pH of the reaction mixture can be controlled before and/or during the course of the reaction. In some embodiments, the suitable reaction conditions comprise a solution pH from about 6 to about 12, pH from about 6 to about 10, pH from about 6 to about 8, pH from about 7 to about 10, pH from about 7 to about 9, or pH from about 7 to about 8. In some embodiments, the reaction conditions comprise a solution pH of about 6, 6.5, 7, 7.5, 8, 8.5, 9, 9.5, 10, 10.5, 11, 11.5 or 12.

In the embodiments of the processes herein, a suitable temperature can be used for the reaction conditions, for example, taking into consideration the increased reaction rate at higher temperatures, and the activity of the enzyme during the reaction time period. For example, the engineered polypeptides of the present disclosure have increased stability relative to naturally occurring transaminase polypeptide e.g., the wild-type polypeptide of SEQ ID NO: 2, which allow the engineered polypeptides to be used at higher temperatures for increased conversion rates and improved substrate solubility characteristics. Accordingly, in some embodiments, the suitable reaction conditions comprise a temperature of about 10° C. to about 70° C., about 10° C. to about 65° C., about 15° C. to about 60° C., about 20° C. to about 60° C., about 20° C. to about 55° C., about 30° C. to about 55° C., or about 40° C. to about 50° C. In some embodiments, the suitable reaction conditions comprise a temperature of about 10° C., 15° C. 20° C., 25° C., 30° C. 35° C., 40° C., 45° C., 50° C. 55° C., 60° C., 65° C. or 70° C. In some embodiments, the temperature during the enzymatic reaction can be maintained at a temperature throughout the course of the reaction or adjusted over a temperature profile during the course of the reaction.

The processes herein are generally carried out in a solvent. Suitable solvents include water, aqueous buffer solutions, organic solvents, polymeric solvents, and/or co-solvent systems, which generally comprise aqueous solvents, organic solvents and/or polymeric solvents. The aqueous solvent (water or aqueous co-solvent system) may be pH-buffered or unbuffered. In some embodiments, the processes are generally carried out in an aqueous co-solvent system comprising an organic solvent (e.g., ethanol, isopropanol (IPA), dimethyl sulfoxide (DMSO), ethyl acetate, butyl acetate, 1-octanol, heptane, octane, methyl t-butyl ether (MTBE), toluene, and the like), ionic or polar solvents (e.g., 1 ethyl 4 methylimidazolium tetrafluoroborate, 1 butyl 3 methylimidazolium tetrafluoroborate, 1 butyl 3 methylimidazolium hexafluorophosphate, glycerol, polyethylene glycol, and the like). In some embodiments, the co-solvent can be a polar solvent, such as a polyol, dimethylsulfoxide, DMSO, or lower alcohol. The non-aqueous co-solvent component of an aqueous co-solvent system may be miscible with the aqueous component, providing a single liquid phase, or may be partly miscible or immiscible with the aqueous component, providing two liquid phases. Exemplary aqueous co-solvent systems can comprise water and one or more co-solvents selected from an organic solvent, polar solvent, and polyol solvent. In general, the co-solvent component of an aqueous co-solvent system is chosen such that it does not adversely inactivate the transaminase enzyme under the reaction conditions. Appropriate co-solvent systems can be readily identified by measuring the enzymatic activity of the specified engineered transaminase enzyme with a defined substrate of interest in the candidate solvent system, utilizing an enzyme activity assay, such as those described herein.

In some embodiments of the process, the suitable reaction conditions comprise an aqueous co-solvent, where the co-solvent comprises DMSO at about 1% to about 80% (v/v), about 1 to about 70% (v/v), about 2% to about 60% (v/v), about 5% to about 40% (v/v), 10% to about 40% (v/v), 10% to about 30% (v/v), or about 10% to about 20% (v/v). In some embodiments of the process, the suitable reaction conditions comprise an aqueous co-solvent comprising DMSO at least about 1%, 5%, 10%, 15%, 20%, 25%, 30%, 35%, 40%, 45%, 50%, 55%, 60%, 65%, 70%, 75%, or 80% (v/v). In some embodiments of the process, the suitable reaction conditions comprise an aqueous co-solvent comprising DMSO of from about 15% (v/v) to about 45% (v/v), from about 20% (v/v) to about 30% (v/v), and in some embodiments a DMSO concentration of about 25% (v/v).

In some embodiments of the process, the suitable reaction conditions comprise an aqueous co-solvent, where the co-solvent can comprises a polymeric polyol solvent. Examples of suitable polyol solvents include, by way of example and not limitation, polyethylene glycol, polyethylene glycol methyl ether, diethylene glycol dimethyl ether, triethylene glycol dimethyl ether, and polypropylene glycol. In some embodiments, the aqueous co-solvent comprises polyethylene glycol, which is available in different molecular weights. Particularly useful are lower molecular weight polyethylene glycols, such as PEG200 to PEG600. Accordingly, in some embodiments, the aqueous co-solvent can comprise PEG200 of about 1% to about 40% v/v; about 1% to about 40% v/v; about 2% to about 40% v/v; about 5% to about 40% v/v; 2% to about 30% v/v; 5% to about 30% v/v; 1 to about 20% v/v; about 2% to about 20% v/v; about 5% to about 20% v/v; about 1% to about 10% v/v; about 2% to about 10% v/v. In some embodiments, the suitable reaction conditions comprises an aqueous co-solvent comprising PEG200 at about 1%, 2%, 5%, 10%, 15%, 20%; 25%; 30%; 35%; 35% or about 40% v/v.

The quantities of reactants used in the transamination reaction will generally vary depending on the quantities of product desired, and concomitantly the amount of transaminase substrate employed. Those having ordinary skill in the art will readily understand how to vary these quantities to tailor them to the desired level of productivity and scale of production.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, transaminase, and transaminase substrate may be added first to the solvent.

The solid reactants (e.g., enzyme, salts, substrate compounds, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

For improved mixing efficiency when an aqueous co-solvent system is used, the transaminase and cofactor may be added and mixed into the aqueous phase first. The organic phase may then be added and mixed in, followed by addition of the transaminase substrate. Alternatively, the transaminase substrate may be premixed in the organic phase, prior to addition to the aqueous phase.

The transamination reaction is generally allowed to proceed until further conversion of ketone substrate to amine product does not change significantly with reaction time, e.g., less than 10% of substrate being converted, or less than 5% of substrate being converted. In some embodiments, the reaction is allowed to proceed until there is complete or near complete conversion of substrate ketone to product amine. Transformation of substrate to product can be monitored using known methods by detecting substrate and/or product. Suitable methods include gas chromatography, HPLC, and the like. Conversion yields of the chiral amine product generated in the reaction mixture are generally greater than about 50%, may also be greater than about 60%, may also be greater than about 70%, may also be greater than about 80%, may also be greater than 90%, and may be greater than about 97%. In some embodiments, the methods for preparing compounds of Formula (I) using an engineered transaminase polypeptide under suitable reaction conditions results in at least about 91%, 92%, 93%, 94%, 95%, 96%, 97%, 98%, 99% or greater conversion of ketone substrate, e.g, compound of Formula (II), to the amine product compound, e.g., compound of Formula (I) in about 48 h or less, in about 36 h or less, in about 24 h or less, or even less time.

In some embodiments of the process, the suitable reaction conditions comprise a substrate loading of at least about 20 g/L, 30 g/L, 40 g/L, 50 g/L, 60 g/L, 70 g/L, 100 g/L, or more, and wherein the process results in at least about 91%, 92%, 93%, 94%, 95%, 96%, 97%, 98%, 99% or greater conversion of substrate compound to product compound in about 48 h or less, in about 36 h or less, or in about 24 h or less.

The engineered transaminase polypeptides of the present disclosure when used in the process for preparing chiral amine compounds of Formula (I) under suitable reaction conditions result in an diastereomeric excess of the chiral amine in at least 90%, 91%, 92%, 93%, 94%, 95% 97%, 98, 99%, 99.1%, 99.2%, 99.3%, 99.4%, 99.5%, 99.6%, 99.7%, 99.8%, or 99.9% d.e.

In a further embodiment of the processes, the suitable reaction conditions can comprise an initial substrate loading to the reaction solution which is then contacted by the polypeptide. This reaction solution is then further supplemented with additional substrate compound as a continuous addition over time at a rate of at least about 1 g/L/h, at least about 2 g/L/h, at least about 4 g/L/h, at least about 6 g/L/h, or higher. Thus, according to these suitable reaction conditions, polypeptide is added to a solution having an initial substrate loading of at least about 20 g/L, 30 g/L, or 40 g/L. This addition of polypeptide is then followed by continuous addition of further substrate to the solution at a rate of about 2 g/L/h, 4 g/L/h, or 6 g/L/h until a much higher final substrate loading of at least about 30 g/L, 40 g/L, 50 g/L, 60 g/L, 70 g/L, 100 g/L, 150 g/L, 200 g/L or more, is reached. Accordingly, in some embodiments of the process, the suitable reaction conditions comprise addition of the polypeptide to a solution having an initial substrate loading of at least about 20 g/L, 30 g/L, or 40 g/L followed by addition of further substrate to the solution at a rate of about 2 g/L/h, 4 g/L/h, or 6 g/L/h until a final substrate loading of at least about 30 g/L, 40 g/L, 50 g/L, 60 g/L, 70 g/L, 100 g/L or more, is reached. This substrate supplementation reaction condition allows for higher substrate loadings to be achieved while maintaining high rates of conversion of ketone substrate to amine product of at least about 91%, 92%, 93%, 94%, 95%, 96%, 97%, 98%, 99% or greater. In some embodiments of this process, the further substrate added is in a solution comprising isopropylamine or isopropylamine acetate at a concentration of at least about 0.5 M, at least about 1.0 M, at least about 2.5 M, at least about 5.0 M, at least about 7.5 M, at least about 10.0 M.

In some embodiments of the processes, the transamination reaction can comprise the following suitable reaction conditions: (a) substrate loading at about 5 g/L to 200 g/L; (b) about 0.1 to 50 g/L of engineered transaminase polypeptide; (c) about 0.1 to 4 M of isopropylamine (IPM); (d) about 0.1 to 10 g/L of pyridoxal phosphate (PLP) cofactor; (e) pH of about 6 to 9; and (f) temperature of about 30 to 60° C.

In some embodiments of the processes, the transamination reaction can comprise the following suitable reaction conditions: (a) substrate loading at about 10 g/L to 150 g/L; (b) about 0.5 to 20 g/L of engineered transaminase polypeptide; (c) about 0.1 to 3 M of isopropylamine (IPM); (d) about 0.1 to 10 g/L of pyridoxal phosphate (PLP) cofactor; (e) about 0.05 to 0.20 M TEA buffer; (f) about 1% to about 45% DMSO; (g) pH of about 6 to 9; and (h) temperature of about 30 to 65° C.

In some embodiments of the processes, the transamination reaction can comprise the following suitable reaction conditions: (a) substrate loading at about 20 to 100 g/L; (b) about 1 to 5 g/L of engineered transaminase polypeptide; (c) about 0.5 to 2 M of isopropylamine (IPM); (d) about 0.2 to 2 g/L of pyridoxal phosphate (PLP) cofactor; (e) about 0.1 M TEA buffer; (f) about 25% DMSO; (e) pH of about 8; and (f) temperature of about 45 to 60° C.

In some embodiments, additional reaction components or additional techniques carried out to supplement the reaction conditions. These can include taking measures to stabilize or prevent inactivation of the enzyme, reduce product inhibition, and/or shift reaction equilibrium to product amine formation.

Accordingly, in some embodiments of the process for preparing an amine, such as a chiral amine, additional quantities of the amino acceptor can be added (up to saturation) and/or the amino acceptor (ketone) formed can be continuously removed from the reaction mixture. For example, a solvent bridge or a two phase co-solvent system can be used to move the amine product to an extraction solution, and thereby reduce inhibition by amine product and also shift the equilibrium towards product formation (see, e.g., Yun and Kim, 2008, Biosci. Biotechnol. Biochem. 72(11):3030-3033).

In some embodiments of the processes, the suitable reaction conditions comprise the presence of the reduced cofactor, nicotinamide adenine dinucleotide (NADH), which can act to limit the inactivation of the transaminase enzyme (see e.g., van Ophem et al., 1998, Biochemistry 37(9):2879-88). In such embodiments where NADH is present, a cofactor regeneration system, such as glucose dehydrogenase (GDH) and glucose or formate dehydrogenase and formate can be used to regenerate the NADH in the reaction medium.

In some embodiments, the process can further comprise removal of the carbonyl by-product formed from the amino group donor when the amino group is transferred to the amino group acceptor. Such removal in situ can reduce the rate of the reverse reaction such that the forward reaction dominates and more substrate is then converted to product. Removal of the carbonyl by-product can be done in a number of ways. Where the amino group donor is an amino acid, such as alanine, the carbonyl by-product, a keto acid, can be removed by reaction with a peroxide (see, e.g., US 2008/0213845, incorporated herein by reference). Peroxides that can be used include, among others, hydrogen peroxide; peroxyacids (peracids), such as peracetic acid ($CH_3CO_3H$), trifluoroperacetic acid and metachloroperoxybenzoic acid; organic peroxides such as t-butyl peroxide ($(CH_3)_3COOH$); or other selective oxidants such as tetrapropylammonium perruthenate, $MnO_2$, $KMnO_4$, ruthenium tetroxide and related compounds. Alternatively, pyruvate removal can be achieved via its reduction to lactate by employing lactate dehydrogenase to shift equilibrium to the product amine (see, e.g., Koszelewski et al., 2008, Adv. Syn. Catal. 350: 2761-2766). Pyruvate removal can also be achieved via its decarboxylation by employing pyruvate decarboxylase (see, e.g., Höhne et al., 2008, Chem BioChem 9:363-365) or acetolactate synthase (see, e.g., Yun and Kim, supra).

Alternatively, in embodiments where an amino acid is used as amino group donor, the keto acid carbonyl by-product can be recycled back to the amino acid by reaction with ammonia and NADH using an appropriate dehydrogenase enzyme, e.g., amino acid dehydrogenase, in presence of an amine donor, such as ammonia, thereby replenishing the amino group donor.

In some embodiments, where the choice of the amino donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas. In some embodiments, the amino donor used in the process is isopropylamine (IPM), which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap. Alternatively, the acetone can be removed by reduction to isopropanol using a transaminase.

In some embodiments of the processes above where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is isopropylamine and the acetone product is removed in situ, isopropylamine can be added to the solution to replenish the amino group donor lost during the acetone removal and to maintain the pH of the reaction.

In further embodiments, any of the above described process for the conversion of substrate compound to product compound can also comprise one or more steps selected from: extraction, isolation, purification, and crystallization of product compound. Methods, techniques, and protocols for extracting, isolating, purifying, and/or crystallizing the product amine from biocatalytic reaction mixtures produced by the above disclosed methods are known to the ordinary artisan and/or accessed through routine experimentation. Additionally, illustrative methods are provided in the Examples below.

Various features and embodiments of the disclosure are illustrated in the following representative examples, which are intended to be illustrative, and not limiting.

6. EXAMPLES

Example 1: Synthesis, Optimization, and Screening Engineered Transaminase Polypeptides Gene Synthesis and Optimization:

The polynucleotide sequence encoding the 453 amino acid wild-type ω-transaminase polypeptide from *Vibrio fluvialis* JS17 (Genbank Acc. No. AEA39183.1, GI: 327207066) previously was codon optimized and synthesized. The sequence of this codon-optimized *V. fluvialis* wild-type transaminase gene was disclosed as SEQ ID NO: 1 in WO2011159910A2, published Dec. 22, 2011, which is hereby incorporated by reference herein. This codon-optimized gene was cloned into a pCK110900 vector system (see e.g., US Patent Application Publication 20060195947, which is hereby incorporated by reference herein) and subsequently expressed in *E. coli* W3110fhuA. The *E. coli* W3110 expresses the transaminase polypeptides as an intracellular protein under the control of the lac promoter. The polynucleotide of the present disclosure with sequence of SEQ ID NO: 1 encodes an engineered transaminase polypeptide of SEQ ID NO: 2 and was obtained by directed evolution of the codon-optimized *V. fluvialis* wild-type transaminase gene of WO2011159910A2. The engineered transaminase polypeptide of SEQ ID NO:2 has 10 amino acid residue differences (A9T; N45H; W57L; F86S; V153A; V177L; R211K; M294V; S324G; and T391A) as compared to the wild-type *V. fluvialis* transaminase polypeptide sequence of Genbank Acc. No. AEA39183.1, GI: 327207066. The polynucleotide of the present disclosure with sequence of SEQ ID NO: 1 (encoding the engineered polypeptide of SEQ ID NO: 2), was further optimized to provide SEQ ID NO: 3 which encodes the engineered transaminase polypeptide of SEQ ID NO: 4. The engineered transaminase polypeptide of SEQ ID NO: 4 has the following 8 amino acid residue differences as compared to SEQ ID NO: 2: T34A; L56A; R88H; A153C; A155V; K163F; E315G; and L417T. The polynucleotide of the present disclosure with sequence of SEQ ID NO: 3 (encoding the engineered transaminase polypeptide of SEQ ID NO: 4), was used as the starting backbone for further optimization using standard methods of directed evolution via iterative variant library generation by gene synthesis followed by screening and sequencing of the hits to generate genes encoding engineered transaminases capable of converting compound (2) to compound (1) with enhanced enzyme properties relative to the polypeptides SEQ ID NO: 4. The resulting engineered transaminase polypeptide sequences and specific mutations and relative activities are listed in Tables 2A and the Sequence Listing.

Example 2: Production of Engineered Transaminases

The engineered transaminase polypeptides were produced in host *E. coli*. W3110 as an intracellular protein expressed under the control of the lac promoter. The polypeptide accumulates primarily as a soluble cytosolic active enzyme. A shake-flask procedure is used to generate engineered polypeptide powders that can be used in activity assays or biocatalytic processes disclosed herein.

High-Throughput Growth and Expression.

Cells are picked and grown overnight in LB media containing 1% glucose and 30 μg/mL chloramphenicol (CAM) under culture conditions of 30° C., 200 rpm, and 85% humidity. A 20 L aliquot of overnight growth are transferred to a deep well plate containing 380 μL 2×YT growth media containing 30 μg/mL CAM, 1 mM IPTG, and incubated for ~18 h at 30° C., 200 rpm, and 85% humidity. Subculture TB media is made up of TB media (380 μL/well), 30 μg/mL CAM, and 1 mM IPTG. Cell cultures are centrifuged at 4000 rpm, 4° C. for 10 minutes, and the media discarded. Cell pellets are resuspended in 250 or 400 μL Lysis Buffer (0.1 M triethanolamine (TEA) buffer, pH 9.0, containing 400 μg/mL PMBS and 500 μg/mL Lysozyme) and the lysate is used in the HTP assay as described below.

Production of Shake Flask Powders (SFP).

A shake-flask procedure was used to generate engineered transaminase polypeptide powders used in secondary screening assays or in the biocatalytic processes disclosed herein. Shake flask powder (SFP) includes approximately 30% total protein and accordingly provide a more purified preparation of an engineered enzyme as compared to the cell lysate used in HTP assays. A single colony of *E. coli* containing a plasmid encoding an engineered transaminase of interest is inoculated into 50 mL Luria Bertani broth containing 30 μg/ml chloramphenicol and 1% glucose. Cells are grown overnight (at least 16 hours) in an incubator at 30° C. with shaking at 250 rpm. The culture is diluted into 250 mL Terrific Broth (12 g/L bacto-tryptone, 24 g/L yeast extract, 4 mL/L glycerol, 65 mM potassium phosphate, pH 7.0, 1 mM $MgSO_4$) containing 30 μg/ml chloramphenicol, in a 1 liter flask to an optical density of 600 nm ($OD_{600}$)) of 0.2 and allowed to grow at 30° C. Expression of the transaminase gene is induced by addition of isopropyl-β-D-thiogalactoside ("IPTG") to a final concentration of 1 mM when the $OD_{600}$ of the culture is 0.6 to 0.8. Incubation is then continued overnight (at least 16 hours). Cells are harvested by centrifugation (5000 rpm, 15 min, 4° C.) and the supernatant discarded. The cell pellet is resuspended with an equal volume of cold (4° C.) 100 mM triethanolamine (chloride) buffer, pH 7.0, and harvested by centrifugation as above. The washed cells are resuspended in two volumes of the cold triethanolamine (chloride) buffer and passed through a French Press twice at 12,000 psi while maintained at 4° C. Cell debris is removed by centrifugation (9000 rpm, 45 minutes, 4° C.). The clear lysate supernatant is collected and stored at −20° C. Lyophilization of frozen clear lysate provides a dry shake-flask powder of crude transaminase polypeptide. Alternatively, the cell pellet (before or after washing) can be stored at 4° C. or −80° C.

Production of Downstream Process (DSP) Powders:

DSP powders contain approximately 80% total protein and accordingly provide a more purified preparation of the engineered transaminase enzyme as compared to the cell lysate used in the high throughput assay. Larger-scale (~100-120 g) fermentation of the engineered transaminase for production of DSP powders can be carried out as a short batch followed by a fed batch process according to standard bioprocess methods. Briefly, transaminase expression is induced by addition of IPTG to a final concentration of 1 mM. Following fermentation, the cells are harvested and resuspended in 100 mM Triethanolamine-$H_2SO_4$ buffer, then mechanically disrupted by homogenization. The cell debris and nucleic acid are flocculated with polyethylenimine (PEI) and the suspension clarified by centrifugation. The resulting clear supernatant is concentrated using a tangential cross-flow ultrafiltration membrane to remove salts and water. The concentrated and partially purified enzyme concentrate can then be dried in a lyophilizer and packaged (e.g., in polyethylene containers).

Example 3: High Throughput (HTP) Screening of Transaminases for Conversion of Large Ketone Substrate Compounds of Formula (II) to Chiral Amine Compounds of Formula (I)

HTP screening of cell lysates was used to guide primary selection of engineered transaminase polypeptides having improved properties for the conversion of large ketone substrates (e.g., compound (2)) to chiral amine products (e.g., compound (1)).

For preparing the lysates, cells were grown in 96-well plates as described above and lysates prepared by dispensing 200 μL (HTP assay for SEQ ID NOs: 4-144) or 250 μL (HTP assay for SEQ ID NOs: 146-204) of Lysis Buffer (1 mg/mL lysozyme, 0.5 mg/mL polymyxin B sulfate, 1 mM PLP, 0.1 M triethanolamine (TEA), pH 7.0) into each well. Plates were sealed, shaken for 2 h, and then centrifuged for 10 min at 4.000 rpm, 4° C. to pellet the cell debris.

HTP Assay for Activity of Polypeptides of SEQ ID NOs:4-144:

A 50 μL aliquot of a stock substrate solution (80 g/L compound (2) dissolved in DMSO) was added to each well of a 96-well plate along with 60 μL of a pre-mixed stock solution of isopropylamine (IPM)/pyridoxal phosphate (PLP) (3.33 M IPM and 1.67 g/L PLP in 100 mM TEA, pH 9), and 35 μL of 0.1 M TEA buffer at pH 9.0. Reactions were initiated by adding 55 μL of cell lysate/well. Plates were sealed and incubated with shaking at 60° C. for 24 h. After 24 h, plates were centrifuged for 3 min at 4000 rpm at 18° C. Reactions were quenched with 400 μL of acetonitrile and samples examined by HPLC as described in Example 4.

HTP Assay for Activity of Polypeptides of SEQ ID NOs:146-204:

A 50 μL aliquot of a stock substrate solution (80 g/L compound (2) dissolved in DMSO) was added to each well of a 96-well plate along with 60 μL of a pre-mixed stock solution of isopropylamine (IPM)/pyridoxal phosphate (PLP) (3.33 M IPM and 1.67 g/L PLP in 100 mM TEA, pH 9), and 60 μL of 0.1 M TEA buffer at pH 9.0. Reactions were initiated by adding 30 μL of cell lysate/well. Plates were sealed and incubated with shaking at 60° C. for 24 h. After 24 h, plates were centrifuged for 3 min at 4000 rpm at 18° C. Reactions were quenched with 400 μL of acetonitrile. Plates were further shaken for 5 min at room temperature and then further centrifuged for 15 min at 4000 rpm at 18° C. to pellet all debris. Samples were examined by HPLC as described in Example 4.

HTP Assay for % de of Compound (1) Produced by Polypeptides of SEQ ID NOs: 146-204:

A 50 μL aliquot of a stock substrate solution (40 g/L compound (2) dissolved in DMSO) was added to each well of a 96-well plate along with 60 μL of a pre-mixed stock solution of isopropylamine (IPM)/pyridoxal phosphate (PLP) (3.33 M IPM and 1.67 g/L PLP in 100 mM TEA, pH 9). Reactions were initiated by adding 90 μL of cell lysate/well. Plates were sealed and incubated with shaking at 250 rpm at 60° C. for 48 h. After 48 h, plates were centrifuged for 3 min at 4000 rpm at 18° C. Reactions were quenched with 400 μL of acetonitrile. Plates were further shaken for 5 min at room temperature to ensure all substrates and products were dissolved. Plates were centrifuged for 15 min at 4000 rpm at 18° C. to pellet all debris. Samples were examined by HPLC as described in Example 4.

Example 4: Analytical Procedures

HPLC Analysis of Activity of HTP Reactions:

Samples for HPLC analysis of activity were prepared by taking a 20 μL aliquot of the quenched HTP reaction as in Example 3 and adding to 180 μL of a diluent solution containing 1:1 acetonitrile:water and 0.37% (v/v) concentrate HCl. The samples were subject to HPLC analysis under the following conditions.

| | | |
|---|---|---|
| Column | Water Symmetry C18, 5 μm, 4.6 × 100 mm with guard column | |
| Temperature | 25° C. | |
| Mobile Phase | Gradient. A: Acetonitrile/0.05% TFA; B: Water/0.05% TFA | |
| Time (min) | A % | B % |
| 0 | 20 | 80 |
| 1.3 | 55 | 45 |
| 2.35 | 55 | 45 |
| 2.60 | 20 | 80 |
| 2.70 | 20 | 80 |
| | Post-run = 0.3 min; Total Run time = 3.0 min | |
| Flow Rate | 2.0 mL/min | |
| Detection | 210 nm | |
| Injection volume | 10 μL | |
| Retention Times | S-amine product: 1.33 min<br>R-amine product (compound (1)): 1.52 min;<br>Ketone substrate (compound (2)): 2.16 min | |

Conversion of compound (2) to compound (1) was determined from the resulting chromatograms as follows:

Conversion (%)=Product Area/(Product Area+Substrate Area)×100%

HPLC Analysis for Product Chiral Purity (% de):

Samples for HPLC analysis of chiral purity or diastereomeric excess of compound (1) were prepared by taking a 40 μL aliquot of the quenched HTP reaction as in Example 3 and adding to 160 μL of a diluent solution containing 1:1 acetonitrile:water and 0.84% (v/v) concentrate HCl. The samples were subject to HPLC analysis under the following conditions.

| | | |
|---|---|---|
| Column | Water Symmetry C18, 5 μm, 4.6 × 100 mm with guard column | |
| Temperature | 25° C. | |
| Mobile Phase | Gradient. A: Acetonitrile/0.05% TFA; B: Water/0.05% TFA | |
| Time (min) | A % | B % |
| 0 | 20 | 80 |
| 0.20 | 20 | 80 |
| 2.10 | 55 | 45 |
| 4.00 | 55 | 45 |
| 4.30 | 20 | 80 |
| 5.50 | 20 | 80 |
| | Post-run = 0.5 min; Total Run time = 6.0 min | |
| Flow Rate | 1.3 mL/min | |
| Detection | 210 nm; reference = 360 nm | |
| Injection volume | 10 μL | |
| Retention Times | S-amine product: 2.17 min<br>R-amine product (compound (1)): 2.44 min;<br>Ketone substrate (compound (2)): 3.37 min | |

Example 5: Process for Conversion of Large Ketone Substrate Compounds of Formula (II) to Chiral Amine Compounds of Formula (I) at 10 mL Scale SFP preparations of the engineered transaminase polypeptides of SEQ ID NO: 4, 8, 26, 36, 40, 78, 100, 102, 148, 156, 160, 170, 172, 180, and 198 were used in 10 mL scale reactions of the conversion of a large ketone substrate of compound (2) to chiral amine compound (1). These reactions demonstrate how these biocatalysts can be used for the preparation of compounds of Formula (I). The reactions at 10 mL scale were carried out as follows. To a 20 mL glass vial equipped with a cross-shaped magnetic stirring bar was added 4 mL of 100 mM TEA buffer (pH 8.0). 2 mL of 5 M IPM.HCl stock solution was added to the vial followed by 1 mL of 5 mM PLP stock solution. The pH of the solution ~8.0. The mixture was stirred at 500 rpm (magnetic stirring). 200 mg of ketone substrate of compound (2) was dissolved in 2.5 mL of DMSO and then added to the vial. The pH of the mixture was adjusted to 8.0 using 1.0 M NaOH solution. Finally, a 0.5 mL aliquot of 40 g/L stock solution of a DSP preparation of engineered transaminase polypeptide was added to start the reaction. Final concentrations of components were: 20 g/L of compound (2); 0.5 g/L PLP; 1 M IPM; 25% v/v DMSO; 2 g/L transaminase polypeptide preparation; and 100 mM TEA, pH 7.0. The mixture was then stirred on a hot plate at 55° C.

Samples of 10 μL were taken at different time points and diluted with 200 μL acetonitrile:water (1:1). 1 μL of concentrated HCl was added to the sample and it was centrifuged for 5 min at 20,000 rpm. These samples were analyzed by HPLC to monitor time course of the reaction. After 24 h. the reaction mixtures were quenched with 10 mL acetonitrile and the mixture analyzed by HPLC to get the final % conversion of compound (2) to product compound (1). Results for % conversion of compound (2) to product compound (1) after 24 h are shown in Table 2B.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered polypeptide having transaminase activity, wherein said engineered polypeptide comprises an amino acid sequence having at least 90% sequence identity to the amino acid sequence of SEQ ID NO: 2, wherein amino acid residues at the positions corresponding to positions 57 and 316 of SEQ ID NO: 2 are mutated in said engineered polypeptide, and further wherein said residue at the position corresponding to position 316 of the amino acid sequence of SEQ ID NO: 2 is selected from cysteine, phenylalanine, glycine, asparagine, serine, and threonine.

2. The engineered polypeptide of claim 1, further comprising amino acid residue mutations at the positions corresponding to positions selected from X19W, X34A, X53M, X73R, X155V, X165F, X171Q, X178W, X251V, X259V, X268A, X277A, X317L, X358K, X366H, X399A, X414I, X426R, and X450S of the amino acid sequence of SEQ ID NO: 2.

3. The engineered polypeptide of claim 1, further comprising at least one additional amino acid residue mutation at the positions corresponding to positions selected from: X34A, X56A, X88H, X107G, X113L, X147H, X153C, X155V, X233V, X315G, X383I, and X450S of the amino acid sequence of SEQ ID NO: 2.

4. The engineered polypeptide of claim 1, further comprising one or more amino acid residue mutations at the positions corresponding to positions selected from: X31M, X86N/S, X153A, X233T, X323T, X383V, and X417T of the amino acid sequence of SEQ ID NO: 2.

5. The engineered polypeptide of claim 4, further comprising amino acid residue mutations at the positions corresponding to positions X34A, X56A, X86S, X88A, X153C, X155V, X163F, X315G, and X417T of the amino acid sequence of SEQ ID NO: 2.

6. The engineered polypeptide of claim 1, wherein said residue at the position corresponding to position 316 of SEQ ID NO: 2 is asparagine.

7. The engineered polypeptide of claim 6, further comprising an amino acid residue mutation at the positions corresponding to positions selected from: X31M, X57F, X323T, X383I/T, X415H, and X450S of the amino acid sequence of SEQ ID NO: 2.

8. The engineered polypeptide of claim 7, wherein said amino acid mutation comprises a combination of amino acid residue mutations at positions corresponding to positions selected from:

X31M, X57F, X323T, and X383V;

X31M, X57F, X107G, X113L, X233T, X415H, and X450S;

X31M, X57F, X233V, X323T, X383I, X415H, and X450S; and

X31M, X57F, X147H, X323T, X383I, X415H, and X450S of the amino acid sequence of SEQ ID NO: 2.

9. The engineered polypeptide of claim 1, wherein said engineered polypeptide having transaminase activity has at least 1.2 fold increased stability as compared to the polypeptide of the amino acid sequence of SEQ ID NO: 4, wherein said engineered polypeptide further comprises one or more amino acid residue mutations at positions corresponding to positions selected from: X34T, X107G, X113L, X147H, X155V, X233T/V, X323T, X383I/V, and X450S of the amino acid sequence of SEQ ID NO: 2.

10. The engineered polypeptide of claim 1, wherein said engineered polypeptide having transaminase activity has at least 1.2 fold increased activity as compared to the polypeptide of the amino acid sequence of SEQ ID NO: 4 in converting compound (2) to compound (1), wherein said engineered polypeptide further comprises one or more amino acid residue mutations at positions corresponding to positions selected from X56A, X86S, X88H, X153C, X415H, and X417T of the amino acid sequence of SEQ ID NO: 2.

11. The engineered polypeptide of claim 1, wherein said engineered polypeptide having transaminase activity has increased enantioselectivity as compared to the polypeptide of the amino acid sequence of SEQ ID NO: 4 in converting compound (2) to compound (1), wherein said engineered polypeptide further comprises the amino acid residue mutation at the position corresponding to position X153C of the amino acid sequence of SEQ ID NO: 2.

12. The engineered polypeptide of claim 1, further comprising an amino acid residue mutation at the positions corresponding to positions selected from: X18A, X19W, X21H, X31M, X34A, X53M, X56A/C, X73R, X86C/N/S/Y, X88H/Y, X107G, X113C/L/P, X146L, X147H/K/V, X153A/C/V, X155A/V, X163L, X165F, X171Q, X178W, X190K, X206K, X228G, X233T/V, X235P, X244T, X251V, X259V, X268A, X277A, X286C/H, X312N, X314N, X315G, X317L, X319N, X323T, X358K, X366H, X383C/F/I/L/M/T/V, X395P, X399A, X414I, X415A/G/H/L/V, X417T/V, X424A, X426A, X426R, X427Y, X434T, and X450S of the amino acid sequence of SEQ ID NO: 2.

13. The engineered polypeptide of claim 1, wherein said engineered polypeptide does not comprise an amino acid residue mutation at the positions corresponding to positions X9, X45, X177, X211, X294, X324, and X291 of the amino acid sequence of SEQ ID NO: 2.

14. The engineered polypeptide of claim 1, said engineered polypeptide comprises an amino acid sequence selected from the amino acid sequences set forth in SEQ ID NOS: 98, 100, 012, 146, 148, 150, 152, 154, 156, 158, 160, 162, 164, 166, 168, 170, 172, 174, 176, 178, 180, 184, 186, 188, 190, 192, and 202.

15. The engineered polypeptide of claim 1, wherein said engineered polypeptide is immobilized on a solid support.

16. The engineered polypeptide of claim 15, wherein said solid support is a bead or resin comprising polymethyacrylate with epoxide functional groups, polymethycrylate with amino epoxide functional groups, styrene/DVB copolymer or polymethyacrylate with octadecyl functional groups.

17. A polynucleotide encoding the engineered polypeptide of claim 1.

18. A polynucleotide encoding the engineered polypeptide of claim 1, wherein said polynucleotide comprises a nucleotide sequence selected from the nucleotide sequences set forth in SEQ ID NOS: 97, 99, 101, 135, 145, 147, 149, 151, 153, 155, 157, 159, 161, 163, 165, 167, 169, 171, 173, 175, 177, 179, 183, 185, 187, 189, 191, and 201.

19. An expression vector comprising the polynucleotide of claim 17.

20. The expression vector of claim 19, wherein said expression vector comprises a control sequence.

21. A host cell comprising the polynucleotide of claim 17.

22. A method of preparing an engineered polypeptide, comprising culturing the host cell of claim 21 under conditions suitable for expression of said engineered polypeptide.

23. The method of claim 22, further comprising isolating said engineered polypeptide.

24. A process for preparing an amine compound of Formula (I), (I)

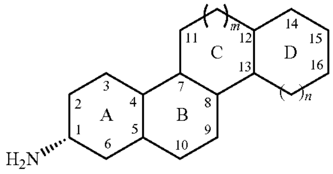

wherein:

Ring A is a 6-membered carbocyclic ring, optionally including an unsaturated C—C bond between positions 2 and 3 and/or positions 5 and 6, and/or optionally substituted independently positions 2, 3, 4, 5 and 6 with a group selected from halo, hydroxy, and methyl;

Ring B is a 6-membered carbocyclic ring, optionally including an unsaturated C—C bond between positions 5 and 10, and/or optionally substituted independently at one or more of positions 9 and 10 with a group selected from halo, hydroxy, and methyl;

Ring C is a 5- or 6-membered carbocyclic ring (m=0 or 1), optionally substituted at position 10 with a group selected from halo, hydroxy, methyl, ethyl, and carbonyl;

Ring D is a 5-, 6-, or 7-membered carbocyclic ring (n=0, 1, or 2), optionally including 1, 2, or 3 unsaturated C—C bonds, and/or optionally substituted independently as follows:

at position 14 with a group selected from halo, hydroxy, amino, carboxy, cyano, nitro, thio, straight-chain or branched (C1-$C_4$)alkyl, straight-chain or branched (C1-$C_4$)alkenyl, straight-chain or branched ($C_1$-$C_3$) alkylamino, and cyclopropyl bridging to position 12;

at position 15 or position 16 with a group selected from halo, hydroxy, amino, carboxy, cyano, nitro, thio, optionally substituted ($C_1$-$C_6$)alkyl, hydroxy($C_1$-$C_6$) alkyl, optionally substituted($C_1$-$C_6$)alkyloxy, optionally substituted ($C_1$-$C_6$)alkylamino, optionally substituted ($C_1$-C)dialkylamino, optionally substituted ($C_1$-$C_6$)alkylthio, optionally substituted ($C_1$-$C_6$) alkylsulfonyl, optionally substituted ($C_1$-$C_6$)alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$) alkyl, optionally substituted cycloalkyl, optionally substituted heterocycloalkyl, optionally substituted aryl, optionally substituted heteroaryl, optionally optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$)alkyl;

with the proviso that said compound of Formula (I) is not compound (1)

(1)

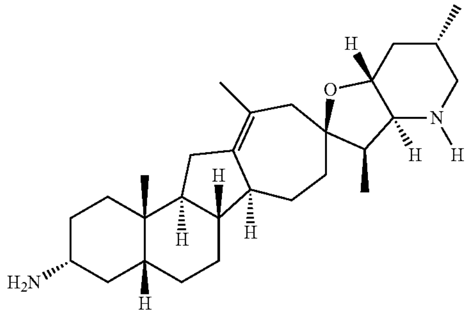

wherein said method comprises contacting the ketone substrate compound of Formula (II), (II)

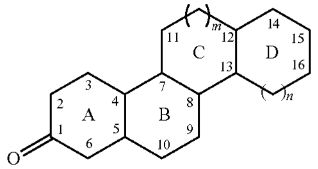

wherein rings A, B, C, and D are as defined above for said compound of formula (I), with the engineered polypeptide of claim 1 in the presence of an amino donor under suitable reaction conditions, thereby producing said amine compound of formula (I).

25. The process of claim 24, wherein said amine compound of Formula (I) is the compound of Formula (Ia)

(Ia)

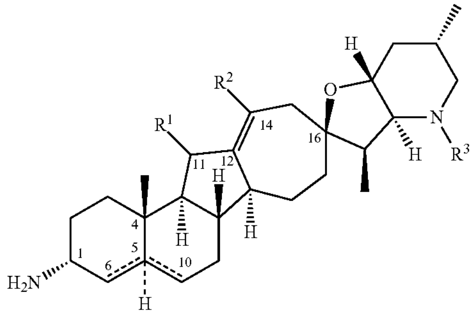

wherein

Rings A and B comprise one of the following:

a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D comprises an unsaturated C—C bond between positions 12 and 14;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched ($C_1$-$C_4$)alkyl, straight-chain or branched (C1-$C_4$)alkenyl, and straight-chain or branched ($C_1$-$C_3$)alkylamino; and $R^3$ is selected from hydrogen, halo, hydroxy, amino, carboxy, cyano, nitro, thio, optionally substituted ($C_1$-$C_6$)alkyl, hydroxy($C_1$-$C_6$)alkyl, optionally substituted ($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy($C_1$-$C_6$)alkyl, ($C_1$-$C_6$) alkyloxycarbonyl, ($C_1$-C)alkylcarbonyloxy, optionally substituted aminocarbonyl, and aminocarbonyl($C_1$-$C_6$) alkyl;

and wherein the method comprises contacting the ketone substrate compound of Formula (IIa), (IIa)

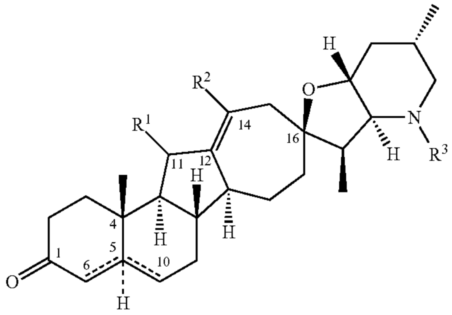

wherein rings A, B, C, and D, and $R^1$, $R^2$, and $R^3$ are as defined above for said Formula (Ia), with the engineered polypeptide of claim 1 in the presence of an amino donor under suitable reaction conditions, thereby producing said amine compound of formula (Ia).

26. The process of claim 24, wherein said amine compound of Formula (I) is the compound of Formula (Ib)

(Ib)

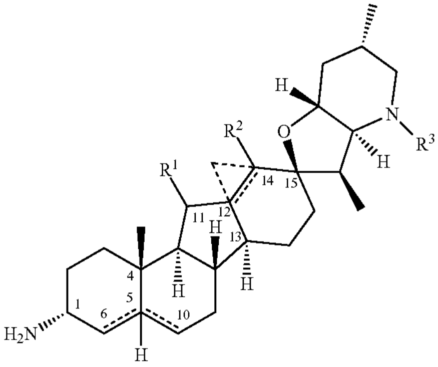

wherein

Rings A and B comprise one of the following:

a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D comprises an unsaturated C—C bond between positions 12 and 14, or a bridging cyclopropyl between positions 12 and 14;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched ($C_1$-$C_4$)alkyl, straight-chain or branched (C1-$C_4$)alkenyl, and straight-chain or branched ($C_1$-$C_3$)alkylamino; and $R^3$ is selected from hydrogen, halo, hydroxy, amino, carboxy, cyano, nitro, thio, optionally substituted ($C_1$-$C_6$)alkyl, hydroxy($C_1$-$C_6$)alkyl, optionally substituted ($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-C)alkylsulfonyl, optionally substituted ($C_1$-$C_6$)alkylsulfinyl, carboxy($C_1$-$C_6$)alkyl, ($C_1$-$C_6$) alkyloxycarbonyl, ($C_1$-C)alkylcarbonyloxy, optionally substituted aminocarbonyl, and aminocarbonyl($C_1$-$C_6$) alkyl;

and wherein the method comprises contacting the ketone substrate compound of Formula (IIb), (IIb)

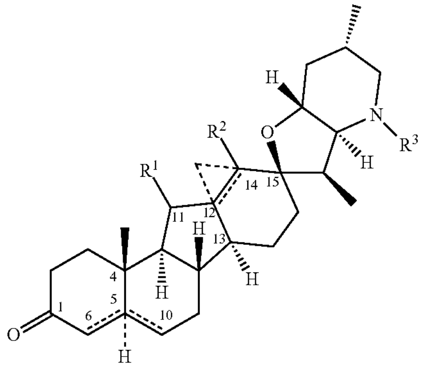

wherein rings A, B, C, and D, and $R^1$, $R^2$, and $R^3$ are as defined above for said Formula (Ib), with the engineered polypeptide of claim 1 in the presence of an amino donor under suitable reaction conditions, thereby producing said amine compound of formula (Ib).

27. The process of claim 24, wherein said amine compound of Formula (I) is the compound of Formula (Ic)

(Ic)

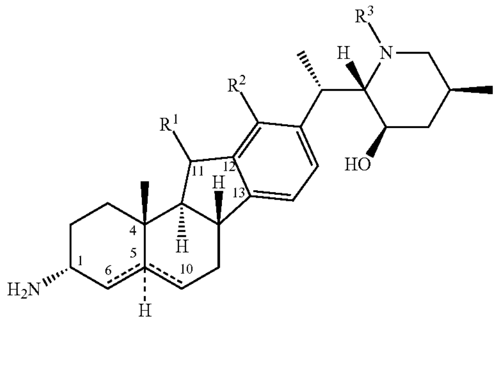

wherein

Rings A and B comprise one of the following:

a) an unsaturated C—C bond between positions 5 and 6;

(b) an unsaturated C—C bond between positions 5 and 10;

(c) a hydrogen at position 5 cis to the methyl group at position 4; or (d) a hydrogen at position 5 trans to the methyl group at position 4;

Ring D is aromatic;

$R^1$ is selected from hydrogen, halo, hydroxy, methyl, ethyl, and carbonyl;

$R^2$ is selected from hydrogen, halo, hydroxy, amino, carboxy, cyano, nitro, thio, straight-chain or branched $(C_1\text{-}C_4)$alkyl, straight-chain or branched (C1-$C_4$)alkenyl, and straight-chain or branched $(C_1\text{-}C_3)$alkylamino; and $R^3$ is selected from hydrogen, halo, hydroxy, amino, carboxy, cyano, nitro, thio, optionally substituted $(C_1\text{-}C_6)$alkyl, hydroxy$(C_1\text{-}C_6)$alkyl, optionally substituted $(C_1\text{-}C_6)$alkyloxy, optionally substituted $(C_1\text{-}C_6)$alkylamino, optionally substituted $(C_1\text{-}C_6)$dialkylamino, optionally substituted $(C_1\text{-}C_6)$alkylthio, optionally substituted $(C_1\text{-}C)$alkylsulfonyl, optionally substituted $(C_1\text{-}C_6)$alkylsulfinyl, carboxy$(C_1\text{-}C_6)$alkyl, $(C_1\text{-}C_6)$alkyloxycarbonyl, $(C_1\text{-}C)$alkylcarbonyloxy, optionally substituted aminocarbonyl, and aminocarbonyl$(C_1\text{-}C_6)$alkyl;

and wherein the method comprises contacting the ketone substrate compound of Formula (IIc), (IIc)

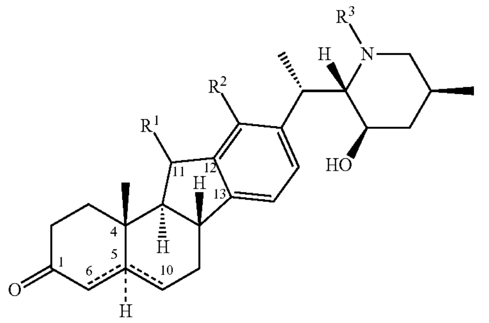

wherein rings A, B, C, and D, and $R^1$, $R^2$, and $R^3$ are as defined above for said Formula (Ic), with the engineered polypeptide of claim 1 in the presence of an amino donor under suitable reaction conditions, thereby producing said amine compound of formula (Ic).

28. The process of claim 24, wherein said amine compound of Formula (I) is the compound of Formula (Id)

(Id)

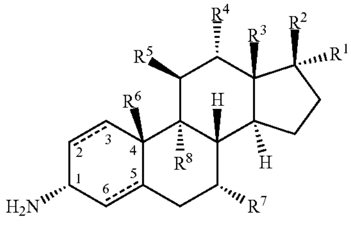

wherein

Ring A comprises an unsaturated C—C bond between positions 2 and 3, or positions 5 and 6;

$R^1$ and $R^2$ are selected independently from hydrogen, halo, hydroxy, amino, carboxy, cyano, nitro, thio, optionally substituted $(C_1\text{-}C_6)$alkyl, hydroxy$(C_1\text{-}C_6)$alkyl, optionally substituted$(C_1\text{-}C_6)$alkyloxy, optionally substituted $(C_1\text{-}C_6)$alkylamino, optionally substituted $(C_1\text{-}C_6)$dialkylamino, optionally substituted $(C_1\text{-}C_6)$alkylthio, optionally substituted $(C_1\text{-}C)$alkylsulfonyl, optionally substituted $(C_1\text{-}C_6)$alkylsulfinyl, carboxy$(C_1\text{-}C_6)$alkyl, $(C_1\text{-}C_6)$alkyloxycarbonyl, $(C_1\text{-}C)$alkylcarbonyloxy, optionally substituted aminocarbonyl, and aminocarbonyl$(C_1\text{-}C_6)$alkyl, optionally substituted cycloalkyl, optionally substituted heterocycloalkyl, optionally substituted aryl, optionally substituted heteroaryl, optionally substituted, aryloxy, optionally substituted arylamino, optionally substituted arylthio, optionally substituted aryl sulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl$(C_1\text{-}C_6)$alkyl, arylsulfonyl$(C_1\text{-}C_6)$alkyl, and heteroarylsulfonyl$(C_1\text{-}C_6)$alkyl;

$R^3$, $R^4$, and $R^5$ are selected independently from hydrogen, halo, hydroxyl, amino, carboxy, cyano, nitro, thio, straight-chain or branched $(C_1\text{-}C_4)$alkyl, straight-chain or branched $(C_1\text{-}C_4)$alkenyl, and straight-chain or branched $(C_1\text{-}C_3)$alkylamino; and $R^6$, $R^7$, and $R^8$ are selected independently from hydrogen, halo, hydroxyl, and methyl;

wherein the method comprises contacting the ketone substrate compound of Formula (IId), (IId)

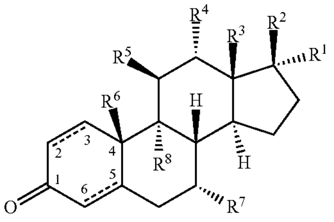

wherein $R^1$, $R^2$, $R^3$, $R^4$, $R^5$, $R^6$, $R^7$, and $R^8$ are as defined above for the compound of Formula (Id), with the engineered polypeptide of claim 1 in the presence of an amino donor under suitable reaction conditions, thereby producing said amine compound of formula (Id).

29. The process of claim 24, wherein said ketone substrate compound of Formula (II) is at a loading of 0.5 to 200 g/L, 1 to 200 g/L, 5 to 150 g/L, 10 to 100 g/L, or 20 to 100 g/L.

30. The process of claim 24, wherein said amino donor is selected from the group consisting of isopropylamine, L-lysine, a-phenethylamine, D-alanine, L-alanine, or D,L-alanine, or D,L-ornithine.

31. The process of claim 24, wherein said suitable reaction conditions comprise a buffer, selected from borate, phosphate, carbonate, triethanolamine (TEA), and Tris.

32. The process of claim 24, wherein said suitable reaction conditions comprise a pH from 6 to 12, pH from 6 to 10, pH from 6 to 8, pH from 7 to 10, pH from 7 to 9, or pH from 7 to 8.

33. The process of claim 24, wherein said suitable reaction conditions comprise a temperature of 10° C. to 70° C., 10° C. to 65° C., 15° C. to 60° C., 20° C. to 60° C., 20° C. to 55° C., 30° C. to 55° C., or 50° C. to 60° C.

34. The process of claim 24, wherein said suitable reaction conditions comprise a pyridoxal cofactor, pyridoxal-5'-phosphate (PLP), at a concentration from 0.1 g/L to 10 g/L, 0.2 g/L to 5 g/L, or 0.5 g/L to 2.5 g/L.

35. The process of claim 24, wherein said suitable reaction conditions comprise a co-solvent.

36. The process of claim 35, wherein said co-solvent comprises a polar co-solvent.

37. The process of claim 36, wherein said polar co-solvent is selected from polyol, DMSO, or lower alcohol.

38. The process of claim 24, in which the transaminase polypeptide is at a concentration of 0.01 to 50 g/L, 0.05 to 50 g/L, 0.1 to 40 g/L, 1 to 40 g/L, 2 to 40 g/L, 5 to 40 g/L, 5 to 30 g/L, 0.1 to 10 g/L, 0.5 to 10 g/L, 1 to 10 g/L, 0.1 to 5 g/L, 0.5 to 5 g/L, or 0.1 to 2 g/L.

* * * * *